(12) United States Patent
Timans

(10) Patent No.: US 8,152,365 B2
(45) Date of Patent: Apr. 10, 2012

(54) METHOD AND SYSTEM FOR DETERMINING OPTICAL PROPERTIES OF SEMICONDUCTOR WAFERS

(75) Inventor: Paul Janis Timans, Mountain View, CA (US)

(73) Assignee: Mattson Technology, Inc., Fremont, CA (US)

( * ) Notice: Subject to any disclaimer, the term of this patent is extended or adjusted under 35 U.S.C. 154(b) by 745 days.

(21) Appl. No.: 11/478,342

(22) Filed: Jun. 29, 2006

(65) Prior Publication Data

US 2007/0020784 A1 Jan. 25, 2007

Related U.S. Application Data

(60) Provisional application No. 60/696,608, filed on Jul. 5, 2005.

(51) Int. Cl.
*G01J 5/00* (2006.01)
*G01N 21/00* (2006.01)

(52) U.S. Cl. .................. 374/130; 374/121; 250/339.11; 250/341.8; 356/445; 356/432

(58) Field of Classification Search .................. 374/121, 374/130; 250/339.11, 341.8; 356/445, 432
See application file for complete search history.

(56) References Cited

U.S. PATENT DOCUMENTS

| | | | |
|---|---|---|---|
| 3,693,025 A | 9/1972 | Brunton | |
| 4,062,623 A | 12/1977 | Suzuki et al. | |
| 4,120,590 A | 10/1978 | Bieringer et al. | |
| 4,284,356 A | 8/1981 | Heilman | |
| 4,342,907 A | 8/1982 | Macedo et al. | |
| 4,448,524 A | 5/1984 | Brus et al. | |
| 4,468,136 A | 8/1984 | Murphy et al. | |
| 4,756,627 A | 7/1988 | Nelson | |
| 4,831,276 A | 5/1989 | Hyakumura | |
| 4,841,150 A | 6/1989 | Walter | |
| 5,229,303 A | 7/1993 | Donnelly, Jr. et al. | |
| 5,298,974 A | 3/1994 | Chandley | |

(Continued)

FOREIGN PATENT DOCUMENTS

JP 2002-122480 4/2002

(Continued)

OTHER PUBLICATIONS

"Influence of temperature and backside roughness on the emissivity of Si wafers during rapid thermal processing"; Authors, Vandenabeele and Maex in J. Appl. Phys. vol. 72, No. 12, (Dec. 15, 1992), pp. 5867-5875.

(Continued)

*Primary Examiner* — Lisa Caputo
*Assistant Examiner* — Mirellys Jagan
(74) *Attorney, Agent, or Firm* — Dority & Manning, P.A.

(57) ABSTRACT

A method and system are disclosed for determining at least one optical characteristic of a substrate, such as a semiconductor wafer. Once the optical characteristic is determined, at least one parameter in a processing chamber may be controlled for improving the process. For example, in one embodiment, the reflectivity of one surface of the substrate may first be determined at or near ambient temperature. From this information, the reflectance and/or emittance of the wafer during high temperature processing may be accurately estimated. The emittance can be used to correct temperature measurements using a pyrometer during wafer processing. In addition to making more accurate temperature measurements, the optical characteristics of the substrate can also be used to better optimize the heating cycle.

19 Claims, 25 Drawing Sheets

U.S. PATENT DOCUMENTS

| | | | |
|---|---|---|---|
| 5,377,126 A * | 12/1994 | Flik et al. | 700/300 |
| 5,381,229 A | 1/1995 | Murphy et al. | |
| 5,501,637 A * | 3/1996 | Duncan et al. | 374/126 |
| 5,572,314 A | 11/1996 | Hyman, Jr. et al. | |
| 5,628,564 A | 5/1997 | Nenyei et al. | |
| 5,683,180 A | 11/1997 | De Lyon et al. | |
| 5,727,017 A * | 3/1998 | Maurer et al. | 374/9 |
| 5,841,110 A | 11/1998 | Nenyei et al. | |
| 5,874,711 A | 2/1999 | Champetier et al. | |
| 5,913,974 A | 6/1999 | Habuka | |
| 5,991,037 A | 11/1999 | Piel et al. | |
| 5,997,175 A | 12/1999 | Champetier et al. | |
| 6,027,244 A | 2/2000 | Champetier et al. | |
| 6,034,357 A | 3/2000 | Guardado | |
| 6,054,868 A | 4/2000 | Borden et al. | |
| 6,056,434 A * | 5/2000 | Champetier | 374/126 |
| 6,062,729 A | 5/2000 | Ni et al. | |
| 6,088,092 A | 7/2000 | Chen et al. | |
| 6,108,077 A | 8/2000 | Heaton et al. | |
| 6,151,125 A | 11/2000 | Mitsuhashi | |
| 6,151,446 A | 11/2000 | Hunter et al. | |
| 6,160,242 A | 12/2000 | Guardado | |
| 6,166,808 A | 12/2000 | Greve | |
| 6,191,392 B1 | 2/2001 | Hauf et al. | |
| 6,200,023 B1 | 3/2001 | Tay et al. | |
| 6,204,484 B1 | 3/2001 | Tay et al. | |
| 6,293,696 B1 | 9/2001 | Guardado | |
| 6,359,263 B2 | 3/2002 | Tay et al. | |
| 6,369,363 B2 | 4/2002 | Hauf et al. | |
| 6,398,406 B1 | 6/2002 | Breiland et al. | |
| 6,403,923 B1 | 6/2002 | Tay et al. | |
| 6,426,232 B1 | 7/2002 | Litvak | |
| 6,462,315 B2 | 10/2002 | Hauf | |
| 6,654,132 B1 | 11/2003 | Schietinger et al. | |
| 6,683,695 B1 | 1/2004 | Simpson et al. | |
| 6,819,423 B2 | 11/2004 | Stehle et al. | |
| 6,835,914 B2 | 12/2004 | Timans | |
| 7,009,695 B2 | 3/2006 | Some | |
| 7,015,422 B2 | 3/2006 | Timans | |
| 7,056,389 B2 | 6/2006 | Hauf et al. | |
| 7,112,763 B2 | 9/2006 | Hunter et al. | |
| 7,135,656 B2 | 11/2006 | Timans | |
| 7,169,717 B2 | 1/2007 | Merkl et al. | |
| 7,234,862 B2 * | 6/2007 | Johnson et al. | 374/131 |
| 2002/0189757 A1 * | 12/2002 | Denton et al. | 156/345.27 |
| 2003/0236642 A1 | 12/2003 | Timans | |
| 2004/0061057 A1 * | 4/2004 | Johnson et al. | 250/341.1 |
| 2005/0008351 A1 | 1/2005 | Gat et al. | |
| 2005/0063453 A1 | 3/2005 | Camm et al. | |
| 2007/0009010 A1 * | 1/2007 | Shio et al. | 374/161 |

FOREIGN PATENT DOCUMENTS

| | | |
|---|---|---|
| WO | WO 0073533 A1 | 12/2000 |

OTHER PUBLICATIONS

"Infrared absorption in silicon at elevated temperatures"; Authors, Rogne et al.; Published in Appl. Phys. Lett. 69, pp. 2190-2192 (Oct. 7, 1996).

"The Thermal Radiative Properties of Semiconductors" in the book "Advances in Rapid Thermal and Integrated Processing", edited by F. Roozeboom (Kluwer Academic Publishers, Dordrecht, Netherlands, 1995) p. 35.

"A new optical temperature measurement technique for semiconductor substrates in molecular beam epitaxy"; Authors, Weilmeier et al.; Published, Can. J. Phys. vol. 69, 1991 p. 422-426.

"Use of SiC band gap temperature dependence for absolute calibration of emissivity corrected pyrometers in III-nitride MOVPE"; Authors, R. Steins et al.; Published, Journal of Crystal Growth 272 (2004) p. 81-86.

"Temperature Measurement of Metal-Coated Silicon Wafers by Double-Pass Infrared Transmission", Authors, Cullen et al. (IEEE Trans. Semiconductor Manufacturing 8, 346 (1995).

Search Report for Int'l Appl. No. PCT/US06/25288, date of mailing Mar. 2, 2007.

Paul J. Timans, U.S. Appl. No. 11/478,312, filed Jun. 29, 2006, Methods for Determining Wafer Temperature.

Search Report for International Application No. PCT/US07/72488, dated Jan. 9, 2009.

* cited by examiner

Schematic of propagation of rays for light incident on front surface of wafer, and values for intensity of light at various positions Temperature dependence of the optical properties of a wafer where the substrate has a temperature-dependent absorption coefficient General approach for pre-measuring wafer properties at one temperature, predicting property at a second temperature, and processing a wafer on the basis of the predicted property Example approach for pre-measuring wafer properties at several wavelengths and temperatures, predicting properties at a processing temperature, and processing a wafer on the basis of the predicted properties

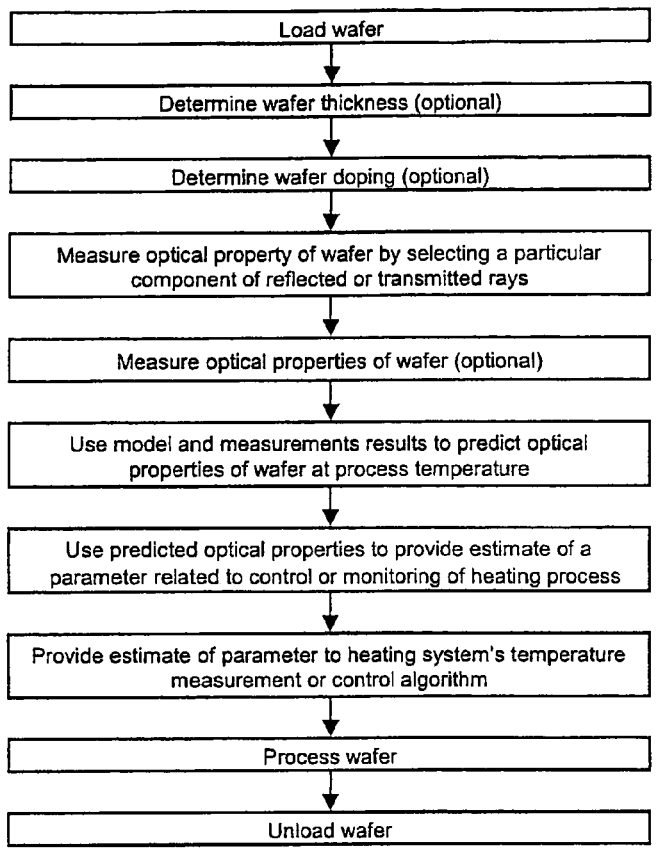

Example approach for pre-measuring wafer properties, including a measurement where the optical property that is measured is determined by selecting particular reflected or transmitted rays. Properties at a processing temperature are predicted at least in part on the basis of this measurement, and the wafer is processed on the basis of the predicted properties

FIG. 23

Example approach for pre-measuring wafer properties, including a measurement where the reflectivity of a surface is measured and the emittance at a processing temperature is predicted. The wafer is processed, using the determined value of emittance to improve temperature measurement or control.

Example approach for pre-measuring wafer properties, and using measurements to determine a doping characteristic of a wafer. The doping characteristic is then used to predict a wafer property at the process temperature.

Example approach for using wafer thickness information to improve control or monitoring of a heating process.

METHOD AND SYSTEM FOR DETERMINING OPTICAL PROPERTIES OF SEMICONDUCTOR WAFERS

RELATED APPLICATIONS

The present application is based upon and claims priority to a provisional application having U.S. Ser. No. 60/696,608 filed on Jul. 5, 2005.

BACKGROUND OF THE INVENTION

The accurate measurement of surface temperatures of hot objects is of concern in many industrial and scientific processes. For instance, temperatures must be accurately measured and controlled during the fabrication of semiconductor devices. In particular, the temperature of semiconductor wafers must be accurately monitored during rapid thermal processing of the wafers, during rapid thermal oxidation of the wafers, or during other processes which modify or add thin chemical films or coatings to the surface of the wafers. For these semiconductor fabrication processes, the temperature of the substrate should be known within a few degrees over a range which may extend from less than 400.degree. C. to over 1,100.degree. C.

In the past, the temperature of hot objects was determined either using (1) contact methods or (2) non-contact methods. For instance, during contact methods, the hot object is contacted with a sensor such as a thermocouple that is in turn connected to a temperature meter, which indicates the temperature of the object. Conventional non-contact methods of determining temperature, on the other hand, include using a light sensor such as an optical pyrometer that senses the thermal radiation being emitted by the object at a particular wavelength of light. Once the thermal radiation being emitted by the object is known, the temperature of the object can be estimated.

When processing semiconductor materials for use in the electronics industry, it is generally preferable to use non-contact methods when measuring the temperature of the semiconductor wafers. For instance, one advantage of non-contact methods is that the wafer can be rotated during the heating process, which promotes uniform temperature distribution throughout the wafer. Rotating the wafer also promotes more uniform contact between the flow of processing gases and the wafer. Besides being able to rotate the wafers, another advantage to using non-contact methods is that, since no temperature gauges need be attached to the wafer, the wafers can be processed much more quickly saving precious time during semiconductor fabrication.

For all of the high temperature wafer processes of current and foreseeable interest, one of the more important requirements is that the true temperature of the wafer be determined with high accuracy, repeatability and speed. The ability to accurately measure the temperature of a wafer has a direct payoff in the quality and size of the manufactured semiconductor devices. For instance, the smallest feature size required for a given semiconductor device limits the computing speed of the finished microchip. The feature size in turn is linked to the ability to measure and control the temperature of the device during processing. Thus, there is increasing pressure within the semiconductor industry to develop more accurate temperature measurement and control systems.

In this regard, the chief disadvantage of conventional non-contact optical pyrometry systems for determining temperature is that the systems measure an apparent temperature rather than the true temperature of the wafer. In particular, a real surface emits radiation less efficiently than an ideal or perfect blackbody. Through theory and calculation, once the emitted radiation of a blackbody is known, the temperature of the blackbody can be calculated. A real body, however, such as a wafer, emits only a fraction of the radiation that would be emitted by a blackbody at the same temperature. This fraction is defined as the emittance of the real object. Thus, when sensing the radiation being emitted by a real body, a pyrometer generally indicates an apparent temperature that can be different from the true temperature of the object.

Thus, in order to measure the true temperature of a real body using a pyrometer, the indicated temperature must be corrected to account for the emittance. Unfortunately, the emittance of a real body is generally unknown and is very difficult to measure accurately. Further, the emittance of semiconductor wafers varies from wafer to wafer. The emittance is a property of the wafer and depends on several parameters, such as the chemical composition of the wafer, the thickness of the wafer, the surface roughness of the wafer, any coatings present on the wafer and the wavelength at which the pyrometer operates.

In addition to being able to determine the emittance of the semiconductor wafer, problems in accurately determining the temperature of the wafer can also occur when the wafer is semi-transparent at the wavelength at which the pyrometer operates. This problem is especially prevalent at lower temperatures.

In the past, some methods have been proposed for measuring the properties of the semiconductor wafer prior to processing the wafer or during processing of the wafer. For example, U.S. Pat. No. 6,056,434 discloses a method by which the reflectivity of the semiconductor wafer is measured to assist in determining the emittance of the wafer.

The present disclosure is directed to further improvements in methods for determining the optical properties of substrates, such as semiconductor wafers that are to be processed in thermal processing chambers. The properties or characteristics of the wafer that are determined according to the present disclosure may then be used to better control the heating process and/or the manner in which the substrate is heated.

SUMMARY OF THE INVENTION

The present disclosure is generally directed to a method for determining the optical characteristics of a substrate, such as a semiconductor wafer in order to more accurately heat the wafer during a heating process or to otherwise better control various system components or variables during the heating process. The system and method disclosed allow for improved accuracy and wafer temperature readings by a radiation sensing device, such as a pyrometer, or for improved measurements and/or prediction of the thermal radiative properties of the substrate. In one embodiment, the optical characteristics of the substrate determined according to the method can be supplied to a controller for improved wafer temperature control.

In one embodiment, for example, the present disclosure is directed to a method for determining at least one optical characteristic of a semiconductor wafer. The method includes the steps of emitting light onto a first surface of the semiconductor wafer having a particular thickness. The light that is emitted onto the first surface of the semiconductor wafer is directed through an optical pathway that is configured to separate the light reflected from the first surface from light that passes through the wafer and is reflected off a second and opposite surface of the wafer.

Once the light reflected from the first surface is separated from the light reflected from the second surface, the light reflected from the first surface can be detected using a detector. The detector may be, for instance, any suitable photosensor and may be configured to detect the amount of light reflected from the first surface at a certain wavelength or at a certain wavelength range.

In accordance with the present disclosure, based on the amount of detected light reflected from the first surface, at least one optical characteristic of the semiconductor wafer is then determined. The characteristic may comprise a reflectivity of the first surface, an emissivity of the first surface, an absorptivity of the first surface, or a transmissivity of the first surface. Alternatively or in addition, the optical characteristic may comprise a reflectance, an emittance, an absorptance or a transmittance of the semiconductor wafer. Further, instead of or in addition to determining at least one optical characteristic of a first surface of the semiconductor wafer, the method can also be used to determine at least one optical characteristic of an opposite surface of the wafer.

The optical pathway that is used in order to separate the light reflected from the first surface from the light reflected from the second surface may vary depending upon the particular application. The optical pathway, for example, may comprise a plurality of optical devices. The optical devices can comprise mirrors, lenses, apertures, and the like. In one particular embodiment, for instance, the optical pathway includes a first lens and a second lens which direct the light onto a particular location of the first surface of the semiconductor wafer. After the light reflects off the first surface, the light then again passes through the second lens. From the second lens, the light is reflected off a mirror and passes through a third lens so as to be focused onto a light detector. It should be understood, however, that the above embodiment merely represents one example of an optical pathway that may be used in the present disclosure.

The manner in which the light reflected from the first surface is separated from the light reflected from the second surface as the light travels through the optical pathway may also vary from application to application. Separating the different light beams, for example, may be carried out by adjusting the focal length of one or more lenses in the system. Alternatively or in addition, the system may include various apertures or filters in order to separate the different light streams. In still other embodiments, the light may be emitted onto the first surface of the semiconductor wafer at a distribution of angles of incidence in order to separate the light reflected from the first surface from the light reflected from the second surface.

The light source that may be used in order to emit light onto the first surface of the substrate can vary depending upon the particular application. For instance, in one embodiment, the light may comprise a broad band light source. Alternatively, the light source may emit a laser beam.

Once at least one optical characteristic of the semiconductor wafer is determined based upon the above method, the optical characteristic may be used and incorporated into various systems and processes. For example, in one embodiment, the one or more optical characteristics that are determined are used to control a heating process for the semiconductor wafer. In this embodiment, based upon the optical characteristic, at least one system component in a process for heating the semiconductor wafer can be controlled.

For instance, in one embodiment, the system component may comprise a temperature measurement system that includes a radiation measuring device, such as a pyrometer, that senses the amount of radiation being emitted by the semiconductor wafer during heating for determining the temperature of the semiconductor wafer. The amount of detected light from the first surface may be used to determine the emittance of the semiconductor wafer for use in determining the temperature of the semiconductor wafer in conjunction with the amount of radiation being sensed by the radiation measuring device.

In this embodiment, for example, the radiation sensing device senses radiation being emitted by the semiconductor wafer at a certain wavelength. The amount of light that is reflected from the first surface of the semiconductor wafer is detected at the same wavelength at which the radiation sensing device operates. The measurement of the amount of reflected light that is detected from the first surface of the semiconductor substrate may also occur at a temperature less than about 100° C. For example, the amount of detected light from the first surface of the semiconductor wafer may be used to determine reflectance and emittance of the semiconductor wafer at temperatures where the transmittance of the semiconductor wafer is less than 0.1 at the wavelength at which the radiation sensing device operates. More particularly, in one embodiment, the reflectance and/or the emittance that is determined at a temperature less than about 100° C. can be used to predict the emittance of the substrate at higher temperatures using, for instance, a model.

In an alternative embodiment, the system component may be related to the heating device that is used to heat the wafer. During the heating process, for instance, a power controller for a heating device that is used to heat the semiconductor wafer may be adjusted. The heating device may comprise, for instance, an array of light energy sources, a heated susceptor, or a mixture of both. The amount of detected light from the first surface of the semiconductor wafer may be used to determine absorptance of the semiconductor wafer during heating for adjusting the power controller and thereby selectively increasing or decreasing the amount of energy being used to heat the semiconductor wafer. In this manner, the absorptance is used to optimize the power or energy setting. In this embodiment, the light that is reflected from the first surface of the semiconductor wafer and detected may be at a wavelength range that substantially overlaps a range of wavelengths of electromagnetic radiation that is used to heat the wafer.

In still another embodiment of the present disclosure, the optical characteristics of the semiconductor wafer that are determined may be used to correct the readings of the radiation sensing device at lower temperatures where transmittance is greater than 0.1 at the wavelength at which the radiation sensing device operates. In this embodiment, a light source emits light that is incident on the first surface of the wafer and the amount of light reflected from the first surface is detected separately from the amount of light that is reflected from the opposite surface of the wafer. For example, an optical pathway may be used in order to separate the reflected light from the first surface of the wafer from the reflected light from the opposite surface of the wafer. This information is then used to determine a reflectivity of both surfaces of the wafer. The reflectivities are then used to determine transmittance and emittance of the semiconductor wafer at temperatures where the transmittance of the semiconductor wafer is greater than 0.1 at the wavelength at which the radiation sensing device operates. The transmittance and emittance that are determined may then be used to correct for temperature measurements that are taken with the radiation sensing device.

In a similar manner, the method of the present disclosure can also be used to control the power or energy level of the heating device at lower temperatures as well. In this embodiment, however, the reflected light off the first surface of the semiconductor wafer and off the second surface of the semiconductor wafer are detected at a wavelength range that substantially overlaps with the wavelength range of the electromagnetic radiation that is used to heat the wafer. In this manner, absorptance can be determined and used to optimize power or energy settings.

The optical characteristics of the semiconductor wafer may be determined as described above within the thermal processing chamber or outside of the chamber. For instance, in one embodiment, the optical characteristics may be determined at any suitable location. For instance, the measurements may occur at a station on a robotic arm or in a separate chamber. Once the optical characteristics are determined, the wafer can then be transferred to a thermal processing chamber for undergoing various processes. The optical characteristics can then be used to control at least one system component in the thermal processing system.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which:

FIGS. 21 through 26 are different embodiments of flow charts of methods for measuring wafer properties in accordance with the present disclosure.

Figure 1:
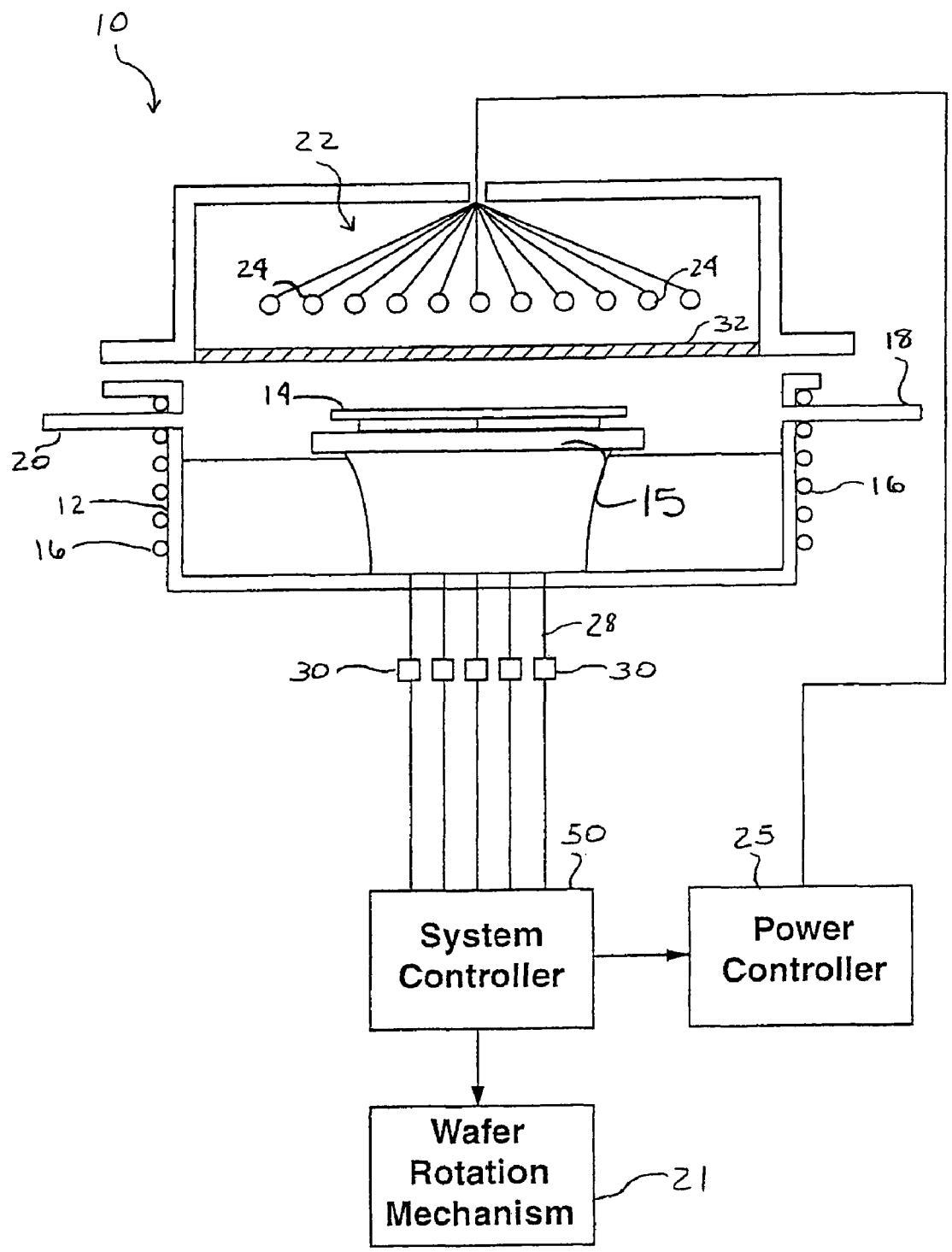
FIG. 1 is a side view of one embodiment of a thermal processing chamber that may be used with the method and system of the present invention.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present invention.

In general, the present disclosure is directed to a method and to a system for determining at least one optical characteristic of a substrate and then using the characteristic to control a process that is carried out on the substrate. For example, in one embodiment, the substrate may comprise a semiconductor wafer and the optical characteristic is used to better determine and control the temperature of the wafer during a heating process. Alternatively, the optical characteristic may be used to control a heating device that is used to heat the wafer.

It should be understood, that the methods of the present disclosure may be used in conjunction with other substrates in addition to semiconductor wafers. For instance, the methods of the present disclosure may be used with any suitable substrate, such as ribbons, films, fibers, filaments, and the like.

When the substrate comprises a semiconductor material, the methods of the present invention can be used during heat treatment of the substrate, during oxidation of the substrate, or during other processes which modify or add films to the surface of the substrate. Other processes that may be used in accordance with the present invention, for instance, include any suitable film deposition process, such as a chemical vapor deposition process or an atomic layer deposition process. The principles of the present invention may also be used during plasma processing for depositing a material on a substrate or for etching a substrate.

Referring to FIG. 1, one exemplary embodiment of a system generally 10 that may be used in the process of the present invention for processing substrates, such as semiconductor wafers, is illustrated. System 10 includes a processing chamber 12 adapted to receive substrates such as a wafer 14 for conducting the various processes. The wafer 14 may be placed in the processing chamber 12 on a substrate holder 15 that, optionally, may be configured to rotate the wafer. Chamber 12 is designed to heat the wafer 14 at very rapid rates and under carefully controlled conditions. Chamber 12 can be made from various materials, including certain metals, glasses and ceramics. For instance, chamber 12 can be made from stainless steel or quartz.

When chamber 12 is made from a heat conductive material, the chamber may include a cooling system. For instance, as shown in FIG. 1, chamber 12 includes a cooling conduit 16 wrapped around the perimeter of the chamber. Conduit 16 is adapted to circulate a cooling fluid, such as water, which is used to maintain the walls of the chamber 12 at a constant temperature.

Chamber 12 can also include a gas inlet 18 and a gas outlet 20 for introducing a gas into the chamber and/or for maintaining the chamber within a preset pressure range. For instance, a gas can be introduced into chamber 12 through gas inlet 18 for reaction with the wafer 14. Once processed, the gas can then be evacuated from the chamber using gas outlet 20.

Alternatively, an inert gas can be fed to the chamber 12 through the gas inlet 18 for preventing any unwanted or undesirable side reactions from occurring within the chamber. In a further embodiment, gas inlet 18 and gas outlet 20 can be used to pressurize the chamber 12. A vacuum can also be created in the chamber 12 when desired.

During processing, the chamber 12 can be adapted to rotate the wafer 14 using a wafer rotation mechanism 21. Rotating the wafer may promote greater temperature uniformity over the surface of the wafer and may promote enhanced contact between the wafer 14 and any gases introduced into the chamber. It should be understood, that besides semiconductor wafers, the chamber is also adapted to process optical parts, films, fibers, ribbons and other substrates having any particular shape.

One or more heating devices may be placed in association with the chamber for heating the wafer 14 during processing. In this embodiment, a heating device 22 includes a plurality of lamps 24, such as tungsten halogen lamps, arc lamps, lasers or mixtures thereof. The heating device 22 can include a reflector or set of reflectors for directing thermal energy being emitted by the heating device onto the wafer 14. As shown in FIG. 1, the lamps 24 may be placed above the wafer 14. It should be understood, however, that the lamps may be placed at any particular location. For instance, additional lamps may be included within the system 10 that are positioned not only above the wafer 14 but below the wafer 14 as well.

As an alternative to using a plurality of lamps or in addition to the lamps, the processing chamber may also include various other heating devices. For instance, the heating device may emit any suitable electromagnetic radiation configured to heat the substrate. The heating device may emit, for instance, radio frequency or microwave energy. In other embodiments, the substrate may be heated in a hot wall environment or through convective heating. A substrate may also be heated with energy beams. The energy beams may comprise, for instance, plasma beams, electron beams, or ion beams.

In one particular embodiment, the processing chamber may include a heated susceptor. For instance, a heated susceptor may be positioned above or below the wafer for heating the wafer without contacting the wafer. Such heated susceptors are well known in the art.

As shown in FIG. 1, the one or more heating devices, such as the lamps 24 may be equipped with a gradual power controller 25 that can be used to increase or decrease the thermal energy being emitted by the heating device.

The thermal processing chamber 10 further includes a plurality of optical fibers or light pipes 28 which are, in turn, in communication with a plurality of corresponding light detectors 30. The optical fibers 28 are configured to receive thermal energy being emitted by the wafer 14 at a particular wavelength. The amount of sensed radiation is then communicated to the light detectors 30 which generate a usable voltage signal for determining the temperature of the wafer. In one embodiment, each optical fiber 28 in combination with a light detector 30 comprises a pyrometer.

During the process, system 10 may be designed such that the optical fibers only detect thermal radiation being emitted by the wafer 14 and not detect radiation being emitted by the lamps 24. In this regard, system 10 includes a filter 32 which inhibits thermal radiation being emitted by the lamps at the wavelength at which the light detectors 30 operate from entering the chamber 12. Filter 32 can be a window and, in one embodiment, can be comprised of fused silica or quartz.

As described above, the temperature of the semiconductor wafer 14 is monitored during processing by the optical fibers 28 and the light detectors 30. Specifically, the light detectors 30 sense the amount of radiation being emitted by the wafer 14 at a particular wavelength for determining the temperature. In order to accurately calculate the temperature based upon the amount of radiation sensed by the light detectors 30, various characteristics of the wafer 14 must be known or otherwise estimated. For example, temperature determinations are based upon the reflectance, transmittance, and/or the emittance of the wafer 14 which are often times difficult to predict or estimate. These values can change not only based upon the temperature of the wafer 14 but also can change due to any structures that may be built on the wafer 14 as it is processed.

In the past, many attempts have been made in order to devise a non-contact temperature measurement system that is capable of either determining or estimating the characteristics of the wafer 14. In some embodiments, for instance, the measurements or determinations are made while the wafer is being processed. For example, U.S. Pat. No. 6,056,434, which is incorporated herein by reference, discusses an in-situ temperature determination process that utilizes a reflectometer.

In other embodiments, attempts have been made to measure various characteristics of the substrate before it is processed. As described above, however, the optical properties of the substrate may change with temperature. Also, some of the materials present on the substrate may undergo a transformation or other materials may be formed on the substrate that affect the structure and optical properties of the substrate. These obstacles have limited the ability to use pre-processing characterization as a means for improved processing.

One of the main problems arises because the optical absorption of semiconductor materials, such as silicon, is strongly affected by its temperature and doping. For example, a lightly-doped silicon wafer is typically semitransparent at room temperature for wavelengths $>\sim 1.1$ µm. As a result, a typical measurement performed at room temperature at wavelengths greater than about 1.1 µm will be affected by the consequences of light being transmitted through the substrate and reflected from the opposite surface of the wafer. When the wafer is heated in the processing system, the absorption coefficient of the silicon rises very rapidly with temperature and the wafer becomes more opaque. This change leads to large changes in the reflectance and emittance of the wafer. In this case, the room temperature measurement of properties is less useful for improving temperature measurement or control.

The present disclosure is directed to a method and system for determining the optical properties of a substrate, such as a semiconductor wafer, prior to processing the wafer. In accordance with the present invention, various optical properties of the wafer are measured or otherwise determined that can be used not only to assist in making more accurate temperature determinations, but can also be used to control the heating device in a manner that optimizes absorption of thermal energy. Of particular advantage, the information obtained using the methods of the present invention allow for temperature determinations not only at lower temperatures but also at higher temperatures. The methods of the present invention may be carried out outside of the processing chamber prior to processing the wafer. Alternatively, the determinations may also be carried out inside the processing chamber itself.

Figure 3:
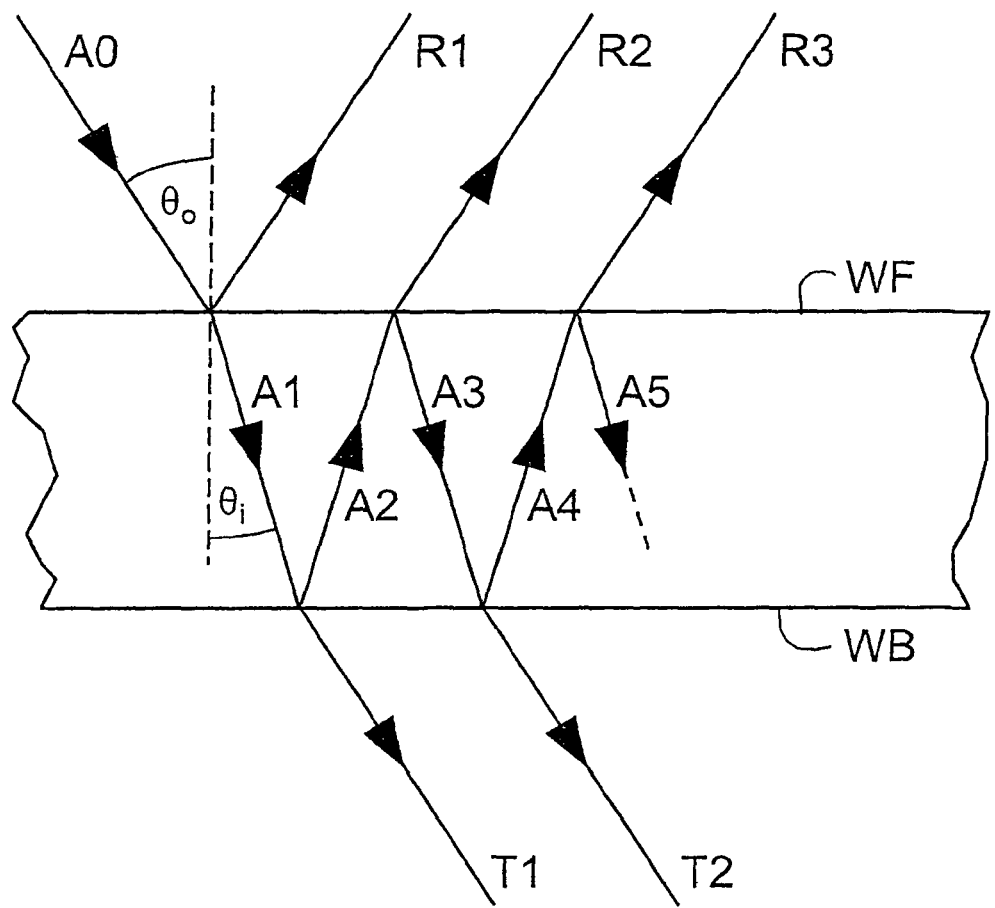
FIG. 3 is a side view illustrating a light beam being emitted onto a substrate, such as a semiconductor wafer.

Prior to discussing the principles of the present invention, a brief description of how a light beam interacts with a substrate may be useful. For example, FIG. 3 shows a representative wafer-like structure that is illuminated by a ray of light, A0, that is incident on its surface at an angle of incidence $\theta_o$. The wafer-like structure may have coatings and device features at its top (WF) and bottom (WB) surfaces, which may affect the reflectivity and transmissivity of these surfaces. Some of the power in the incident ray is reflected at the top surface, forming a reflected ray of light, R1. A second portion of the ray penetrates the front surface (WF), and forms an internal ray, A1. This ray propagates at a different angle, $\theta_i$, as a result of refraction caused by the difference between the refractive index of the wafer and the incident medium that contains ray A0. As the ray A1 propagates through the thickness of the wafer its intensity may be reduced by absorption of energy within the wafer. Typically, this absorption depends on the path length through the wafer through an exponential relationship referred to as Beer's law.

When the ray A1 reaches the back surface of the wafer a portion of it is transmitted through the surface to form a ray T1. A second portion is reflected from the back surface WB and forms a second internal ray, A2. If the back surface WB of the wafer at the point where A1 reaches it is parallel to the front surface of the wafer where A0 was incident, then the ray T1 will propagate in a direction parallel to the original ray A0, provided that the refractive index of the medium beyond the back of the wafer is the same as the medium containing A0. The ray A2 will also be at the same angle to the wafer normal as for A1. The ray A2 will also be attenuated by absorption as it heads back towards the front surface WF of the wafer, where part of it will be transmitted to form a ray R2, and part of it will be reflected to form another internal ray A3.

Internal ray A3 then follows behavior identical to that for A1, returning to the back surface WB of the wafer and generating a second transmitted ray T2, and yet another internal ray A4. A4 then follows the behavior identical to that for A2, returning to the wafer surface and generating an external ray R3, and an internal ray A5. Hence we see that a single ray A0, incident on the surface of the wafer can generate an infinite series of reflected rays such as R1, R2, R3, etc. and an infinite set of transmitted rays T1, T2, etc.

In practice, the finite reflectivity and transmissivity of the surfaces, combined with the finite absorption along the path of each of the internal rays through the substrate thickness, usually lead to a fairly rapid attenuation of the power of the rays as the number of internal reflections rises. However, reflectance measurements can be strongly affected by the degree of light transmission through the substrate, if the measurement apparatus collects energy from rays such as R2 and R3 in addition to the first reflection, R1. Likewise a measurement of transmittance will be affected by collection of the energy in the multiply-reflected rays such as T2, as well as the first ray T1.

Figure 4:
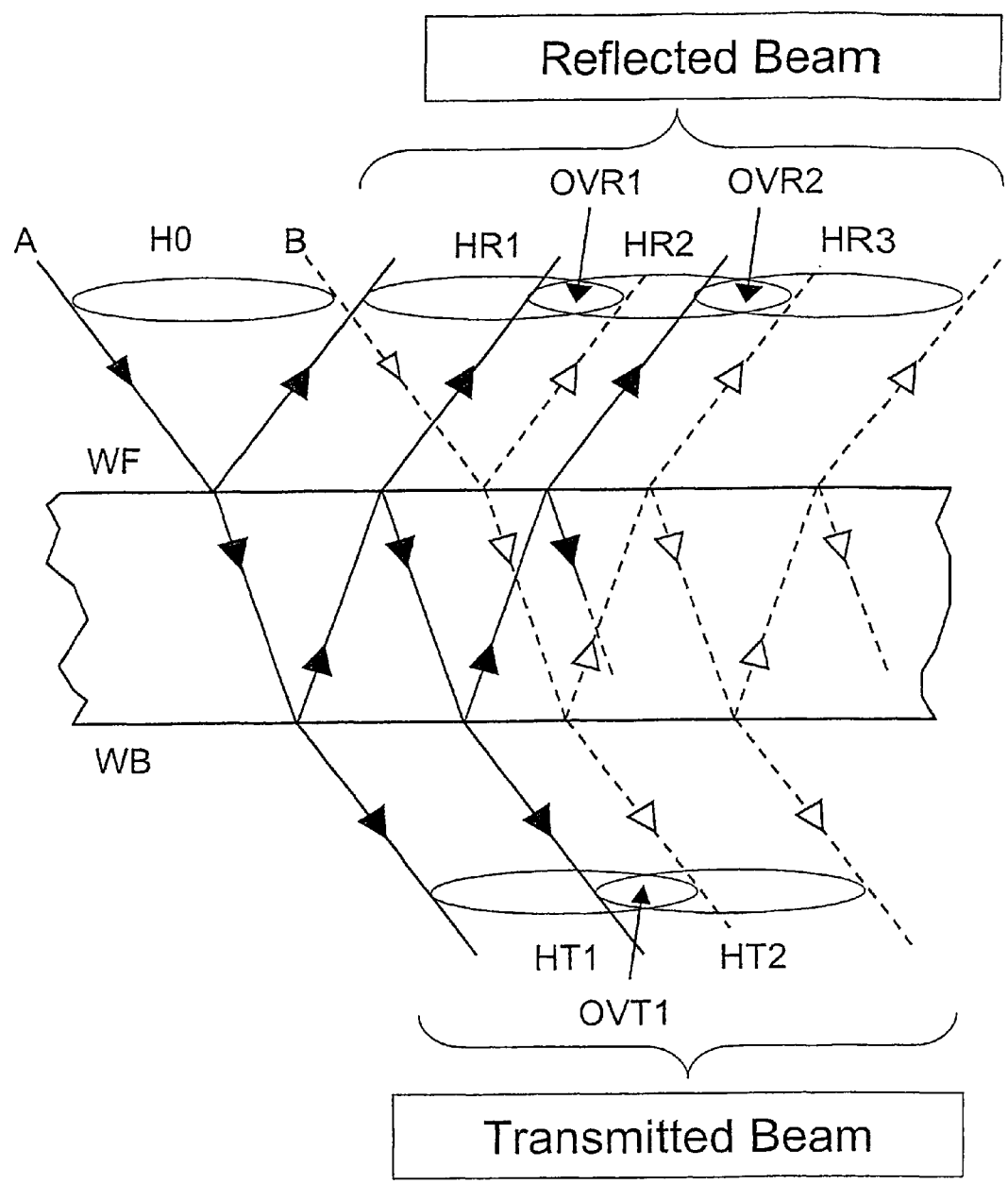
FIG. 4 is a side view illustrating two light beams being emitted onto a substrate such as a semiconductor wafer.

FIG. 4 illustrates the effects of such multiply-reflected rays on a reflectance measurement, in a scenario rather like FIG. 3, except showing the incident beam of light as a collimated beam of light with a finite size, rather than the idealized single ray of FIG. 3.

Two extreme rays A and B are shown to represent the outer limits of the collimated beam of light, H0. The beams of light reflected at the two wafer surfaces (e.g. HR1 and HR2) overlap as shown at OVR1, so that if a light detector were used in an attempt to measure reflectivity, the light collected by the detector would include not only light reflected off the front surface of the wafer, but also light reflected from the back surface of the wafer. Such a measurement would not distinguish between light reflected from the front and from the back of the wafer.

Likewise, the measurement of the transmittance will also result in a measurement that is affected by multiple reflections of light within the substrate, e.g. as a result of overlap OVT1 between beams HT1 and HT2.

The present disclosure is generally directed to a method and system for emitting light onto a substrate, such as a semiconductor wafer and separating through various means the amount of light reflected from the front surface of the wafer from the amount of light reflected from the back surface of the wafer. Once the light is separated, accurate measurements of the reflectivity of each surface can be conducted. The present inventor has found that this information can be useful in controlling at least one parameter in a processing chamber when the wafer is later processed as will be described in greater detail below.

Figure 5:
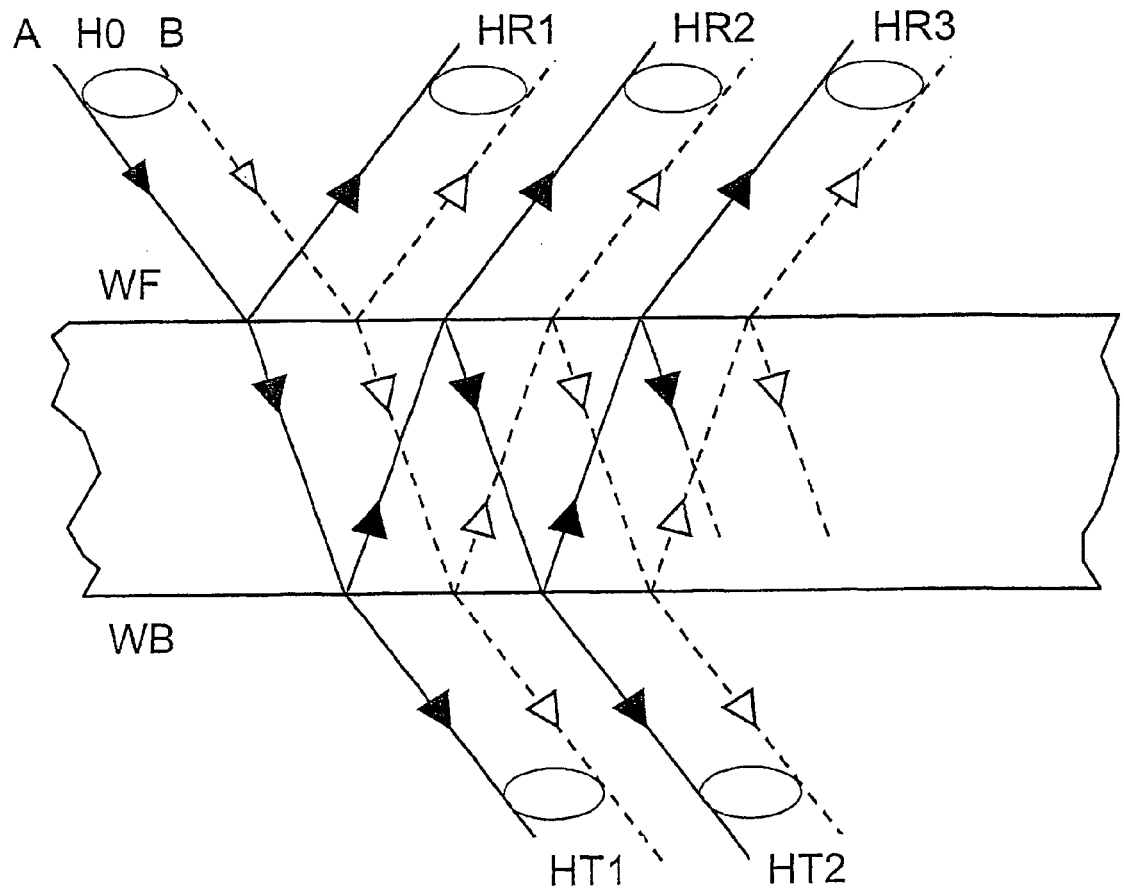
FIG. 5 is a side view illustrating another embodiment of two light beams being emitted onto a substrate such as a semiconductor wafer.

For example, referring to FIG. 5, one embodiment of an approach for eliminating the effect of multiple reflections is illustrated. In this case, the size of the incident beam of light, H0, and the angle-of-incidence on the substrate have been selected to separate the beams of light reflected from the different surfaces (HR1, HR2, HR3 etc.). The locations where the incident beam of light is reflected from the front (HR1) of the substrate and the location where the light reflected from the back surface of the substrate (HR2) reaches the front surface do not overlap. As a result, there are several beams of reflected light, which are spatially separated. The light in these beams can fall on different detectors, or on an array of sensors. The intensity of the light reflected in the first reflection of the incident beam is only affected by the reflectivity of the front surface of the substrate, whereas that in the second reflected beam is affected by the reflectivity of both the front and the back of the substrate as well as the absorption coefficient of the substrate.

In some cases only the reflectivity of the front surface may be of interest, but by collecting the light in separate beams it is possible to analyze the optical properties of the wafer more completely. For example, by collecting two beams of reflected light, information can be deduced about both surfaces of the wafer, and/or about the absorption coefficient of the wafer. Similar benefits can apply to analysis of the different components of transmitted light, HT1, HT2, etc., shown in FIG. 5. Furthermore, by making separate measurements with light incident from either the front or back of the wafer, even more information can be obtained and/or the magnitude of errors in the estimates of optical properties of the wafer can be reduced.

When carrying out the method as shown in FIG. 5, the one or more detectors used may comprise any suitable device capable of measuring the intensity of a light beam at a particular wavelength or at a range of wavelengths.

Despite the advantages of using the configurations of FIG. 5, in some embodiments, it may be difficult to implement for all types of substrates, especially for those that are relatively thin and where the refractive index is relatively large. In such circumstances, the distance between the position where the incident beam of light impinges on the top surface and the position where the beam of light reflected from the back of the substrate impinges on the top surface may be quite small, leading to the need for a very small incident beam of light. However, laser light sources may be used to provide higher intensity illumination for narrow beams of light.

In another embodiment, various techniques may be used in order to determine and differentiate the amount of light reflected off the front surface of the wafer versus the amount of light reflected off the back surface of the wafer, even in cases where the reflected beams partially overlap. For example, as long as the overlap of light is only partial, the degree of overlap may be calculated from geometrical calculations. Further, the conditions of the overlap can be varied by changing the size or shape of the incident beam or the angle of incidence, which will allow for a determination of the amount of light being reflected off the front surface. For example, changing the angle of incidence of the collimated beam of light HO may alter reflectivity and the path length through the substrate. In one particular embodiment, for instance, in one condition the detected reflected light off the substrate may include all the reflected components R1, R2, R3, etc. as shown in, for instance, FIG. 3. In a second condition by altering the angle of incidence, there may be no overlap in the components of the reflected beams. Similar techniques may then be used for analysis of the transmitted light as well.

In other embodiments, instead of or in addition to manipulating the light source for separating the different light components, an optical pathway may be devised that is configured to separate the different light components. Once the different light components are separated, any of the light components can be detected or measured to the exclusion of the other light components. For example, in one embodiment, light reflected from the top surface of a substrate may be separated from light being reflected from the bottom surface of the substrate. The amount of light reflected from the top surface and/or the amount of light reflected from the bottom surface may be detected for determining various properties of the substrate. For instance, light reflected from the top surface and light reflected from the bottom surface of the substrate each provide information about various characteristics of the substrate.

Figure 6:
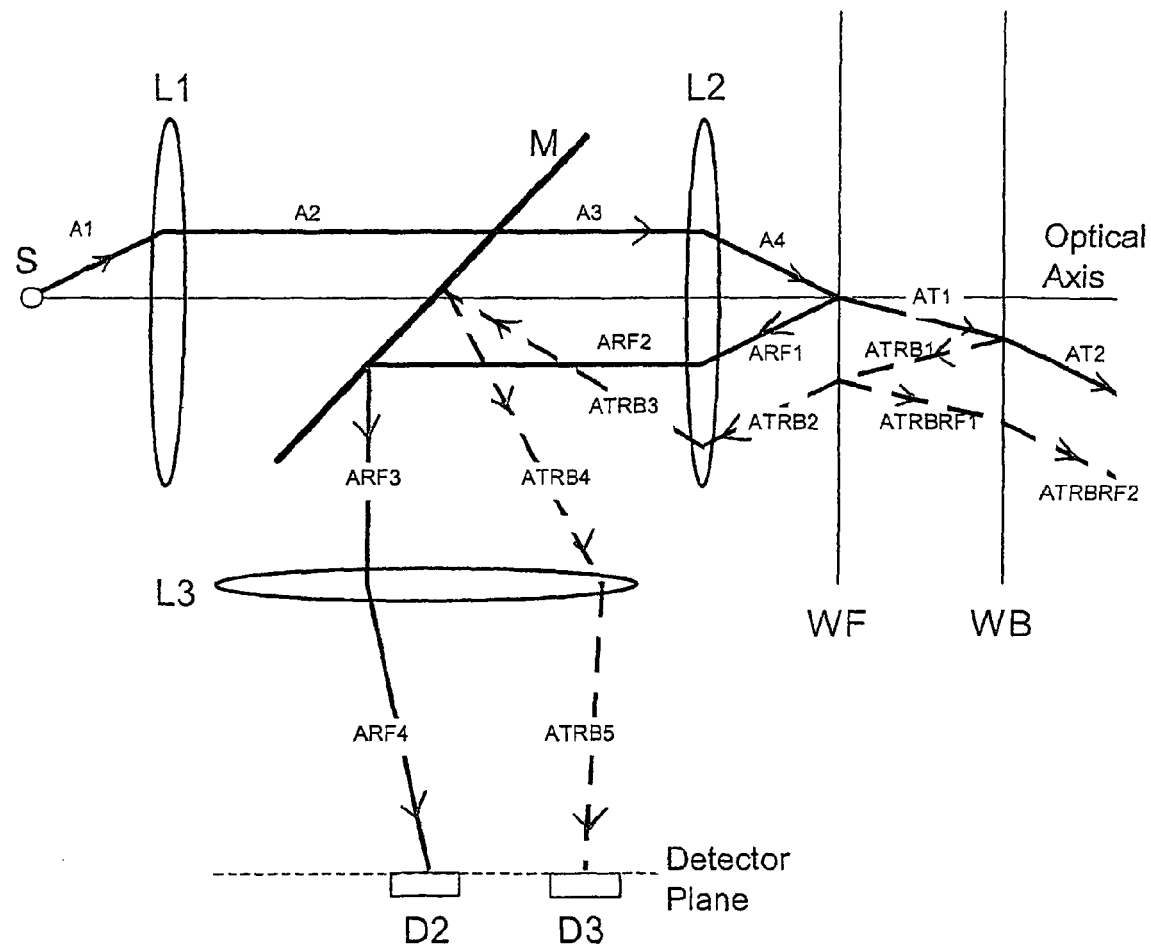
FIG. 6 is a side view of one embodiment of an optical pathway that may be used in accordance with the present invention.

For example, FIG. 6 illustrates an alternative approach for discriminating between light reflected from the top surface and the bottom surface of a wafer-like substrate. As shown, a ray of light from a light source, S, is propagated through an optical pathway that includes lenses and mirrors. Ray A1 is emitted by S and then collected by the lens L1 that forms a collimated beam, represented by the ray A2. A2 passes through a mirror M and continues as ray A3. L2 is a lens that focuses the light, forming the ray A4 that impinges on the front surface of the wafer WF.

Part of the ray A4 is reflected from WF, forming the ray ARF1. ARF1 is collected by the lens L2, which recollimates it to form the ray ARF2. The ray ARF2 is reflected from the mirror M forming the ray ARF3. ARF3 is collected by the lens L3, which focuses it, forming the ray ARF4, which impinges on a detector D2.

A second part of the ray A4 is transmitted through the surface WF of the wafer, forming an internal ray AT1. Part of AT1 is transmitted through the back surface of the wafer, forming a transmitted ray AT2. A second part of AT1 is reflected from back surface WB, forming the internal ray ATRB1. Part of ATRB1 is then reflected at the front surface forming the internal ray ATRBRF1. ATRBFR1 then propagates to the back surface, and some of it is transmitted through back surface of the wafer WB, forming a second transmitted ray ATRBRF2. A second portion of ATRBRF1 (not shown) will also be reflected at WB, to form the infinite series of internal rays, as was discussed above. Part of ray ATRB1 is transmitted through the front surface WF, to form a second reflected ray ATRB2.

If both ray ARF1 and ATRB2 are collected by the optics of the reflected light measurement system and arrive at the same detector element, then the reflectivity of the back surface of the wafer will influence the reflectance measurement.

ATRB2 is collected by lens L2 and focused to form the ray ATRB3, which is reflected by the mirror M to form ATRB4, which is focused by lens L3 to impinge on a detector D3 as ATRB5.

If D2 and D3 are separate detectors then it is possible to discriminate between the two reflected rays. In this case the measurement from detector D2 represents reflection from only the front surface of the wafer. The measurement from detector D3 may also be useful for analysis of the properties of the wafer, because its intensity is affected by the absorption of light within the wafer, by the transmissivity of WF, and by the internal reflection from WB.

Figure 7:
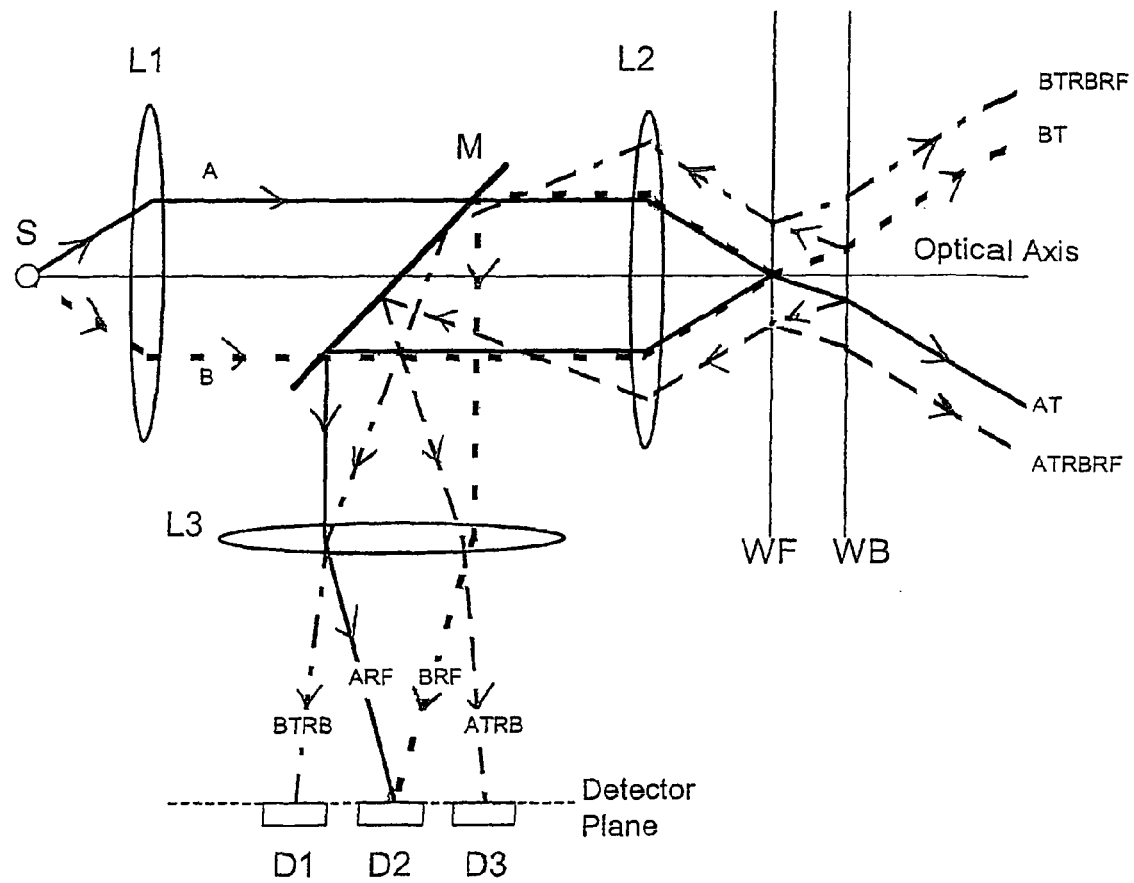
FIG. 7 is a side view of another embodiment of an optical pathway that may be used in accordance with the present invention.

In some systems, the source S may emit light over a range of angles. Although it may be possible to restrict the range of angles of incidence through the use of apertures, this can result in loss of signal strength for the measurement since the intensity of light is reduced. The behavior of rays that propagate through the optical system may be analyzed at different angles to the optical axis. FIG. 7 illustrates the behavior of two rays emitted from S as they pass through the same optical system as considered in FIG. 6. In this case ray A and ray B are emitted at the same angle to the optical axis, but they are on opposite sides of the axis. Their behavior is symmetrical about the axis. Rays ARF and BRF represent the two rays that are reflected from the front of the wafer surface, and it can be seen that they both end up at the same point in the detector plane. This is because the optics were selected so that an image of the source, S would be recreated in the plane of the detector, after reflection from the front surface of the wafer. In this example, this meant that the focal length of L1 was chosen to match the distance between S and L1, and the focal length of L2 matched the distance between L2 and the front surface of the wafer, and the focal length of lens L3 matched the distance between L3 and the detector D2.

The condition that the source, S, is imaged onto the detector plane via reflection from the front surface of the wafer, WF, ensures that the energy from the source is efficiently transferred to a small region of the detector plane, where detector D2 is located. In the embodiment shown in FIG. 7, the two rays ARF and BRF converge to the same point on detector D2, because they originate from the same point on source S. In this embodiment, that point on source S is on the optical axis, but the same would be true for any point in the plane of S. The rays that are reflected from the back of the wafer BTRB and ATRB, on the other hand, reach the plane of detector D2 at different locations. If desired, they can be detected with detectors D1 and D3. As described above, the rays that are reflected from the back of the wafer BTRB and ATRB can also provide useful information regarding the optical characteristics of the substrate. Thus, in certain embodiments, one may only be interested in detecting the rays that are reflected off the front of the substrate, while in other embodiments one may only be interested in detecting the rays being reflected off of the back of the substrate. Of course, in still other embodiments, the rays being reflected off the front of the substrate and the rays being reflected off the back of the substrate may each be individually measured.

Figure 8:
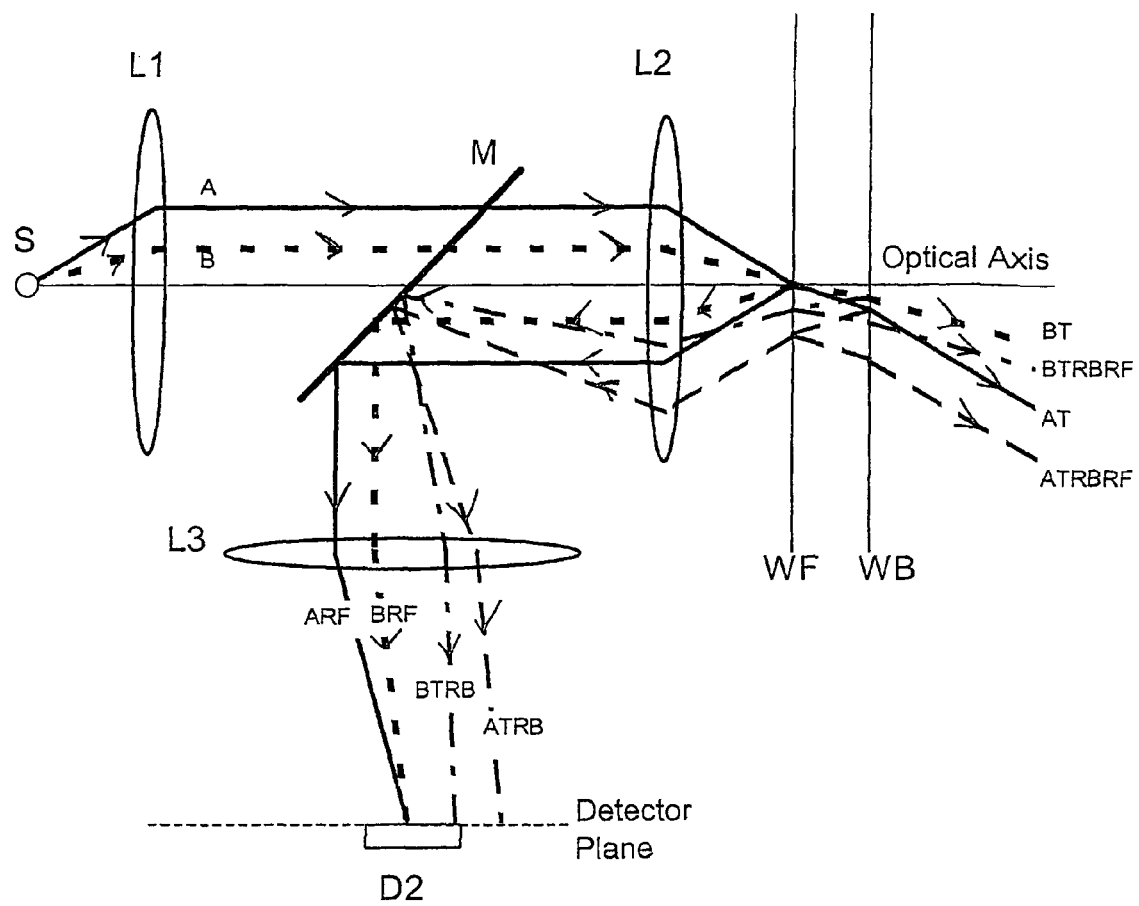
FIG. 8 is a side view of another embodiment of an optical pathway that may be used in accordance with the present invention.

Another optical pathway that may be used in accordance with the method of the present invention is shown in FIG. 8. The optical pathway illustrated in FIG. 8 is similar to the optical pathway illustrated in FIG. 7. In this embodiment, however, the two rays A and B are emitted from the source S at different angles to the optical axis. Once again the rays that were reflected from the front surface of the wafer, ARF and BRF arrive at the same point on the detector D2. However the two rays reflected from the back of the wafer ATRB and BTRB, arrive at different locations, and only BTRB lands on the detector D2. This illustrates as a general point about the relative impact of rays reflected from the front of the wafer or the back of the wafer on the signal detected by detector D2. The energy that is reflected from the back surface of the wafer, WB, may end up being distributed over a larger area in the plane of the detector than the energy reflected from the front of the wafer WF. As a result, the relative contribution of energy reflected from the back of the wafer to the signal from the detector D2 is smaller than that from the reflection from the front of the wafer. The reason for this is because the optics were selected so that an image of the wafer surface WF is formed at the plane of the detector. Since the rays reflected from the back of the wafer WB are not imaged at the detector plane, the distribution of energy is more spread out.

Figure 9:
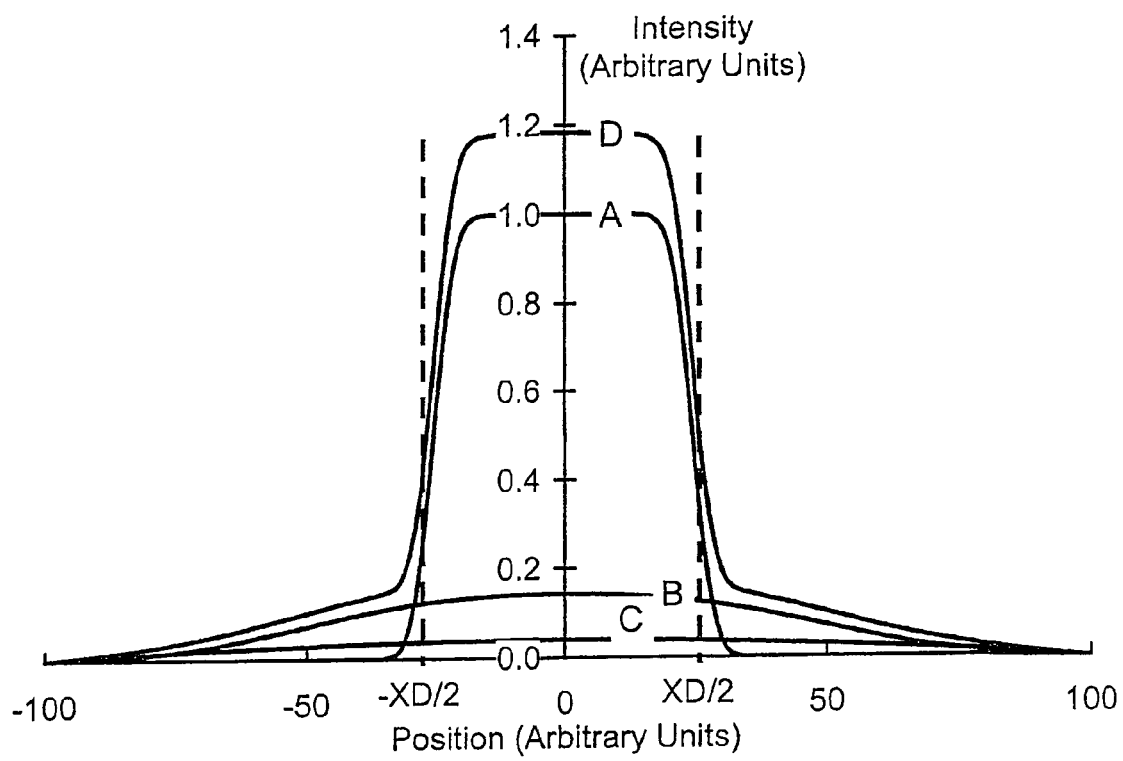
FIG. 9 is a graph illustrating light intensity based on position as will be described in more detail below.

This principle of discriminating between the energy reflected from the back of the wafer and that from the front of the wafer by selecting the optical conditions to optimize the energy density landing on the detector is illustrated in FIG. 9. The curve A illustrates the power density distribution in the plane of the detector for light that has been reflected from the front surface of the wafer. Curve B shows the corresponding distribution for light that has been reflected from the back of the wafer. Curve C, is that for light that has undergone more than one reflection at the back surface, and curve D is the intensity sum from curves A, B and C. If we consider that portion of light represented by curve D that falls between the axis positions −XD/2 and +XD/2 as being the energy detected by a detector, we can see that the contribution of signal from curve A is much larger than that from curve B or C.

As shown in FIGS. 6-8, various optical pathways may be used and adjusted in order to separate the different light components and/or to otherwise control the contribution of the light signal from the front reflection or the back reflection. Further, other techniques and optical elements may be added to the optical pathway for facilitating separation of the different components. For example, apertures or light filters may be incorporated into the optical pathway for blocking light where desired.

Figure 10:
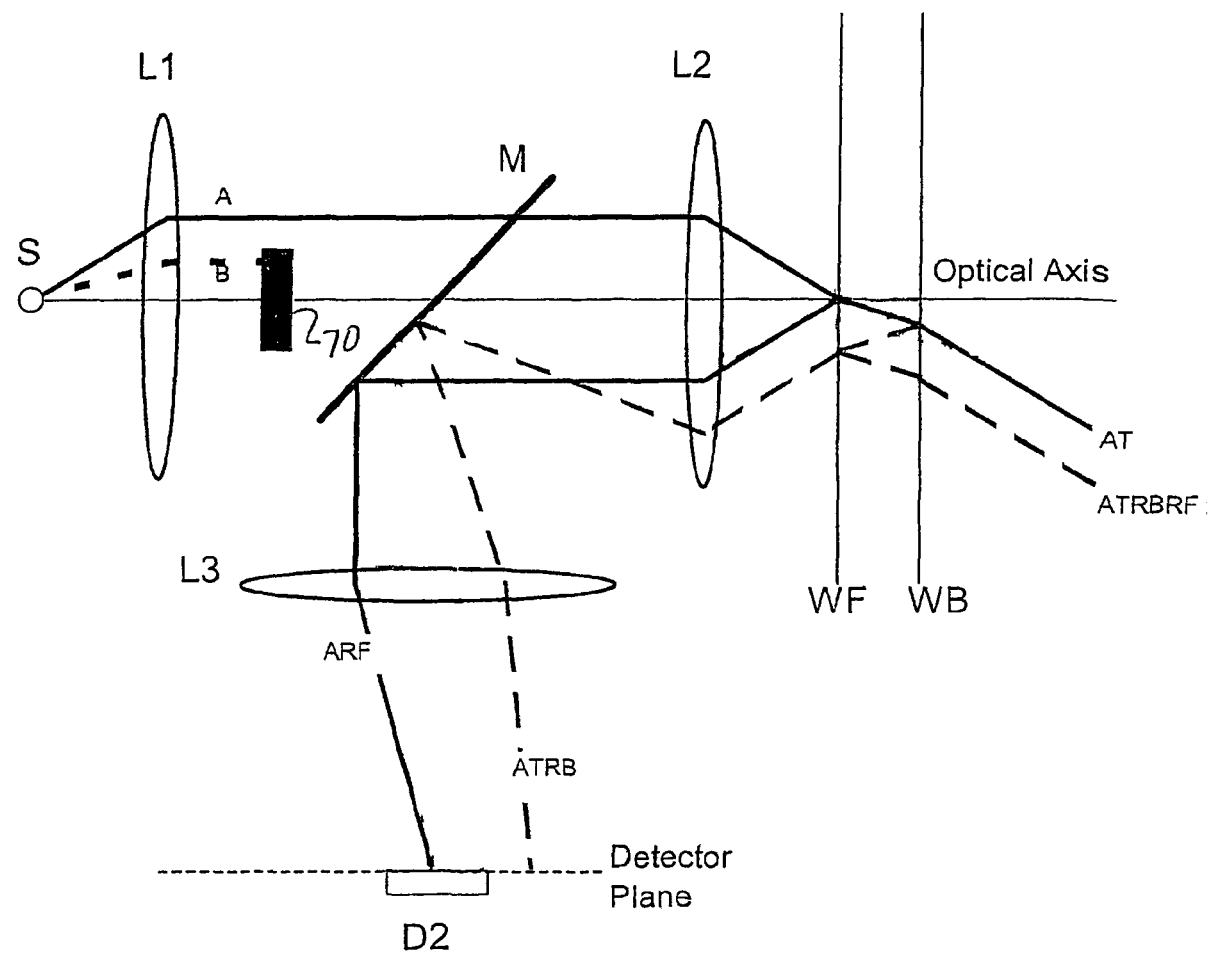
FIG. 10 is a side view of still another embodiment of an optical pathway that may be used in accordance with the present invention.

For example, referring to FIG. 10, one embodiment of an optical pathway that uses a blocking element 70 is shown. In this embodiment, the blocking element 70 is used to block light ray B and rays with smaller inclinations to the axis. In this manner, the detector D2 only receives rays that have been reflected from the front surface WF of the semiconductor wafer.

Such blocking elements, that control the distribution of angles of incidence at the wafer surface may also be positioned elsewhere, either in the incident beam or in the reflected beam, so long as their effect is to block those rays that have been reflected from the back of the wafer and are still capable of landing on the detector of interest. Control of the distribution of angles of incidence may also be useful if it is desirable to match the measured reflectance to a specific angle of incidence or range of angles of incidence. In some embodiments, it is also possible to vary the range of angles of incidence by an adjustable blocking element and take measurements of the reflected light signal at different settings. These kinds of measurements can assist in characterizing the optical properties of the sample, for example by characterizing the degree of absorption within the wafer.

Optical pathways made in accordance with the present invention may include a single blocking element 70 as shown in FIG. 10 or multiple blocking elements depending upon the particular application. It should be understood that a blocking element may be included in the optical pathway as a separate component as shown in FIG. 10 or may be incorporated into one of the other optical elements. For example, the limited diameter of a lens, mirror, or other optical element can act as a blocking element as used herein, when these elements can limit the spatial extent of rays that propagate through the optical system and reach the detector.

The blocking element 70 can be any suitable device capable of eliminating any unwanted rays of light. In one embodiment, for instance, the blocking element may comprise a device that includes an aperture for only allowing selected light rays to pass. As described above, however, a lens, filter, mirror or other optical element may also be used.

Figure 11:
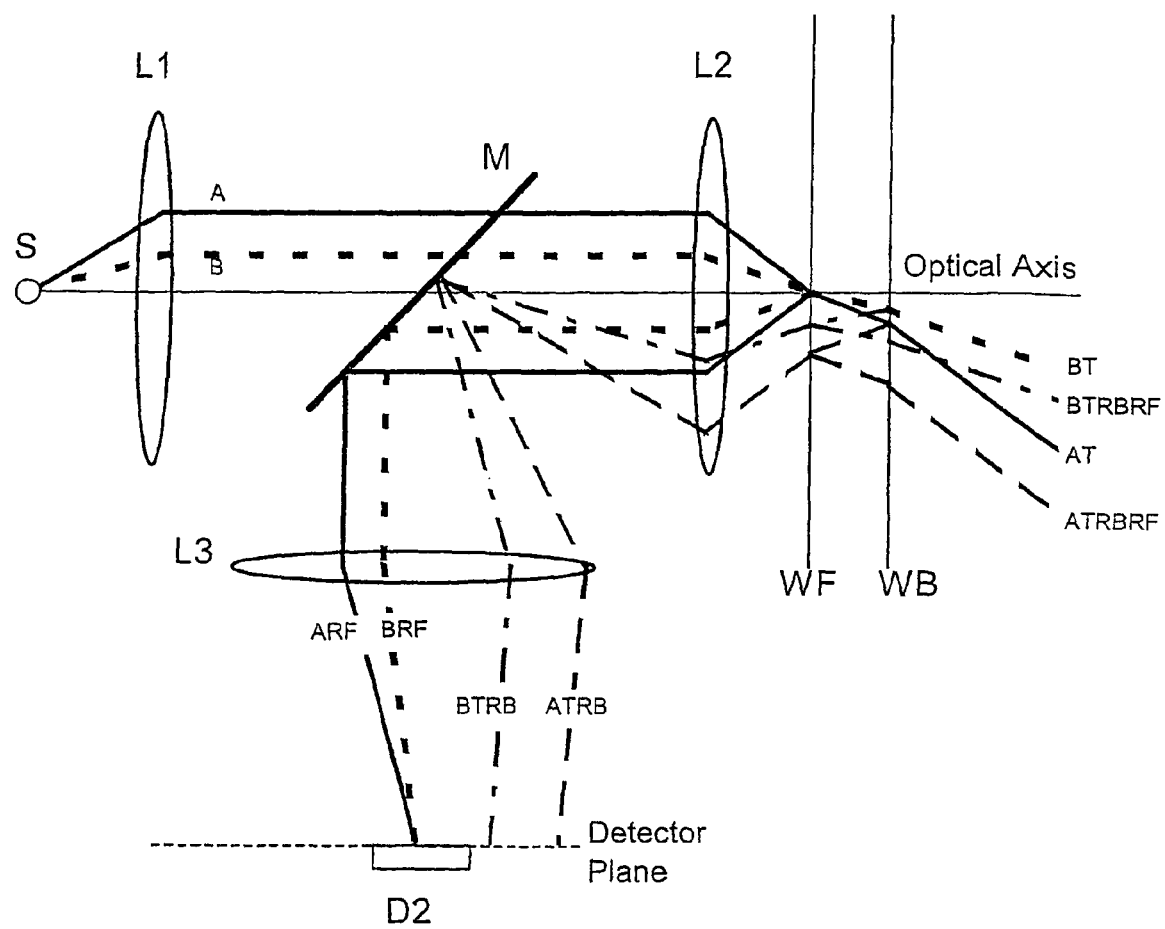
FIG. 11 is a side view of another embodiment of an optical pathway that may be used in accordance with the present invention.

Another approach for controlling the ratio of the energy reflected from the front surface WF to that reflected from the back surface WB involves optimizing the focal lengths of the lenses, especially lenses L2 and L3. The ratio of the focal lengths of these lenses controls the magnification of the intermediate image of S that is formed at the front surface WF when it is reimaged at the detector plane D2. By decreasing the focal length of lens L2 relative to that of lens L3, the magnification can be increased. This has the effect of increasing the ability to discriminate between reflection from the front and the back. FIG. 11 illustrates the point, since in this case we see that ray BTRB no longer falls on the detector D2, showing improved discrimination against light reflected from the back of the wafer as compared to the example in FIG. 8 where BTRB lands on the detector.

In one embodiment, as shown in FIG. 11, the different light components can be separated out by decreasing the depth of focus. In the embodiments shown in FIGS. 7 and 8, the front of the wafer, WF is at the focal point of lens L2, and the detector is at the focal point of L3. The depth of focus of L2 depends on a number of factors including the focal length and the angle of the illumination. If the conditions are set so that lens L2 and lens L3 only form an image at the detector plane for the set of rays that predominantly emanate from a narrow range of positions around the surface WF, then the depth of focus is limited to a region near the surface of the wafer. By ensuring that the back of the wafer WB lies outside the depth of focus, the rays reflected from the front and the back of the wafer may be separated, because the majority of radiation that reaches the detector has been reflected from the top surface of the wafer.

In some embodiments, a relatively large range of angles of incidence in the incident beam may be used. This condition may also be more representative of the range of angles-of-incidence for the heating radiation incident on the wafer within the process chamber, providing a second benefit of this measurement approach. In this manner, one can evaluate the way in which the heating radiation impinges on the wafer in the chamber by optical modeling, for example by the use of ray-tracing software. A proper understanding of the range of angles of incidence of the heating radiation can then be used to match the illumination conditions used within the measurement system to those that apply in the processing equipment.

In some cases, the reflected light can be collected from a rather small region on the wafer surface, to prevent the collection of light that has propagated to the back surface of the wafer and been re-reflected toward the surface. The size of the region from which reflected light is collected is determined by the optics used, the size of the detector and any apertures, filters or other optical elements included. The optimal size for the area analyzed partly depends on the thickness of the sample, since if the sample is very thin it is more difficult to separate rays from front and rear surface reflections if light is selected from a large area on the wafer surface. However, there may be other factors to consider. For example, if a surface of the wafer is patterned, then the reflectivity may vary within the region from which reflected light is collected. This may be advantageous if it desired to collect average properties of the region.

For instance, in one embodiment, the size of the region on the wafer surface from which the reflected light is collected can be relatively small and can be designed to match an area viewed by a temperature measuring device, such as a pyrometer. In other words, the field of view of the pyrometer can match the area from which the reflected light is collected. In other embodiments, however, light can be collected from a relatively large region on the wafer surface. Collecting reflected light data from a relatively large area may be useful when optimizing power coupling between a heating device and the substrate. On the other hand, if the substrate is being heated by an energy beam, the area that is optically characterized can be matched to the area irradiated by the energy beam. Such an approach may be especially useful for characterizing and optimizing coupling of energy from laser beams. This could be especially useful for lasers that emit energy at wavelengths greater than ~1 µm, where semiconductor substrates are frequently semi-transparent. For example, such lasers include diode lasers, YAG lasers, fiber lasers, CO and $CO_2$ lasers.

In one particular embodiment, the light source may be scanned across the substrate. Information can then be sequentially collected about the reflected light intensity. Scanning may occur by moving a light source, moving the optical pathway, and/or by moving the substrate itself. In this manner, information can be collected at any particular location on the substrate. Alternatively, an average may be collected across the area of the wafer.

In one embodiment, a microscope objective lens may be used in order to provide a short focal length lens. The lens may be placed anywhere in the optical pathway, such as at the lens L2 as shown in FIG. 11. When positioned at lens L2, the microscope objective lens may be used to focus the radiation onto the wafer surface. Such lenses can have small focal lengths and high numerical apertures. As a result they provide a convenient approach for providing an optical system that illuminates the wafer with a large range of angles of incidence and collects light with a small depth of focus, especially when the resulting magnification of the wafer surface is relatively large (e.g. the optical system has a magnification greater than ×10, such as greater than ×50). However many alternative approaches can be considered, including optics that are larger and further from the wafer surface, so long as it is ensured that the light is collected only from the desired region and that the majority of the collected radiation has only been reflected at the first surface. The optical axis of the measurement system also need not be normal to the wafer surface.

Analysis of the distribution of light in the plane of the detector is possible by scanning a detector in this plane, or through the use of various sizes of detector, or variable or scanning apertures in the plane of the detector, or by employing an imaging detector such as a charge-coupled device (CCD) camera, or an array of detectors. The information about the spatial distribution of the light at the plane of the detector can be used to refine the measurements. For example, if the thickness of the substrate is known or if it is measured, then it is possible to interpret the shape of the intensity distribution with respect to components that are reflected from the front surface or the back surface of the wafer. An algorithm can be used to split the detected distribution into a component that is reflected from the front surface, as opposed to other components that originate from multiple reflections within the substrate. Hence, as suggested in FIG. 9, components reflected from the back surface can be mathematically subtracted from the total signal, to yield a more accurate estimate of the signal reflected from the front surface of the wafer.

Figure 12:
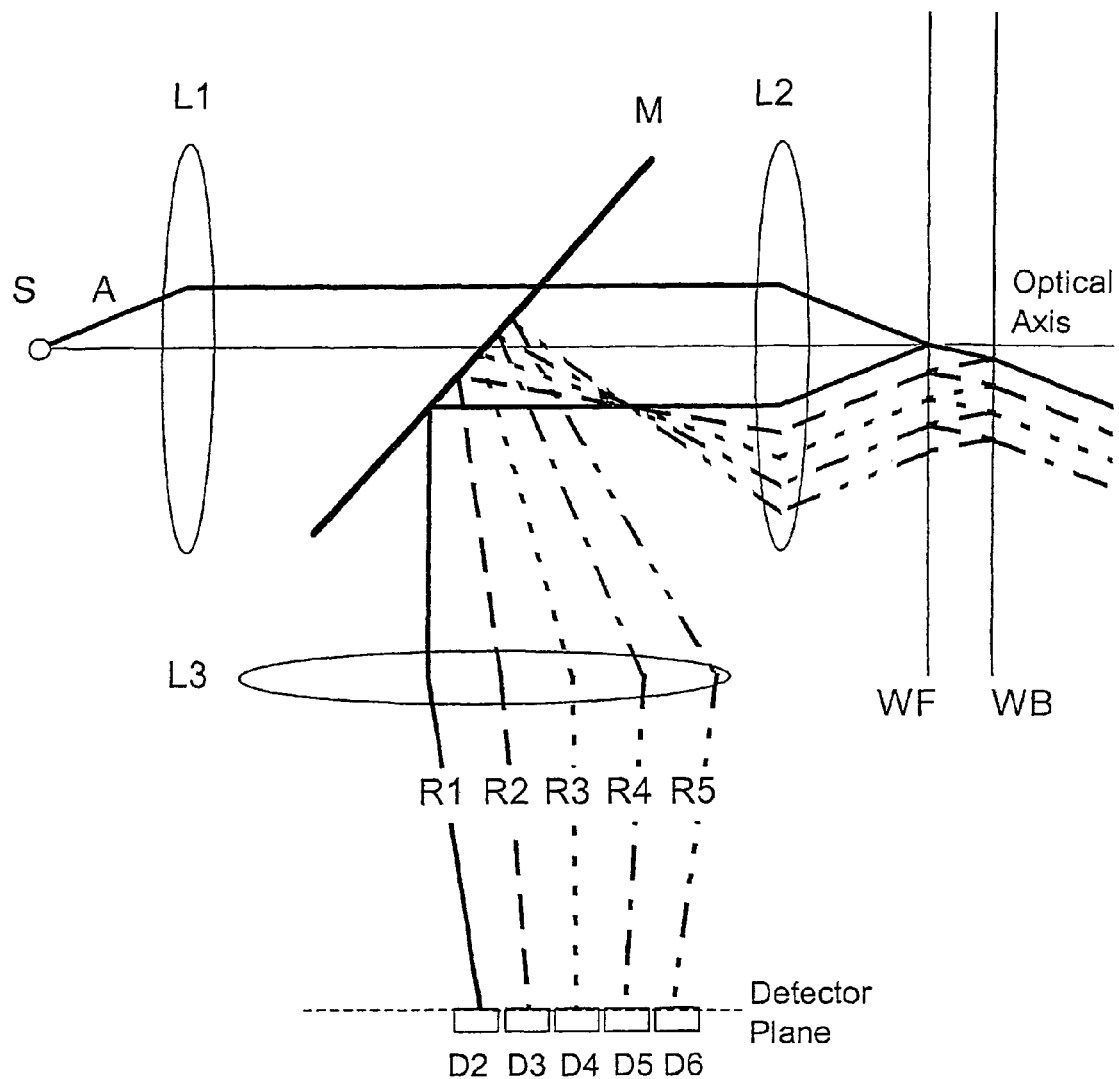
FIG. 12 is a side view of yet another optical pathway that may be used in accordance with the present invention.

In FIGS. 5-8 and 10-11, the focus has primarily been on differentiating the amount of light reflected from the front surface of the wafer as opposed to light reflected from the back surface. As mentioned above, there is actually an infinite series of reflected rays. FIG. 12 illustrates how a single ray, A, from the source S propagates through the optical system described before. In this case the figure shows the path of the ray R1, that is reflected from the front of the wafer, WF, ray R2, which arises from one reflection at the back surface WB, as well as R3, R4 and R5, which arise from two, three and four reflections at the back surface, respectively. In principle there an infinite number rays in the series, but as mentioned above, the intensity of rays decreases rather quickly because of energy losses. The rays R1, R2, R3, R4 and R5 arrive at detectors D2, D3, D4, D5, and D6 respectively. It is possible to measure the intensities of each of these rays in order to better characterize the optical properties of the wafer. When it is desirable to measure the rays R1, R2, R3, R4 and R5, for instance, the light source S may be a laser source in order to generate a sufficient intensity for the measurements to occur.

For a source emitting rays across a range of angles of incidence there will be many rays falling on each of the detector elements, leading to a family of curves such as B & C shown in FIG. 9. Analysis of the distribution of intensities may help to identify the components as described above, and such approaches can be combined with the use of apertures or other optical elements that can restrict the range of angles that propagate and hence the families of reflected light components that can reach the detector.

Figure 13:
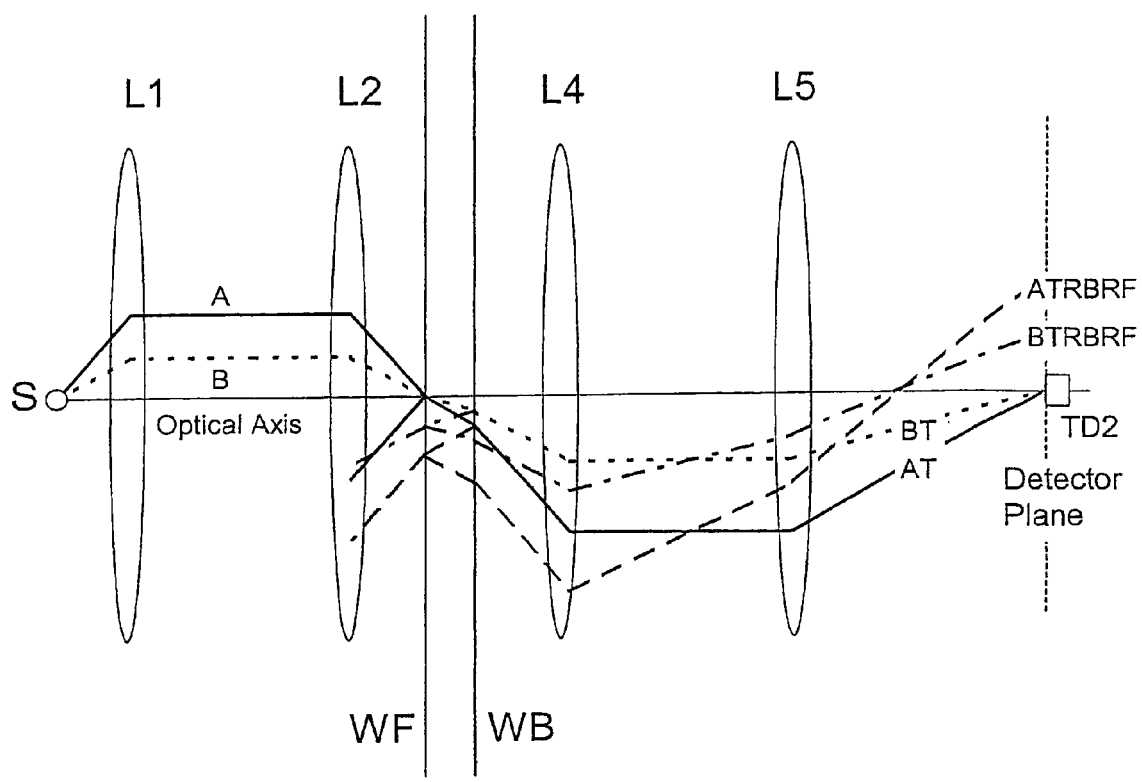
FIG. 13 is a side view of another embodiment of an optical pathway that may be used in accordance with the present invention.

The principles described with respect to analysis of reflected light can also be applied to analysis of the light transmitted through the substrate. FIG. 13, for instance, shows one embodiment of two rays A and B propagating from a source S through an optical pathway, where lenses L1 and L2 serve much as before to form an image of a light source S at the wafer surface, WF, and lenses L4 and L5 reimage the image of S at WF to the plane of a detector TD2. The design ensures that the transmitted rays that are not reflected from the back of the wafer, TA and TB, are brought to focus at the plane of TD2. The rays that have undergone at least one reflection at the back surface of the wafer, such as ATRBRF and BTRBRF arrive at different locations in the plane of the detector. Hence in a manner rather analogous to that for the reflected rays, it is possible to decrease the contribution of multiply reflected rays to the signal detected by TD2.

Figure 14:
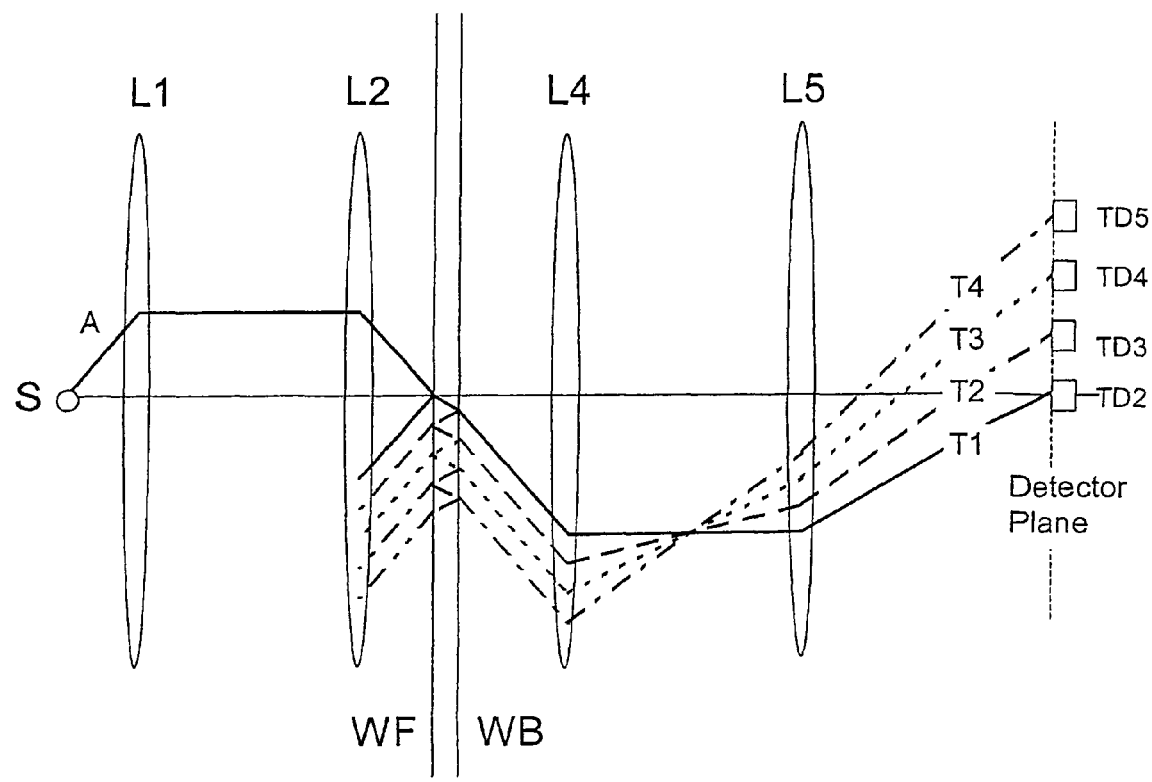
FIG. 14 is a side view of another embodiment of an optical pathway that may be used in accordance with the present invention.

FIG. 14 shows the behavior of a single ray A, that is transmitted through the optical system and the wafer, generating multiple transmitted rays, in a fashion rather analogous to that of the multiply reflected rays illustrated in FIG. 12. Such rays may also be detected by an array of detectors if desired, and similar analysis methods used to analyze the spatial distribution of transmitted light to those discussed in the context of the spatial distribution of reflected light.

It should be noted that although the illustrations here show the use of two lenses between the source and the wafer, the general principles can be achieved with a wide variety of alternative optical pathways using either more or fewer lenses, or indeed by substituting mirrors, such as curved mirrors or other optical elements for some or all of the lenses. Optics that control the state of polarization of the incident or reflected light can also be included in the apparatus if needed. Such optics can include polarizers and retarders, such as quarter, half or full wave-plates, or other optical elements that can produce radiation of a desired state of polarization, including plane polarization, elliptical or circular polarization.

When configuring the state of polarization and/or configuring the angle of incidence, it should be noted that these factors should be taken into account for any given measurement arrangement. For normal incidence and near-normal incidence (e.g., light which is incident at angles of incidence less than about 25°) the effects are usually quite small. In the case of non-normal incidence, it is often useful to perform measurements with the incident radiation polarized in either the s-plane or p-plane. Measurements for both conditions can allow for a full determination of the optical properties of the substrate. Ellipsometric measurements may also be performed at various times, such as during low temperature pre-characterization of the substrate.

The measurements can be made at any wavelength of interest, or they can be performed across a spectrum, through the attachment of appropriate spectrocopic apparatus such as a monochromator or other wavelength-selective filtering elements. Measurements of integrated properties can also be performed by using a broad-band energy source and collecting all the radiation reflected at a detector with a broad wavelength response.

The light source S that is used to emit light onto the semiconductor wafer can be any suitable light emitting device. The light source, for instance, may emit light at a range of wavelengths or at a specific wavelength. Suitable light sources may include W-halogen light bulbs, Xe-arc lamps, discharge lamps, light emitting diodes, lasers, or thermal sources such as black-body cavities, glowbars or other thermal radiation emitting elements. In some cases it would be useful to set the lamp radiation sources at so that they emit spectra representative of the energy source used in the processing apparatus. One way to do this is to characterize the radiation source of interest and combine it with wavelength filtering elements that can mimic the energy source in the processing equipment.

In one embodiment, the light source may comprise a super-continuum light source. A super-continuum light source possesses some special advantages for rapid measurement of wafer optical properties, since it is far brighter than a conventional broad-band light source such as a tungsten-halogen lamp or an LED. This can be useful for performing very fast measurements, since the energy delivered in a given time is much larger, allowing higher signal levels for detection of reflected, transmitted or scattered light. It can also be useful if there is a relatively high level of stray background radiation that may interfere with accurate measurement of wafer properties, since a very bright illumination can make light from such stray light sources insignificant as compared to that from the super-continuum light source. This can have special advantages for measurements of optical or thermal properties of a wafer in a processing chamber, especially if the wafer is hot or if there is stray radiation being emitted by heating elements, lamps, lasers or plasma. A very bright radiation source also allows the use of compact optics, since a large amount of radiation may be delivered from a small emitting area and it can be conveniently coupled to fibre-optics, light pipes and other elements that can be conveniently introduced into a processing equipment and chambers. The super-continuum light source can also produce a spectrum that is relatively flat, i.e. that does not vary by a great deal over a wide wavelength range. This has the advantage of extending the wavelength range that is conveniently covered by the light source and simplifying the interpretation of spectral measurements such as reflection and transmission spectra.

The super-continuum light is generated by exposing a non-linear medium to high power radiation. For example it can be generated by applying a high power pulse of radiation from a laser to a water cell and collecting the spectrum of emitted light. An efficient approach involves using a photonic crystal fibres or tapered fibres. Super-continuum light sources can generate spectra of light covering wavelength ranges that are useful for characterizing semiconductor wafers. For example, the KOHERAS SuperK™ White super-continuum source from KOHERAS A/S (Birkerød, Denmark) produces a spectrum of radiation with a power spectral density >4 mW/nm between 460 nm and 2000 nm. Such light sources can be of special interest for measuring wafer transmission or reflection within the process chamber. The measurements can be used to deduce the temperature of the wafer. Furthermore, the light source may be used for a variety of other measurements, either directly or in combination with wavelength-selective filtering elements. Such elements can select the wavelengths of light delivered to the wafer, or light that is collected from the wafer after reflection, scattering, transmission or emission from the wafer. Measurements can include reflection and transmission as mentioned above, but they can also include methods where the light reaching the wafer is modulated and it creates a thermal or electronic modulation of the wafer's properties. Such a modulation can be detected and used to extract information about the wafer.

Furthermore, such light sources may even be useful for thermal processing, especially for the case where the wafer has a pattern of coatings on it. In this case, the use of a broad spectrum for heating can reduce the degree of variation in the power absorbed by different regions of the pattern, hence providing more uniform processing.

When thermal energy sources are used, it may be useful to set their temperatures to be representative of the wafer temperature under the real processing conditions. If necessary the latter could be set to match the wafer temperature on a recipe-by-recipe basis. For example if the key process step occurs at 1000° C., then the thermal source may be at that temperature. For these cases, where broadband radiation sources are used, it can be convenient to use a broadband detector such as a thermopile, a bolometer or a pyroelectric device to detect the reflected radiation. Differences between the conditions that apply within the processing chamber and within the measurement apparatus can be compensated for by calibration procedures. If the processing equipment uses a laser for heating the wafer, it may be necessary to make the optical measurement at the same wavelength. If the laser is incident on the wafer at a specific angle of incidence and polarization state those aspects may also be incorporated in the measurement.

It should be understood, that measurements on both the front surface and the back surface of the substrate may be performed to provide a more complete description of the optical properties of the substrate. As described above, in one embodiment, the measurements may also be taken at a number of positions across the surface of the wafer. This information may then provide a map of the spatial distribution of radiative properties across the wafer.

Taking measurements at multiple locations across the wafer's surface may be especially valuable for improving the uniformity of processing, for example by improving temperature uniformity. For instance, the information about the variation of optical or thermal properties across the wafer's surfaces could be provided to the measurement and control systems. In one embodiment, the information can be used by a model-based controller in order to predict how to optimize the heating conditions at different locations on the wafer. For example, the distribution of properties can be provided to a model-based control system that predicts optimized settings for power provided to different banks of lamps so as to optimize temperature uniformity. Similar methods can also be used to control power coupling variations when heating or otherwise subjecting the substrate to one or more laser beams.

Information about the variation of optical properties across the surface may be useful for correcting the readings of sensors that sense temperature at different locations on the wafer. Information about variations in the thickness or the doping of the wafer may also be used for similar purposes. Likewise, information about variations in the coatings or patterns on the wafers can be used in a similar manner.

In some cases it may be useful to perform the measurements in at least two configurations, one where the reflected light is only collected from the illuminated surface, and one where the optical configuration so that the depth of focus is large and light is collected after reflection at both surfaces of the wafer (as in the case shown in FIG. 3). These two cases could be accommodated by changing the depth of focus within one optical pathway, for example through the use of an aperture as shown in FIG. 10 or through separate measurement steps.

The combination of reflectivity measurements from both surfaces of the wafer, and a wafer transmission measurement allows a rather complete characterization of optical properties. One useful aspect of transmissivity or reflectivity measurements performed at room temperature are that they allow for determination of whether the wafer is heavily-doped or not. This can be ascertained by deducing the degree of optical absorption at wavelengths greater than ~1 μm. If the absorption coefficient is significantly greater than that expected for lightly-doped material, such as silicon of a resistivity of more than 0.5 Ωcm, then the material can be identified as heavily doped. This information can then be used to improve temperature measurement accuracy and to improve the temperature control, especially during processing at temperatures below ~800° C.

Performing premeasurements at more than one temperature, for instance, can be used to distinguish lightly-doped wafers from heavily-doped wafers, or in general to provide information about the nature of the doping. Taking measurements at more than one temperature, may also be useful in determining other properties of the wafer. For instance, the measurements at different temperatures, in conjunction with the sensing of surface reflectivities, may show temperature dependence in the surface reflectivities. That information can be useful for improving the accuracy of the estimates of the temperature dependence of reflectance, transmittance, emittance, or absorptance. For example, the reflectivities of the surfaces at the temperatures of interest (T2) can be obtained by extrapolating from the measurements obtained at other temperatures, such as T1 and T3. The concept of characterizing at more than one temperature and extrapolating to a third temperature may also be useful for estimating the temperature dependence of the absorption coefficient of the substrate.

Any of these measurements can be combined with an approach that modulates the light transmission through the substrate, for example through the illumination that introduces extra free carrier absorption, for example, by creating extra electron-hole pairs in the semiconductor. Modulation of the degree of absorption will manifest itself through a corresponding modulation in components of the reflected or transmitted radiation that are sensitive to propagation of rays through the thickness of the substrate. This approach may be useful in improving accuracy. We can also modulate the light transmission by applying other forms of radiation, including electron irradiation, which could be conveniently obtained by mechanical modulation of a flux of beta particles from a beta-radiation emitter. It may also be possible to obtain extra information by deliberately modulating the wafer temperature and observing changes in the measured properties.

As described above, the wafer surfaces may scatter radiation as a result of patterning or variations in surface topography. In such cases, the intensity of the beams of reflected and transmitted light may be affected by the scattering pattern. One way of characterizing the presence and degree of scattered light is to examine whether the transmittance measured for light incident on either surface of the wafer is the same. If it is different depending on the surface illuminated, then it is likely that at least one of the wafer surfaces is scattering light in directions that are not correctly collected for the transmittance measurement. Hence measurement of an asymmetric transmittance can be a symptom of light scattering. Characterization of the light scattering pattern of the wafer can help to improve accuracy of predictions of optical properties. This can be especially helpful in providing improved estimates of spectral emittance at a pyrometer wavelength. In some cases, where the effects of light scattering are especially significant, it may be necessary to measure the bidirectional reflectance distribution function of the wafer to make an accurate estimate of the spectral emittance. It can also be helpful to use integrating spheres to control the illumination conditions for measurements of reflectance and transmittance.

When characterizing the interaction between the wafer and any given heating energy source, the calculation often requires the spectral distribution of the energy emitted by the energy source to be taken into account. This aspect can be covered by measuring the optical properties of interest as a function of wavelength, over a wavelength interval that covers the spectral region where the energy source emits its energy. A weighted integral of the optical property can then be used to obtain the integrated property. For example, if the property of interest is a quantity $f(\lambda,T)$, and the energy source emits a spectrum $I_L(\lambda)$, then the integrated property is $F(T)$, where $$F(T) = \frac{\int I_L(\lambda) f(\lambda, T) d\lambda}{\int I_L(\lambda, T) d\lambda}.$$

The integrals are performed over a wavelength range that includes most of the energy emitted by the heating source. The quantity $f(\lambda,T)$ could be the reflectance, absorptance, transmittance etc. For determination of power coupling to an energy source, the integrated absorptance is of special interest. Similar principles can be applied to determining the integrated emittance, such as the total emittance. In this case, the weighting spectrum is the black-body radiation spectrum for the temperature of interest. For example, the total emittance, $\epsilon_{tot}(T)$ can be calculated from the spectral emittance, $\epsilon(\lambda,T)$ according to the equation $$\varepsilon_{tot}(T) = \frac{\int W_{bb}(\lambda, T)\varepsilon(\lambda, T)d\lambda}{\int W_{bb}(\lambda, T)d\lambda},$$

where $W_{bb}(\lambda,T)$ is the Planck radiation function that describes the emission spectrum of a black-body radiator. The integrals are performed over a wavelength range that includes most of the energy emitted by a blackbody radiator at temperature T. Estimates of integrated emittance can be used to help determine the degree of heat radiated away from the wafer when it is at any given temperature. An alternative approach for determining integrated properties can involve illuminating the wafer with an appropriate spectrum and hence directly performing an integrated measurement. The latter approach may require a careful tailoring of the illumination spectrum and the spectral response of the optical detection system, but may have the advantage of being faster and simpler in some cases.

As described above, in one embodiment, measurements may be taken on both the front surface and the back surface of the substrate in order to provide a more complete description of the optical properties of the substrate. In still another embodiment, both sides of the wafer may be both illuminated for taking dual-sided measurements.

Figure 15:
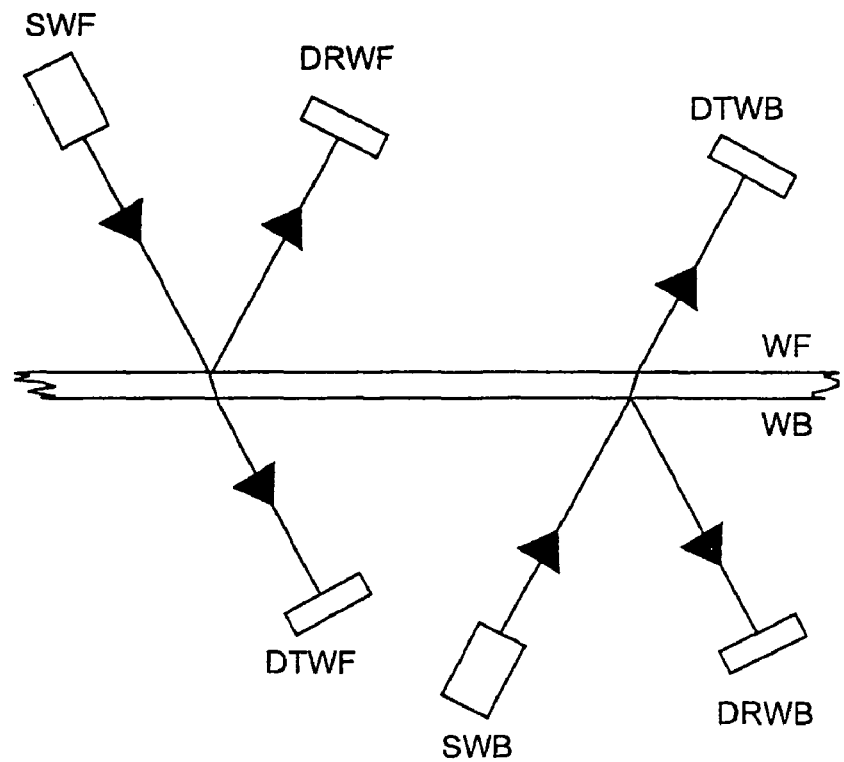
FIG. 15 is a side view illustrating one embodiment for dual-sided illumination of a wafer.

For example, FIG. 15 shows the arrangement where the apparatus includes the capability to provide light that is incident on either of the wafer's two surfaces. Radiation source SWF illuminates the front side of the wafer (WF). Light that is reflected from WF is collected by DRWF, which is a radiation collection and sensing arrangement. DRWF can include optics that limit the radiation that is sensed to being only that component that is reflected from WF, if desired. Likewise DTWF is a radiation collection and sensing arrangement that collects radiation transmitted through the wafer. Radiation source SWB illuminates the back side of the wafer (WB). Light that is reflected from WB is collected by DRWB, which is a radiation collection and sensing arrangement. DRWB can include optics that limit the radiation that is sensed to being only that component that is reflected from WB, if desired. Likewise DTWB is a radiation collection and sensing arrangement that collects radiation transmitted through the wafer. The combination of these measuring sub-systems allows measurements with illumination from either side of the wafer for a more complete characterization of the wafer's properties.

Figure 16:
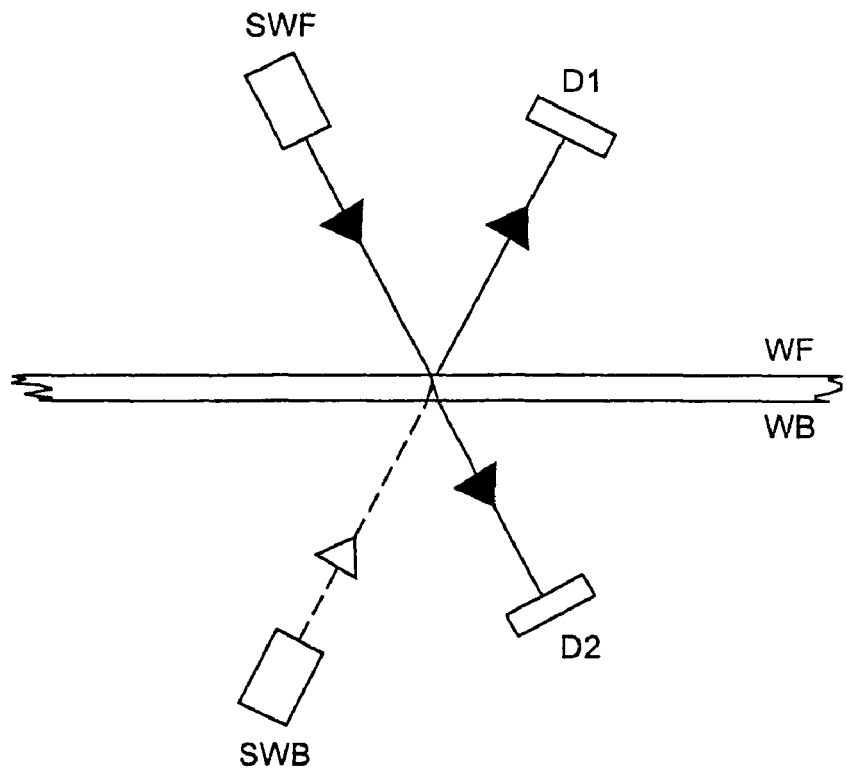
FIG. 16 is a side view illustrating another embodiment for dual-sided illumination of a wafer.

FIG. 16 shows a second arrangement where the apparatus includes the capability to provide light that is incident on either of the wafer's two surfaces. Radiation source SWF illuminates the front side of the wafer (WF). Light from SWF that is reflected from WF is collected by D1, which is a radiation collection and sensing arrangement. D1 can include optics that limit the radiation that is sensed to being only that component that is reflected from WF, if desired. Likewise D2 is a radiation collection and sensing arrangement that collects radiation from SWF that is transmitted through the wafer. Radiation source SWB illuminates the back side of the wafer (WB). In this arrangement the optics are configured so that light from SWB that is reflected from WB is collected by D2. D2 can include optics that limit the radiation that is sensed to being only that component that is reflected from WB, if desired. Likewise D1 can collect radiation from SWB that is transmitted through the wafer. This embodiment can perform the same measurements as those possible with FIG. 15, but this embodiment uses less optical components and detectors and hence would be cheaper and simpler. It also may be easier to perform the measurements at the same spatial location on the wafer with the scheme in FIG. 16. If desired, the measurements using radiation from SWF and from SWB can be performed at different times, to prevent radiation from SWF reaching the sensors at the same time as they are sensing radiation from SWB. Alternatively the measurements can be separated by using modulation of the radiation output from at least one of SWF or SWB to provide a time-varying characteristic to at least one of the signals that allows it to be distinguished as arising from radiation from a particular light source. For example, the output of SWF can be intensity modulated at a known frequency and the signals from D1 and D2 can be filtered to track the behavior of that frequency component. Other methods of separating the signals can include exploitation of differences in the light output from SWF and SWB, such as wavelength or state of polarization. It is also possible for the characteristics of the light collection and sensing arrangements D1 and D2 to be varied so that they are more appropriate for the measurement of radiation from SWF or from SWB. For example, the characteristics of D1 may be set to optimize the collection of reflected light while it is collecting light from SWF that is reflected from the wafer, and then they may be set to optimize the collection of transmitted light when it is collecting light that is transmitted from SWB. Of course, the characteristics may be optimized to perform both of these function simultaneously if so desired.

Characteristics of the light collection and sensing arrangements shown in FIGS. 15 and 16 that can be optimized for measurement of wafer properties can include adjustment or selection of the position or shape of optical elements such as lenses, apertures, mirrors and detectors. They can also include adjustment of filtering or polarizing elements. They can also include such as electronic or digital filters, amplifier settings and signal processing circuits and algorithms. The radiation sources SWF and SWB can also include optical and electronic elements that assist in optimizing the measurement of components of reflected or transmitted light, and these elements can be varied for measurement of specific wafer properties if desired. Although the configurations shown in FIG. 15 and FIG. 16 show light incident at an angle to the normal of the wafer, the measurements may also be made at or near normal incidence if desired. In such cases it is convenient to include beam-splitting optics that allow the light collection and sensing arrangements to sample radiation reflected or transmitted by the wafer while not completely blocking the path of the incident radiation.

For many applications it is useful to make the optics that deliver radiation to the wafer or that collect radiation reflected from or transmitted by the wafer achromatic. Such optics have the characteristic that their focusing properties do not vary significantly with wavelength. This allows the measurements to be performed over a broad range of wavelength (either sequentially or simultaneously) while sampling radiation from the same region of the wafer. An achromatic approach is most easily achieved through the use of reflective optics.

Figure 17:
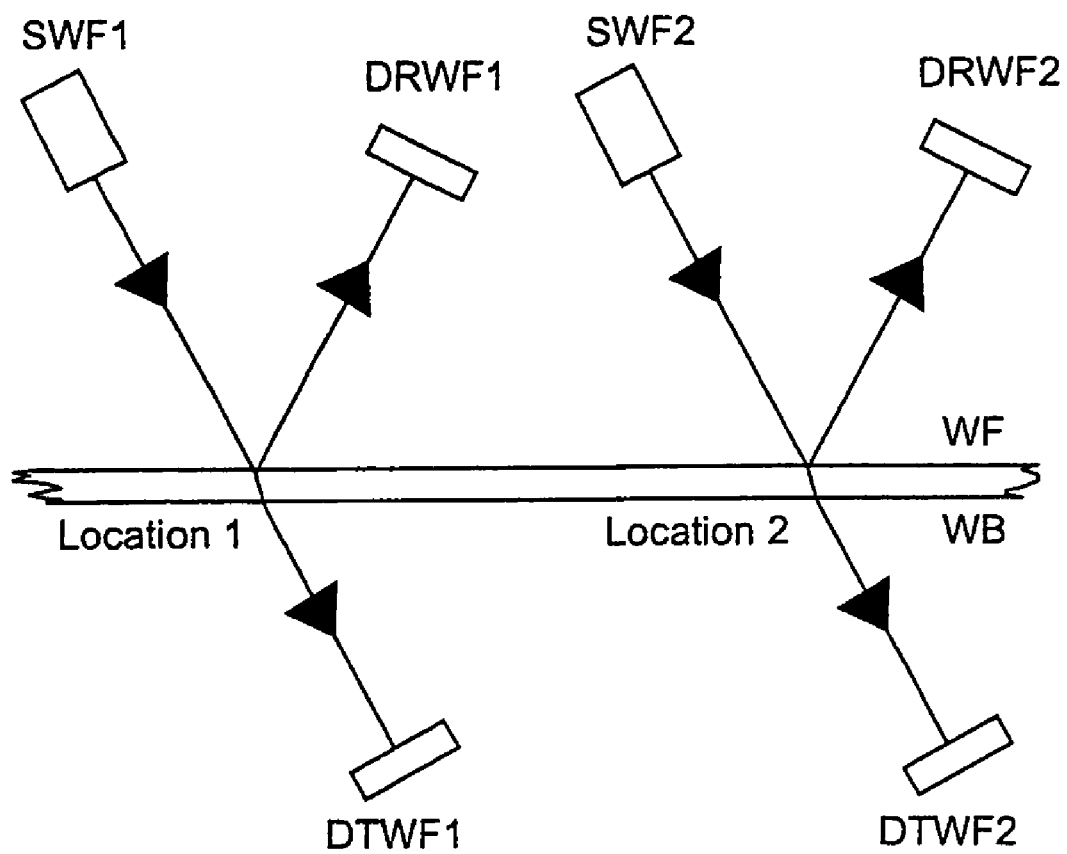
FIG. 17 is a side view illustrating an embodiment for illuminating a wafer at different locations in accordance with the present disclosure.

FIG. 17 shows an example of an apparatus where the measurements are performed at more than one location on the wafer. In this example, the light is incident on the front surface of the wafer, but the approach is easily extended to measurements with light incident on the back surface of the wafer, or to the approaches of FIGS. 16 and 17, where dual-sided measurements are possible. Measurements at several locations or even mapping of the wafer's properties are also possible by other schemes. For example, the wafer can be mechanically moved past a measuring arrangement, so that properties can be evaluated at different locations. Alternatively, the measuring apparatus can be moved relative to a stationary wafer, or the beams of radiation used for measurement can be scanned over the surface of the wafer. Another approach would involve illuminating the whole wafer, or at least a fraction of the wafer, with a broader beam of radiation and analyzing the reflected and transmitted beams of radiation. The beam can contain light reflected from the whole of the wafer, or from a sub-region, such as a line-shaped region. Such analysis can be performed by scanning radiation collecting and sensing arrangements with respect to the beams of radiation, or scanning the beams of radiation relative to the collecting and sensing arrangement. Alternatively, the beams of light can be collected by optical systems and delivered to imaging devices, such as cameras.

Practical Applications of the Above Described Methods

Once we have obtained measurements of the surface reflectivities, and if desired the wafer transmissivity, this information can then be used to predict the thermal radiative properties of the wafer during wafer processing. A very simple approach could be applied for processes conducted at wafer temperatures T>700° C. In this case, for most considerations, silicon wafers that are >600 μm thick can be considered to be opaque at all wavelengths of interest. If this is the case, the reflectivity and the wafer emissivity at any given wavelength can be related by Kirchhoff's law.

A more sophisticated approach would incorporate information about the wafer's temperature to make an improved estimate of the radiative properties. For example, if a pyrometer reading is available then the temperature deduced from this can be used to improve estimates of properties in various ways. One approach would be to predict the absorption coefficient of the wafer from a model, and then combine this property with the room temperature measurements of optical properties of the wafer to provide a more accurate estimate of the high-temperature properties of the wafer.

The pyrometer reading could also be used to provide a better estimate of the radiation loss from the wafer. The loss depends on both the radiative properties and the temperature. By combining estimates of the two properties, an improved estimate of the radiative heat loss from various regions of the wafer can be obtained, and hence the wafer temperature control and temperature uniformity can be improved by making suitable adjustments to the lamp powers.

For example, the following are more detailed methods for using the information collected from the optical pathways illustrated in the figures. As mentioned above, in one embodiment, the present disclosure is directed to a method of correcting the readings of a radiation sensing device, such as a pyrometer, at high temperature where the internal transmittance of the substrate is less than 0.1. In this embodiment, the optical pathway of the present invention is used to collect light reflected from one surface of the wafer, such as the front surface of the wafer. The measurements are taken while the wafer is at a relatively low temperature, such as at ambient temperature. The measurements are also performed at substantially the same wavelength range at which the pyrometer operates.

From the method of the present disclosure, the reflectivity of the front surface of the wafer is determined. This reflectivity is used to deduce or determine reflectance of the wafer at high temperature. Specifically, at high temperature, reflectance is substantially the same as reflectivity of the front surface due to the decrease of internal transmittance with temperature. From the reflectance, the emittance of the wafer may be determined. For example, the emittance is generally equal to 1 minus the reflectance. The determined emittance is then used to correct pyrometer readings and improve the accuracy of temperature control.

In an alternative embodiment, the methods of the present invention can also be used to correct for pyrometer readings at lower temperatures where the internal transmittance of the substrate is greater than 0.1. In this embodiment, the optical arrangement as shown in the figures may be used to collect and determine the amount of light reflected from one surface of the wafer while the wafer is at a relatively low temperature and at the wavelength range at which the pyrometer operates.

In this embodiment, the optical arrangement of the present disclosure may also be used to collect light reflected from the opposite surface of the wafer, such as the back surface of the wafer using the same conditions as above. From this information, the reflectivity of the front surface of the wafer and the reflectivity of the back surface of the wafer may be determined. Transmittance of the wafer may then be measured or may be determined from a model or other measurement of the wafer at higher temperature.

After the transmittance is determined, the emittance of the wafer can be determined. For instance, the emittance is generally equal to 1 minus the transmittance minus the reflectance. This emittance can then be used to correct pyrometer readings and improve the accuracy of temperature control.

In addition to providing improved temperature measurements, the methods of the present disclosure can also be used to control the heating devices in order to optimize power absorption. For example, at higher temperatures where the internal transmittance of the wafer is less than 0.1, the methods of the present disclosure can be used to collect and determine the amount of light reflected from one surface, such as the front surface of the wafer. These measurements may be completed at low temperatures, such as at or near ambient temperature. In this embodiment, however, the wavelength range at which the measurements are taken should substantially overlap with the wavelength range for the heating device that is used to heat the wafer during processing.

Once the reflectivity of one surface of the wafer is determined, the reflectivity is used to determine reflectance at higher temperatures. As mentioned above, at higher temperatures, reflectance is substantially equal to the reflectivity, due to the decrease of internal transmittance.

The reflectance can then be used to determine absorptance, which is generally equal to emittance at higher temperatures. In particular, absorptance equals 1 minus the reflectance. The absorptance can then be used to optimize power absorption and/or the energy setting for one or more heating devices contained in the chamber.

The above method is particularly well suited for systems such as those shown in FIG. 1 where the wafer 14 is heated by the heating device 22 from one side of the wafer. If both sides of the wafer are heated by separate heating devices, however, the above method can be repeated for the opposite surface of the wafer. In this manner, a first heating device heating the top of the wafer may be controlled independently of a second heating device heating the bottom of the wafer.

The methods of the present disclosure can also be used to optimize the settings of the heating device at lower temperatures where the internal transmittance of the substrate is greater than 0.1. In this embodiment, an optical arrangement is used to collect light reflected from one surface of the wafer at or near ambient temperature and at a wavelength range that substantially overlaps with the wavelength range of the heating device that heats the wafer. The same measurement determinations are then carried out on the opposite surface of the wafer at similar conditions.

From this information, the reflectivity of the front surface and the reflectivity of the back surface of the substrate may be determined. Transmittance of the substrate is then measured or deduced from a model of the wafer at higher temperatures. Once transmittance is determined, the absorptance may be estimated by assuming that the absorptance is substantially equal to the emittance. Therefore, the absorptance is equal to 1 minus transmittance minus reflectance based on one side of the wafer. The absorptance is then used to optimize power output over the heating device and/or the energy setting of the heating device during wafer processing.

Again, if a first heating device heats one side of the wafer and a second heating device heats an opposite side of the wafer, the above method can be repeated for the opposite surface of the wafer for optimizing both of the heating devices independently of one another.

In addition to the above embodiments, the information obtained from methods of the present disclosure can be used to control various other parameters contained within the thermal processing chamber.

Figure 2:
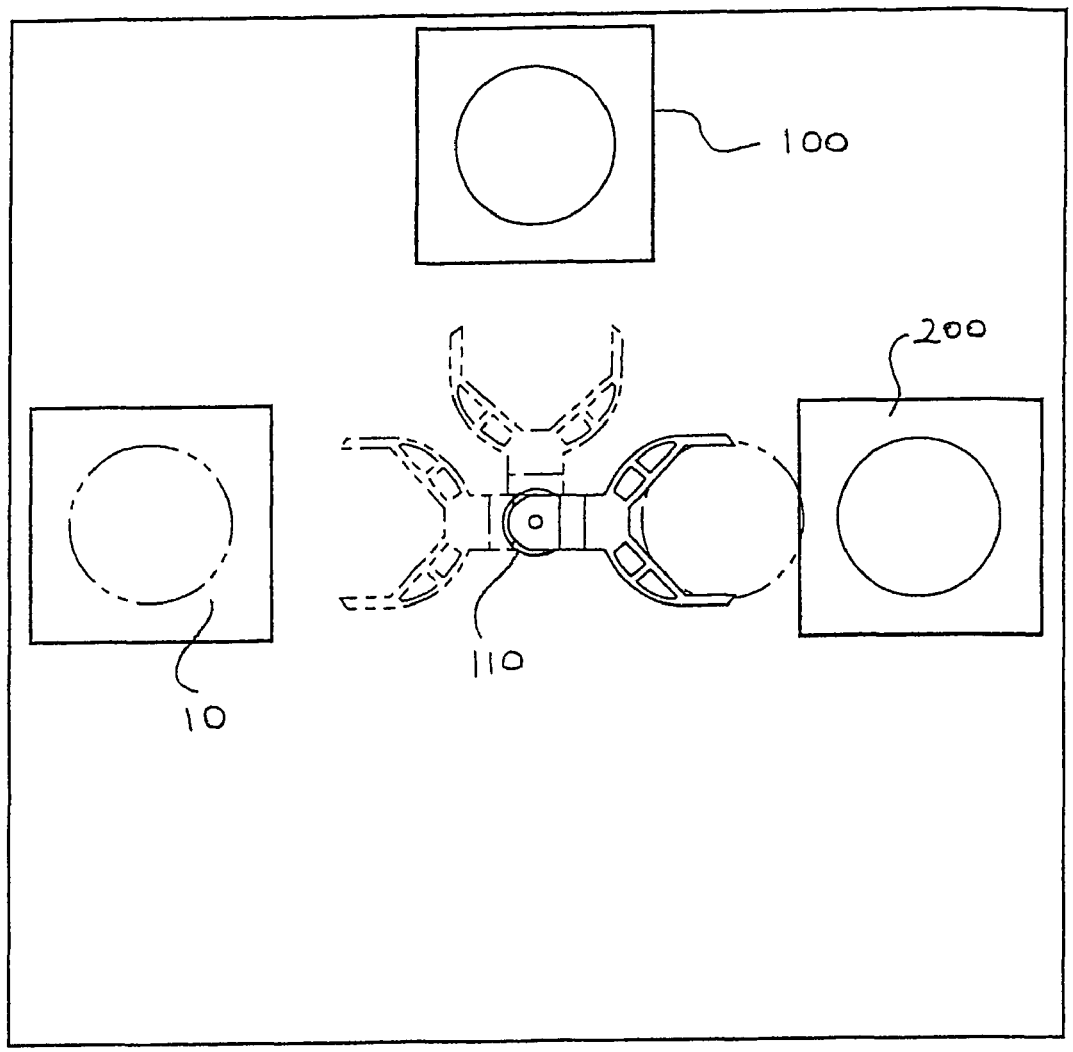
FIG. 2 is a plan view of one embodiment of a system made in accordance with the present invention.

Although the optical characteristic of the substrate as described above may be determined within the thermal processing chamber 10 as shown in FIG. 10, in one embodiment, the optical characteristics may be determined at a different location, such as on any suitable platform, on a robotic arm or in a separate chamber. In addition, the above measurements may occur immediately prior to processing or at a different time to the wafer processing itself. For example, referring to FIG. 2, an entire wafer processing system is illustrated. In this embodiment, a plurality of wafers are stacked in a cartridge 100 that is placed in close proximity to the thermal processing chamber 10 and a wafer optical processing chamber 200 made in accordance with the present invention. In order to move the wafers from one location to another, the system further includes a wafer handling device 110.

During processing, wafers contained in the cartridge 100 may be moved to the wafer optical processing chamber 200 in order to determine at least one optical characteristic of the wafer in accordance with the methods described above. Once the wafer characteristics are determined, the wafer is then transferred to the thermal processing chamber 10 once again using the wafer handling device 110. The optical characteristics of the wafer that are determined in the wafer optical processing chamber 200 may then be used to control at least one process variable or system component in the thermal processing chamber 10. For example, the information may be used to control a power controller for the heating device or may be used to calibrate or otherwise control a pyrometer used to determine the temperature of the wafer during processing.

Referring back to FIG. 1, the thermal processing system 10 may further include a system controller 50 which can be, for instance, a microprocessor. Controller 50 can be configured to receive voltage signals from the light detectors 30 that represent the radiation amounts being sampled at the various locations. Controller 50 may be configured to calculate the temperature of the wafer 14 based upon the amount of radiation sensed from the light detectors 30 in conjunction with the optical characteristics that are determined in the wafer optical processing chamber 200.

The system controller 50 as shown in FIG. 1 can also be in communication with the heating device power controller 25. Again, based upon the optical characteristics of the wafer that are determined outside of the chamber, the controller 50 can selectively increase or decrease the power to the heating device for optimizing absorption of thermal energy being emitted by the heating device and being absorbed by the wafer 14. In addition to controlling radiation intensity, however, it should be understood that the power controller 25 in conjunction with the system controller 50 may be used to control the heating device 22 in other ways. For instance, the system controller 50 may also be configured to change the amount of radiation being emitted by the lamps 24 such that different portions of the surface of the wafer are subjected to different amounts of radiation. The angle of incidence at which the radiation contacts the wafer 14 and the wavelength of the radiation may also be selectively controlled in accordance with the present invention.

Prior to a further detailed discussion of various particular methods in accordance with the present disclosure, it may be helpful to initially discuss how light travels through a wafer, even when the wafer contains front side or back side coatings and how the intensity of light changes based upon its travel path.

Figure 18:
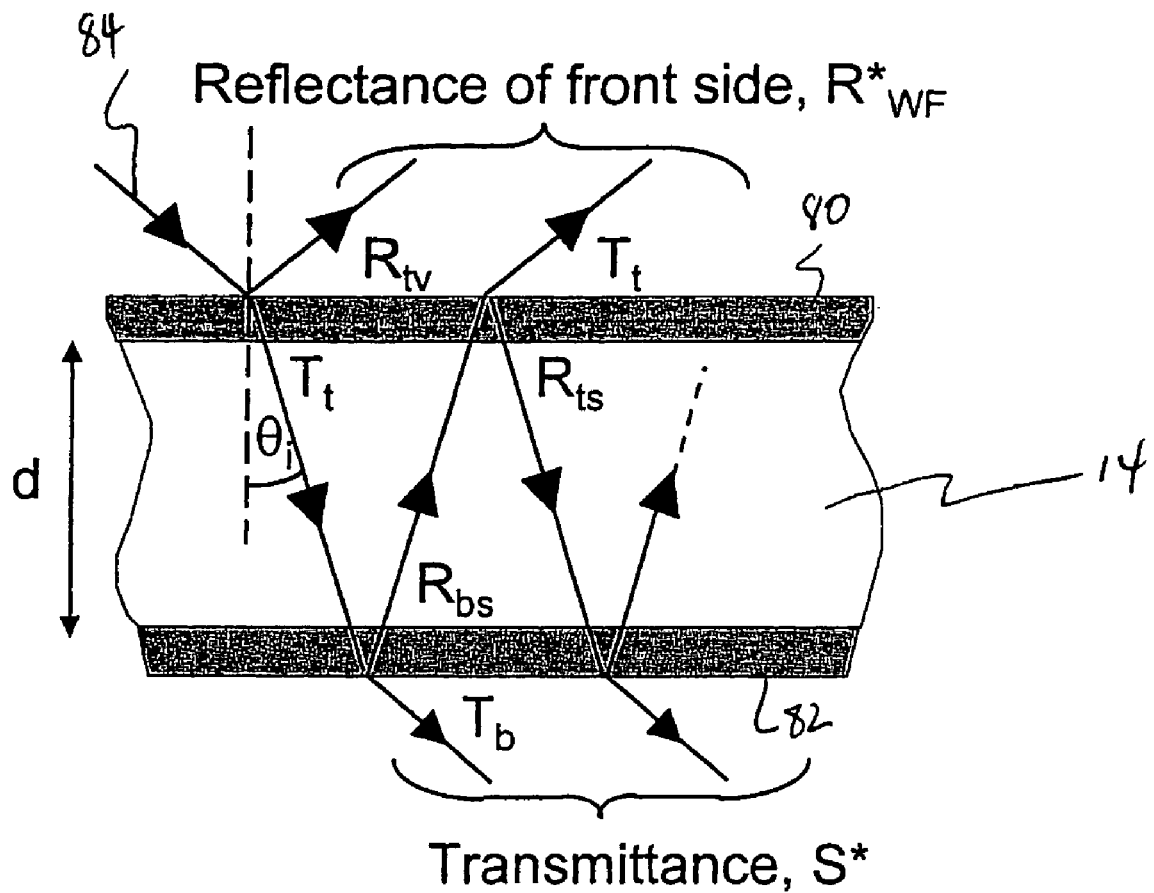
FIG. 18 is a side view illustrating a light beam being emitted onto a semiconductor wafer containing front side and back side coatings.

For example, referring to FIG. 18, a substrate or wafer 14 is shown including a front side coating 80 and a back side coating 82. A ray of incident power 84 is shown contacting the front side coating 80 of the wafer 14.

A general wafer 14 as shown in FIG. 18 has various properties that should be considered when practicing methods according to the present disclosure. For instance, the two surfaces of the wafer may have different reflectivities and transmissivities. Furthermore, the reflectivities of the surfaces may be different for radiation incident on them from outside the wafer, or from within the wafer. The surface regions may include various films and patterns that affect these reflectivities and transmissivities. These surface regions (on both front and back of the wafer) cover the substrate material that forms the bulk of the wafer. When a wafer is semi-transparent, multiple reflections of the various beams of energy propagating within the wafer affect its front side reflectance, $R^*_{WF}$, and its transmittance, $S^*$, as observed from outside the wafer. All of the optical properties may be functions of wavelength, $\lambda$, and of temperature, $T$.

In the discussion below, $T_t$ is the transmissivity of the top surface of the wafer, $T_b$ is the transmissivity of the bottom surface of the wafer, $R_{tv}$ is the reflectivity of the top surface of the wafer for radiation incident on it from outside the substrate, $R_{ts}$ is the reflectivity of the top surface of the wafer for radiation incident on it from within the substrate and $R_{bs}$ is the reflectivity of the bottom surface of the wafer for radiation incident on it from within the substrate. In general, if the incident radiation is not at normal incidence, all of the properties will be functions of the angle of incidence and the plane of polarization of the radiation.

In general, the material of the bulk of the wafer has an absorption coefficient, $\alpha(\lambda,T)$ that is a function of the wavelength of the radiation, $\lambda$, and the temperature T. The attenuation in intensity experienced by a ray passing through the substrate, can be described by the quantity $$a = \exp(-\alpha(\lambda,T)d/\cos\theta_i), \quad (1)$$

where d is the thickness of the substrate and $\theta_i$ is the internal angle of propagation. The latter angle is the angle between the direction of the ray and the normal to the wafer surface. As used herein, the quantity "a" refers to the internal transmittance.

Figure 19:
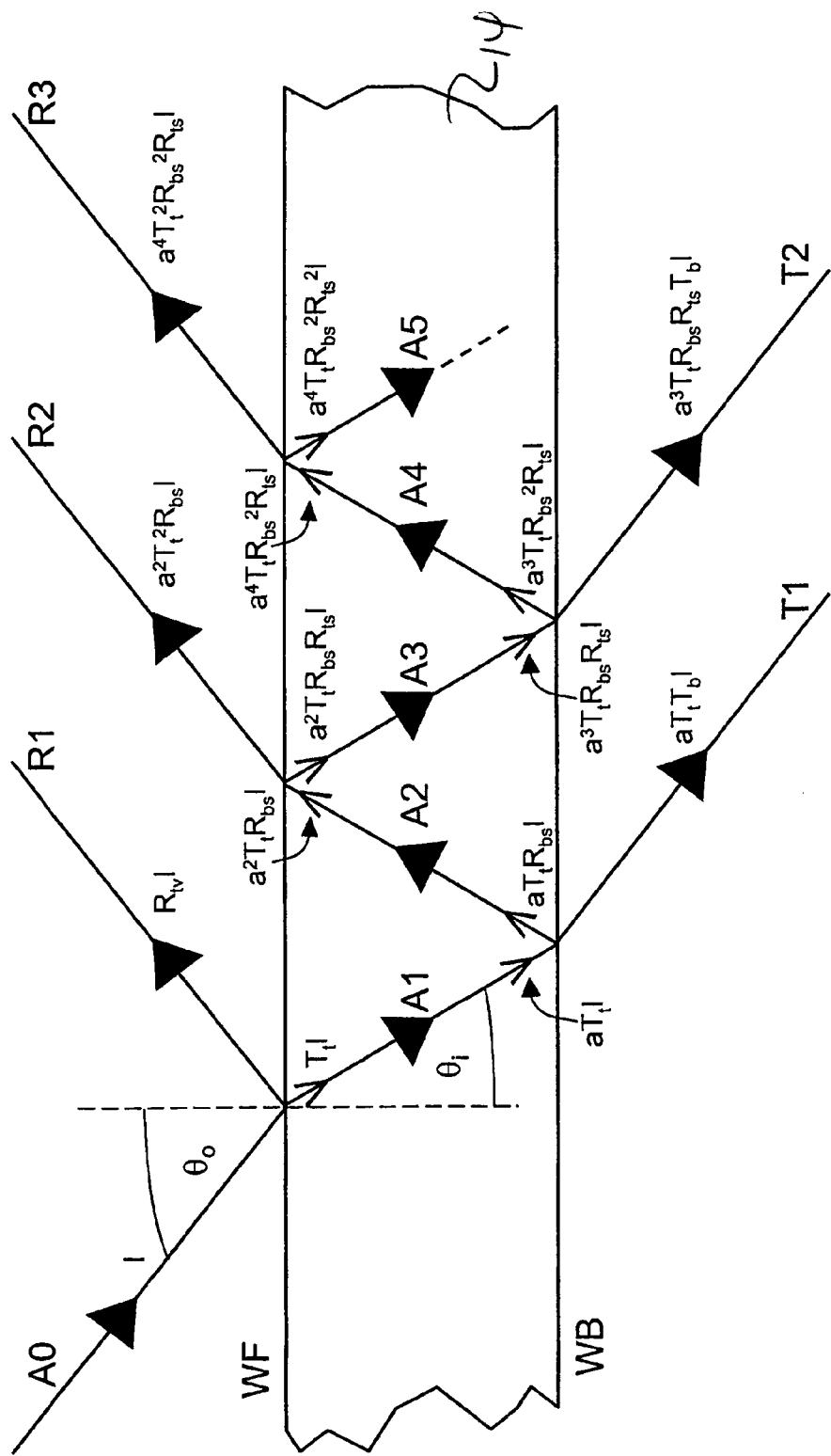
FIG. 19 is a side view illustrating the propagation of rays of light incident on the front surface of a wafer and the values for intensity of light at various positions.

In FIG. 19, we see that the intensity of the reflected ray R1 is only affected by the reflectivity of the front surface of the wafer (WF), $R_{tv}$, so that if the incident ray has intensity I, then ray R1 has intensity $R_{tv}I$. The ray that has been transmitted into the substrate has intensity $T_tI$ just at the point where it has passed through the front surface region into the bulk of the wafer. As the ray A1 traverses the substrate it loses intensity because of absorption of energy. As a result it has an intensity $aT_tI$ just at the point where it reaches the back surface region (WB). The portion that is reflected at the back surface to form the internal ray A2 has intensity $aT_tR_{bs}I$, and the portion that is transmitted to form the ray T1 has intensity $aT_tT_bI$. When the reflected ray A2 reaches the front surface it has lost more intensity as a result of absorption in the substrate and now has intensity $a^2T_tR_{bs}I$. The portion of ray A2 that is reflected at the front surface to form ray A3 initially has intensity $a^2T_tR_{bs}R_{ts}I$, whereas the portion that is transmitted back out through the front surface forms ray R2, having an intensity $a^2T_t^2R_{bs}I$. When ray A3 reaches the back surface it has an intensity $a^3T_tR_{bs}R_{ts}I$. The portion of A3 that is reflected, forming ray A4, initially has intensity $a^3T_tR_{bs}^2R_{ts}I$, whereas the portion that is transmitted through the back surface, forming ray T2, has intensity $a^3T_tR_{bs}R_{ts}T_bI$. When ray A4 reaches the front surface it has intensity $a^4T_tR_{bs}^2R_{ts}I$. The portion reflected from front surface to form ray A5 has an intensity $a^4T_tR_{bs}^2R_{ts}^2I$, whereas the portion that is transmitted through the front surface to form ray R3 has an intensity $a^4T_t^2R_{bs}^2R_{ts}^2I$. From this point on, it is easy to see that as more multiple reflections occur, each of the successive transmitted or reflected rays that emerge from the substrate will be further attenuated relative to the previous one. The attenuation arises as a result of two passages through the substrate and by a reflection from the top surface and from the bottom surface, so that each ray decreases in intensity by a factor of $a^2R_{ts}R_{bs}$, relative to the previous ray.

The total intensity transmitted by the wafer can be obtained by summing up all the components T1, T2, etc. which make up a sequence of the form $$aT_tT_bI + aT_tT_b(a^2R_{ts}R_{bs})I + aT_tT_b(a^2R_{ts}R_{bs})^2I + aT_tT_b(a^2R_{ts}R_{bs})^3I + \ldots, \quad (2)$$

which can be simplified to the expression $$IaT_tT_b\{1 + a^2R_{ts}R_{bs} + (a^2R_{ts}R_{bs})^2 + (a^2R_{ts}R_{bs})^3 + \ldots\}. \quad (3)$$

Likewise the total intensity reflected from the wafer can be obtained by summing all the components R1, R2, R3, etc. which make up a sequence of the form $$R_{tv}I + a^2T_t^2R_{bs}I + a^2T_t^2R_{bs}(a^2R_{ts}R_{bs})I + a^2T_t^2R_{bs}(a^2R_{ts}R_{bs})^2I + a^2T_t^2R_{bs}(a^2R_{ts}R_{bs})^3I + \ldots, \quad (4)$$

which can be simplified to the expression $$I[R_{tv} + a^2T_t^2R_{bs}\{1 + a^2R_{ts}R_{bs} + (a^2R_{ts}R_{bs})^2 + (a^2R_{ts}R_{bs})^3 + \ldots\}]. \quad (5)$$

The expressions (3) and (5) include geometric series which can be reduced to simpler expressions. Taking the ratio of the total transmitted energy to the incident intensity, I, gives the transmittance of the wafer as $$S^* = \frac{aT_tT_b}{1 - a^2R_{ts}R_{bs}}. \quad (6)$$

Likewise, the reflectance for the front side of the wafer is given by the expression $$R^*_{WF} = R_{tv} + \frac{a^2T_t^2R_{bs}}{1 - a^2R_{ts}R_{bs}}. \quad (7)$$

In general, the transmittance and the reflectance also depend on the angle of incidence and the plane of polarization being considered. This issue can be handled by considering the two orthogonal planes of polarization, the p- and s-polarization states, separately. For each case, the appropriate reflectivities and transmissivities are used to determine the corresponding reflectance and transmittance. The emittance, $\epsilon_{WF}$ or absorptance, $A_{WF}$ of the front side of wafer for any given wavelength, angle of incidence and polarization state can be obtained from the expression $$\epsilon_{WF} = A_{WF} = 1 - S^* - R^*_{WF}. \quad (8)$$

Combining equations 6, 7 and 8 we can deduce that $$\varepsilon_{WF} = A_{WF} = 1 - R_{tv} - \frac{aT_t(T_b + aT_tR_{bs})}{1 - a^2R_{ts}R_{bs}}. \quad (9)$$

This expression can be used to calculate the emittance or absorptance of the front side of the wafer, given the appropriate set of data on the reflectivities, transmissivities of the surfaces as well as the absorption coefficient and thickness of the substrate.

Determination of Specific Properties by Selectively Collecting Energy from Specific Rays Conventional measurements do not discriminate between the various rays of reflected or transmitted light that contribute to the total intensity transmitted or reflected by the wafer. As a result, information is lost that may be useful in characterizing the wafer properties. For example, by selectively measuring the intensity of ray R1, the quantity $R_{tv}$ can be deduced directly, without needing to know a, $T_t$, $R_{bs}$ or $R_{ts}$, as would be required if $R^*_{WF}$ was measured. Likewise, by selectively measuring the intensity of ray T1, the quantity $aT_tT_b$ can be determined, without needing to know $R_{bs}$ or $R_{ts}$, as would be required if $S^*$ were measured.

Furthermore, by selectively measuring the intensity of other rays, one can obtain even more information. For example, if the internal transmittance, a, is determined then equation 1 can be used to deduce the absorption coefficient. The absorption coefficient can be calculated by rearranging equation 1 to give $$\alpha(\lambda, T) = -\frac{\cos\theta_i}{d}\ln a, \quad (10)$$

and for normal incidence this simplifies to the case where $\theta_i = 0$, so that $$\alpha(\lambda, T) = -\frac{\ln a}{d}. \quad (11)$$

In cases where the radiation is not incident at normal incidence, the angle $\theta_i$ can be obtained from Snell's law. In practice the refractive index of most semiconductor materials is rather high (>3), so that an approximation that $\theta_i \cong 0$ usually results in less than 7% error in the value obtained for the absorption coefficient, and if the angle of incidence of the radiation impinging on the wafer is <30°, then the error would typically be less than 2%.

By selectively measuring the intensity of ray R2, the quantity $a^2T_t^2R_{bs}$ can be obtained. This is especially useful because its dependence on the internal transmittance enables us to use a measurement of a component of reflected light to deduce the magnitude of optical absorption in the substrate. Although optical absorption in the substrate is usually determined by performing transmittance measurements, in some circumstances it may be difficult to perform a transmittance measurement, because of geometric, mechanical or other constraints, in which case it would be useful to use a reflection measurement to achieve this goal. Although $R^*_{WF}$ is also affected by the internal transmittance, it may be difficult to use a direct of measurement of $R^*_{WF}$ to deduce the internal transmittance. For example, if the intensity of ray R1 is much larger than that of ray R2 then a measurement of $R^*_{WF}$ is dominated by the first surface reflection, $R_{fv}$, which does not depend on the internal transmittance. As a result it may be difficult to make a very accurate determination of the contribution of rays R2, R3, etc. to the reflectance. This makes the determination of the internal transmittance based on a measurement of $R^*_{WF}$ more prone to error. In contrast, the intensity of ray R2 is directly affected by the magnitude of the internal transmittance, so its measurement can give a more accurate estimate.

The reflected component R2 is also influenced by the transmissivity of the top surface of the wafer, $T_t$, and by the reflectivity of the back surface, $R_{bs}$. Hence by measuring the intensity of R2, the above properties may also be determined. The reflectance, $R^*_{WF}$ is also sensitive to them, as a result of the contributions of ray R2, R3, etc. However, it is also affected by $R_{fv}$ and $R_{ts}$, so it may be more difficult to use a measurement of $R^*_{WF}$ to deduce $T_t$ or $R_{bs}$.

Selective measurements of individual contributions of any of the other rays may also be useful in various circumstances. For example the ray T2 is sensitive to the quantities a, $T_t$, $T_b$, $R_{bs}$ and $R_{ts}$. A measurement of the intensity of this ray allows a transmission measurement to provide information about the reflectivity of the front surface for radiation incident from within the substrate, $R_{ts}$. The ratio of intensities of rays can also be useful. For example, the ratio of the intensity of rays T2 to T1, or R3 to R2 gives the quantity $a^2 R_{ts} R_{bs}$.

Separate Measurements of Back Surface of Wafer and Front Surface

For fuller characterization of the properties of the wafer, it may be useful to arrange for separate measurements of reflected and/or transmitted light components to be made for light incident on the wafer from two opposite sides. For example the ray of light A0 may be incident on the side marked WF as shown in FIG. 19 or it could be incident on the side WB.

If ray A0 is incident at the same angle and with the same polarization, the transmitted light components T1, T2 etc should be the same for both schemes. This is evident when one inspects the terms in the series in expression 2, because each term (each of which corresponds to the intensity of a transmitted ray) is unchanged if one exchanges the subscript t for the subscript b. The exchange of subscripts is the mathematical equivalent of changing the surface that is illuminated from WF to WB. The consistency of transmitted light measurements for the two illumination conditions can be used to check that the measurement apparatus is functioning properly. However, if either of the wafer surfaces has any features that cause scattering of light, then the pattern of reflected or transmitted rays may be more complex, and the intensity measurements may become sensitive to the side that is illuminated. This may also be true if the bulk of the wafer can scatter light.

Although the transmitted ray components should be equivalent regardless of which surface is illuminated, the same is not true for the reflected light components. As a result, illumination of the surface WB, provides new information about the optical properties of the wafer. The reflectance of the wafer, when the wafer is illuminated on the front side, $R^*_{WF}$ is not necessarily equal to that when the back side is illuminated, $R^*_{WB}$. $R^*_{WF}$ is given by the equation 7 but $R^*_{WB}$ is given by the equation $$R^*_{WB} = R_{bv} + \frac{a^2 T_b^2 R_{ts}}{1 - a^2 R_{ts} R_{bs}}, \tag{12}$$

where $R_{bv}$ is the back surface reflectivity for radiation incident on it from outside the wafer.

Likewise, the various reflected light rays for front-side illumination, which we may designate as $R1_{WF}$, $R2_{WF}$, $R3_{WF}$, etc. do not necessarily match the corresponding rays for back-side illumination, designated as $R1_{WB}$, $R2_{WB}$, $R3_{WB}$, etc. The origins of this asymmetry become evident when one inspects the terms in the series of expression 4, because each term (each of which corresponds to the intensity of a reflected ray) is changed if one exchanges the subscript t for the subscript b. This asymmetry allows a measurement with back-side illumination to provide extra information about the optical properties of the wafer. In particular, we see that the first reflected ray $R1_{WB}$, can provide a measurement of the back surface reflectivity for radiation incident from outside the wafer, $R_{bv}$. Furthermore, measurement of the intensity of the second reflected ray, $R2_{WB}$, can provide a measurement of the quantity $a^2 T_b^2 R_{ts}$.

From this discussion it is clear that measurements of reflected and/or transmitted light components for the case of illumination from the front and back sides of the wafer can provide many useful pieces of information about the optical properties of the wafer. It should also be noted that it is also possible to extract information about the optical properties from measurements of the absorptance or the emittance of either or both surfaces of the wafer. These quantities are also generally not equal for the two sides of the wafer. The emittance of the front side of the wafer, $\epsilon_{WF}$, and its absorptance, $A_{WF}$, can be deduced from equation 8, which leads to equation 9, whereas the emittance of the back side of the wafer, $\epsilon_{WB}$, and its absorptance, $A_{WB}$, are given by $$\epsilon_{WB} = A_{WB} = 1 - S^* - R^*_{WB}, \tag{13}$$

which leads to the equation $$\varepsilon_{WB} = A_{WB} = 1 - R_{bv} - \frac{aT_b(T_t + aT_b R_{ts})}{1 - a^2 R_{ts} R_{bs}}. \tag{14}$$

Although the direct measurement of these quantities requires special instrumentation, it is possible. For example, the emittance at any given wavelength can be deduced by measuring radiation that is thermally emitted by the wafer. By comparing the strength of the thermal emission from the wafer to that from a black-body radiator at a temperature equal to that of the wafer, it is possible to deduce the emittance. Such measurements can be used to measure $\epsilon_{WF}$ and $\epsilon_{WB}$. The absorptance at a given wavelength can be measured by illuminating the wafer with a known intensity of radiation at that wavelength and observing how the temperature of the wafer changes over time. The increase in wafer temperature can be related to the absorptance of the wafer at the wavelength of interest. Such measurements can be used to determine $A_{WF}$ and $A_{WB}$.

Acquiring Information About Wafer Properties from Measurements

The measurements described in this disclosure can be used for various purposes, including characterization of the type of wafer being processed. For example, the optimal processing approach might require information about the substrate material, its doping, the wafer thickness and the reflectances and transmittances of the wafer for given ranges of wavelengths. Such information can then be used to predict the temperature dependence of the spectral emittance or absorptance, or the total emittance or absorptance. That information can then be used to improve the uniformity and repeatability of thermal processing and can also be used to optimize the control of the heating process for greatest time efficiency and hence best wafer throughput. Although information about the type of wafer being processed can be separately provided to the processing equipment, sometimes this is not convenient or the information is not available. In this case, an in situ determination of the desired properties, either immediately before processing or even during an early part of the processing, may be desirable.

For example, by obtaining an estimate of the internal transmittance, which is linked to the absorption coefficient $\alpha(\lambda,T)$, one can find out about the type of wafer being processed, because the material properties of the substrate affect its absorption spectrum, which is described by the wavelength dependence of $\alpha(\lambda,T)$. In principle, the type of wafer being processed can be identified through a measurement of its absorption spectrum. For example, the material that the substrate is made from can be identified by comparing the measured absorption spectrum to a set of absorption spectrum data for various materials. For example, if the wafer being processed was lightly-doped silicon, with a resistivity greater than 1 $\Omega$cm, the absorption spectrum displays a large decrease in absorption as the wavelength increases from 0.8 μm, where $\alpha(\lambda,T)$ at room temperature is ~850 cm$^{-1}$, to 1.2 μm, where $\alpha(\lambda,T)$ at room temperature is ~0.02 cm$^{-1}$. This sharp feature is often called the absorption edge, and its spectral location is linked to the magnitude of the minimum energy gap in the band structure of the material. Identification of such a characteristic feature in the absorption spectrum can help identify the wafer substrate as being made of silicon.

In contrast, if the wafer were made from germanium, the absorption edge feature would appear in the wavelength range near 1.8 μm. A similar approach can be used to distinguish the presence of other materials, such as GaAs, InP, InSb, GaSb, GaN, InN, SiC and diamond, because the absorption spectra of these materials also show an absorption edge. It can also be used to identify the presence of alloys of semiconductors, such as silicon-germanium alloys, or quaternary alloys of GaAs and InP. Analysis of the absorption spectra can even be used to deduce the composition of these alloys, such as the ratio of the Si to Ge content. In principle analysis of $\alpha(\lambda,T)$ can also be used to distinguish between various types of insulators and metals, as well as for semiconductors, because most materials display characteristic features in their absorption spectra.

For example, many materials display absorption features that arises as a consequence of transitions of electrons between energy levels. Such features typically arise at wavelengths in the ultra-violet (UV), visible and near-infra-red parts of the electromagnetic spectrum. Many materials also display absorption features linked to vibration of atomic species about their mean positions. Such features typically arise at infra-red wavelengths. A comparison of a measured absorption spectrum with reference information about the spectral positions of absorption edges, electronic transitions and vibrational absorption features can be used to identify the material being processed. It is important to realize that absorption phenomena can affect reflected light intensity as well as transmitted light intensity, and measurement of either can be used to deduce information about the absorption spectrum. Furthermore, in the case of opaque surfaces, analysis of the reflection spectrum can also provide similar information.

The absorption spectrum can also be used to determine the state of doping of the wafer. For example, the presence of electrically active dopants results in the phenomenon of free-carrier absorption. The free-carrier absorption results from interaction of electromagnetic radiation with charge carriers that can move through the semiconductor lattice. The strength of the absorption depends on the concentration of free carriers. In semiconductors the free carriers can be electrons or holes, depending on the nature of the doping. In an n-type semiconductor, the dominant charge carriers are electrons, whereas in a p-type semiconductor the dominant charge carriers are holes. The wavelength and temperature dependence of free-carrier absorption can be estimated from theoretical or empirical models. Such models can also include other effects of doping on the absorption spectrum, such as the band-gap narrowing in heavily doped semiconductors, and absorption associated with transitions between bands. By collecting information about the absorption spectrum and analyzing the spectrum with a model, it is possible to determine the type of the carriers (electrons or holes) and their concentration. This information can then be used to predict the behavior during the semiconductor manufacturing step.

As well as providing information about the substrate, the measurements of optical properties can provide information about surface coatings and patterns on the wafer. The wafer may be coated on both the front and the back side. These coatings may be made up of a stack of several films. They may also be laterally patterned to form various device features, and there may also be trench-like features and other non-planar structures present. Typically the device features would be on the front side of the wafer, previously referred to as WF. The optical measurements described in this disclosure may also help characterize the nature of the features and layers present near the surfaces of the wafer. The information gained from that characterization can then be used to improve process control during the semiconductor manufacturing step. Here, the ability to discriminate between front and back surface reflections can be useful in forming a more complete understanding of the nature of the films and structures on either surface of the wafer. Both reflected light and transmitted light measurements can be affected by the optical properties of the two surfaces of the wafer, as will be discussed further below.

Comparison of the various reflected and transmitted light measurements can help to identify whether at any given wavelength the films on either surface are transparent or opaque, and whether the substrate is transparent or opaque. For example, if the films on the wafer surface are opaque, i.e. $T_f=0$, as may be the case if the wafer is coated with a metal layer, then the front surface reflectance $R^*_{WF}=R1_{WF}$ and the higher order reflections, $R2_{WF}$, $R3_{WF}$ etc are all zero. In this case both the transmittance, $S^*$, and all the transmitted light components T1, T2 etc. are also zero. However, if the substrate is not opaque, i.e. $a \neq 0$, and the back surface layers are not opaque, i.e. $T_b \neq 0$, then the back surface reflectance $R^*_{WB} \neq R1_{WB}$ and $R1_{WB} \neq 0$. Hence a comparison of reflected light components for front and back surface illumination can help identify whether the films on one of the surfaces of the wafer are opaque. If we find that for one surface the reflectance is the same as the surface reflectivity, whereas for the other surface this does not hold, then it is likely that the former surface includes an opaque film. One should note that if the back surface reflectivity $R_{BS}=0$, then the front surface reflectance would also equal its reflectivity because there would be no secondary reflections, but in this case the transmittance would not be zero, unless the front surface happened to be a perfect reflector. Such circumstances are unlikely to arise in practice. The approach can be equally well applied to finding opaque films on the front or back surfaces of the wafer. Other measured quantities can be analyzed with the same purpose. For example, if the transmittance, S* or the first transmitted light component, T1, is zero, and yet the back surface reflectance $R^*_{WB} \neq R1_{WB}$ and $R1_{WB} \neq 0$, then we can deduce that the front surface is opaque.

If the wafer substrate is opaque, then a=0 and the reflectance of each surface of the wafer is equal to its reflectivity, i.e. $R^*_{WF}=R_{tv}$ and $R^*_{WB}=R_{bv}$. Furthermore the reflected light components $R2_{WF}$, $R3_{WF}$, etc. and $R2_{WB}$, $R3_{WB}$ etc. are zero. Furthermore, the transmittance, S*=0, and all the transmitted light components T1, T2, etc are also all zero. Hence an analysis of these components of reflected or transmitted energy can be used to deduce whether the substrate material is opaque at any given wavelength. However, we should note that the same conditions (i.e. $R^*_{WF}=R_{tv}$, $R^*_{WB}=R_{bv}$, S*=0, T1=0, T2=0 etc.) may arise if the films on both surfaces are opaque, i.e. if both $T_t=0$ and $T_b=0$, even if the substrate itself is transparent, i.e. a≠0.

Another test that can be applied to determine whether a surface of the wafer contains an absorbing film is to test whether its reflectivity is the same for radiation incident from within the substrate as for radiation incident from outside the substrate, e.g. if $R_{tv} \neq R_{ts}$, then the top surface of the wafer contains an absorbing film. Furthermore if $R_{tv} \neq (1-T_t)$ then the top surface contains an absorbing film. Analogous rules can be applied to characterize the back surface of the wafer.

If the top and bottom films are all transparent and the wafer is also transparent, then a special case arises, where the reflectance is equal for light incident from either side of the wafer. In this case $$R^*_{WF} = R^*_{WB} = \frac{R_{tv} + R_{bv} - 2R_{tv}R_{bv}}{1 - R_{tv}R_{bv}}. \tag{15}$$

As a result, a simple test of whether a wafer and all its coatings are non-absorbing is to check if $R^*_{WF}=R^*_{WB}$.

By selecting the wavelength range where such diagnostic tests are performed, different aspects of the wafer's characteristics can be probed. For example, by choosing a wavelength range in the infra-red region such as 1.55 μm, if it is detected that the wafer shows an appreciable absorption coefficient, e.g. greater than 1 cm$^{-1}$, then the wafer must be heavily doped, e.g. with a resistivity below 0.1 Ωcm. The exact criterion for definition of the appropriate absorption level depends on the wavelength, in a manner that can be determined from the model for the effect of doping on optical absorption. For any test it is better to perform the measurement at several wavelengths, in order to reduce the possibility that an unusual combination of surface reflectivities or some other condition produces a false result. The tests can also be performed using a broadband light source that delivers light over a range of wavelengths if desired.

Determination of Absorption Coefficient of the Substrate

In order to deduce the value of $\alpha(\lambda,T)$, it is usually necessary to deduce the internal transmittance given by equation 1. The internal transmittance may be obtained by measurement of any of the reflected or transmitted light components illustrated in FIG. 19, or from analogous components obtained from measurements where the surface WB is illuminated. However, in general it is also necessary to know other properties of the wafer. For example, by rearranging expression 7, "a" is given by the expression $$a = \sqrt{\frac{R^*_{WF} - R_{tv}}{\{(R^*_{WF} - R_{tv})R_{ts} + T_t^2\}R_{bs}}}. \tag{16}$$

Hence, in order to obtain a value for a, $R^*_{WF}$, $R_{tv}$, $R_{ts}$, $T_t$ and $R_{bs}$ should be known. Although these quantities may be known from other measurements or calculations, in general they are unknown. The method described in this disclosure can help to improve the estimate of a, because a value for the first surface reflection $R_{tv}$ can be established, by measuring the reflected light component R1. The reflectance $R^*_{WF}$ can also be established by conventional means. In many cases of practical importance the methods of this disclosure can further provide complete characterization of the optical properties of interest, including an accurate determination of the internal transmittance, and hence of the absorption coefficient $\alpha(\lambda,T)$.

The internal transmittance can also be obtained from transmitted light measurements. Rearranging the expression 6, the expression following is obtained:

$$a = \frac{-T_t T_b + \sqrt{T_t^2 T_b^2 + 4R_{ts}R_{bs}(S^*)^2}}{2R_{ts}R_{bs}S^*}. \tag{17}$$

Here, in order to obtain a value for a, S*, $T_t$, $R_{ts}$, $T_b$ and $R_{bs}$ need to be known. Once again, these quantities may be known from other measurements or calculations, but in general they are unknown. Values for the internal transmittance can also be derived from measurements of specific components of the reflected or transmitted radiation. For example, as shown above, the ray T1 has intensity $I_{T1}$, given by $aT_t T_b I$. Hence, the internal transmittance is deduced from the expression $$a = \frac{I_{T1}}{T_t T_b I}. \tag{18}$$

The internal transmittance can be obtained from a measurement of the intensity of the ray R2, $I_{R2}$, which has an intensity $a^2 T_t^2 R_{bs} I$. Hence, the internal transmittance can be deduced from the expression $$a = \sqrt{\frac{I_{R2}}{T_t^2 R_{bs} I}}. \tag{19}$$

The internal transmittance can also be obtained from a measurement of the ratio of the intensities of successive reflected or transmitted rays, because each of the successive transmitted or reflected rays that emerge from the substrate will be further attenuated relative to the previous one. The attenuation arises as a result of two passages through the substrate and as a result of a reflection from the top surface and from the bottom surface, so that each ray decreases in intensity by a factor of $a^2 R_{ts} R_{bs}$, relative to the previous ray. Hence if the intensity of ray R3 is $I_{R3}$, then the ratio of $I_{R3}$ to $I_{R2}$, K, is given by $K = I_{R3}/I_{R2} = a^2 R_{ts} R_{bs}$, and we can deduce a from $$a = \sqrt{\frac{K}{R_{ts}R_{bs}}}. \quad (20)$$

A similar approach can be used for the ratio of successive transmitted rays, such as T1 and T2 etc.

The Case where Surface Coatings do not Absorb Radiation

The case where neither the top nor bottom surface of the wafer contains absorbing films is of special interest. In this situation $T_t=1-R_{tv}$, $T_b=1-R_{bv}$, $R_{tv}=R_{ts}$ and $R_{bv}=R_{bs}$. This allows us to rearrange the expressions for reflectances and transmittance in terms of quantities that we can measure using the methods described in this disclosure, including the first surface reflectivities, $R_{tv}$ and $R_{bv}$, which can be obtained from $R1_{WF}$ and $R1_{WB}$ respectively. The expressions are $$R^*_{WF} = R_{tv} + \frac{a^2(1-R_{tv})^2 R_{bv}}{1-a^2 R_{tv} R_{bv}}. \quad (21)$$

Likewise, the reflectance of the wafer for light incident from the back side is given by $$R^*_{WB} = R_{bv} + \frac{a^2(1-R_{bv})^2 R_{tv}}{1-a^2 R_{tv} R_{bv}}. \quad (22)$$

The transmittance is given by $$S^* = \frac{a(1-R_{tv})(1-R_{bv})}{1-a^2 R_{tv} R_{bv}}. \quad (23)$$

Any of these expressions 21, 22 or 23 can be used to deduce the internal transmittance, and hence to determine the absorption coefficient of the substrate $\alpha(\lambda,T)$, from the measured quantities. For example, rearranging 21, the following expression is obtained $$a = \sqrt{\frac{R^*_{WF} - R_{tv}}{\{(R^*_{WF} - R_{tv})R_{tv} + (1-R_{tv})^2\}R_{bv}}}. \quad (24)$$

The method described in this disclosure can be used to deduce all the quantities in the expression on the right hand side of equation 24, and hence can be used to make an accurate determination of the internal transmittance. The reflectance, $R^*_{WF}$, can be obtained by conventional means, and the reflectivity $R_{tv}$ and the reflectivity $R_{bv}$ can be determined by the method described in this disclosure. For example, by illuminating the front surface of the wafer and collecting only the light reflected one time at the front surface of the wafer, the reflectivity $R_{tv}$ can be deduced. Then, by illuminating the back surface of the wafer and collecting only the light reflected one time at the back surface of the wafer, the reflectivity $R_{bv}$ can be deduced. Having measured $R^*_{WF}$, $R_{tv}$ and $R_{bv}$, the internal transmittance from equation 24 can be calculated. The internal transmittance can also be deduced from an analogous approach where the back surface reflectance $R^*_{WB}$, is measured in combination with the use of equation 22. Furthermore, the internal transmittance can be deduced from a measurement of the transmittance S*. In the latter case, the internal transmittance is obtained from the expression $$a = \frac{-(1-R_{tv})(1-R_{bv}) + \sqrt{(1-R_{tv})^2(1-R_{bv})^2 + 4R_{tv}R_{bv}(S^*)^2}}{2R_{tv}R_{bv}S^*}, \quad (25)$$

obtained by rearranging equation 23. Once again, once the transmittance S* is obtained, and the reflectivities $R_{tv}$ and $R_{bv}$ are obtained, equation 25 can be used to deduce the internal transmittance. Likewise, the internal transmittance can be obtained from measurements of the transmitted ray, T1 and using the expression $$a = \frac{I_{T1}}{(1-R_{tv})(1-R_{bv})I}, \quad (26)$$

obtained by rearranging equation 18. The internal transmittance can also be obtained by measuring the intensity of the reflected ray, R2 and using the expression $$a = \sqrt{\frac{I_{R2}}{(1-R_{tv})^2 R_{bv} I}}, \quad (27)$$

obtained by rearranging equation 19. The internal transmittance can be obtained by measuring the ratio of the intensities of successive reflected or transmitted rays and using the expression $$a = \sqrt{\frac{K}{R_{tv}R_{bv}}}, \quad (28)$$

obtained by rearranging equation 20.

In summary, for the case where the films on both the front and the back of the wafer are non-absorbing, the method of this disclosure allows an accurate determination of the absorption coefficient of the substrate material. In cases where the films are absorbing, further measurements or modeling may be needed to reach a sufficiently accurate determination of the absorption coefficient. However, the case where surface films are non-absorbing is of practical importance, because this condition arises in important practical applications, such as oxidation or deposition processes performed early on in the device fabrication sequence, and also in some annealing processes on semiconductor wafers, such as ion implantation damage annealing. In such processes, the surface films are frequently relatively transparent, at least for wavelengths in the infra-red. Furthermore, in many cases where there are patterned films present on the wafer and even if these films themselves are absorbing, the patterning means that the absorbing film only partly cover the surface of the wafer and hence it allows the transmission of a significant fraction of the incident radiation into the substrate. It should be understood that the analysis for the case of non-absorbing films may still be reasonably accurate even if the surface films do show some absorption, provided that the internal transmittance, a, is rather small, as compared to the transmissivity of either the front or back surface of the wafer, $T_t$ and $T_b$. The success of the approach can depend on the strength of the absorption in any surface layers and/or the degree of surface coverage. Hence the approach may even be used in situations where there are absorbing films present, such as metals, silicides or heavily doped semiconductor regions, provided that the degree of absorption introduced by these features is small relative to that introduced by the propagation of radiation through the substrate to the opposite surface. Typically wafers do not have thick layers of absorbing material present on their back surfaces, so that it is often reasonable to assume that the back surface is non-absorbing.

Figure 20:
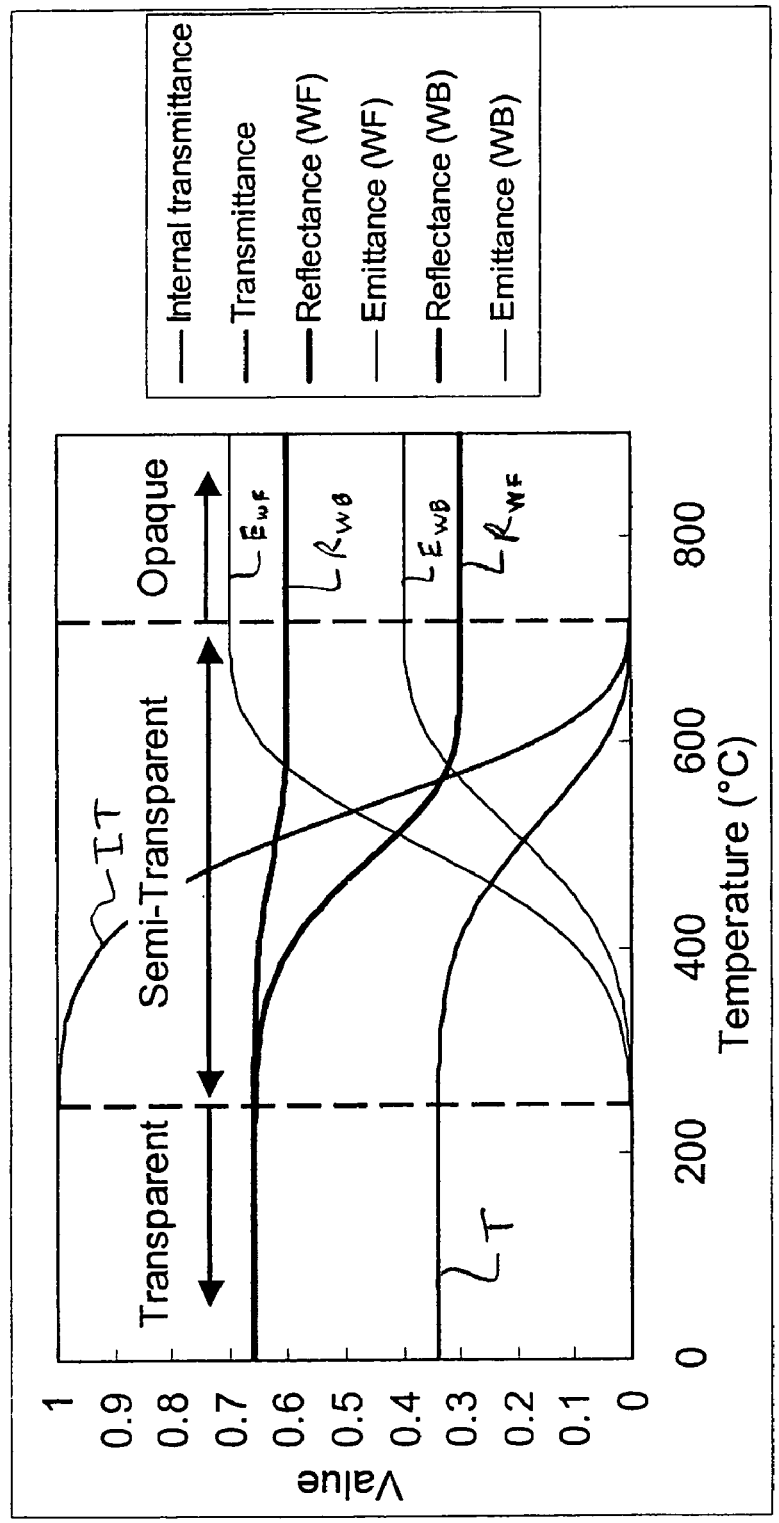
FIG. 20 is a graphical illustration of the temperature dependence of optical properties of a wafer where the substrate has a temperature-dependent absorption coefficient.

FIG. 20 shows an example of the temperature dependence of some optical properties of a slab of material at a wavelength $\lambda$. In the example, the absorption coefficient of the material that makes up the bulk portion of the slab (usually referred to as the substrate), $\alpha(\lambda,T)$ varies with temperature. As a result, the internal transmittance, also changes with temperature. In the following discussion, the methods of this disclosure are further described in detail to show how they can be used to predict optical properties as a function of temperature. The approach used relies on the combination of low temperature measurements of the surface reflectivities with a model for the optical absorption of silicon.

In the example shown, the case considered is that for a silicon wafer that is lightly doped. In this instance, lightly doped means that the resistivity is greater than ~1 $\Omega$cm. The wafer considered has a thickness of 775 μm, which is typical for a 300 mm diameter silicon wafer as used in semiconductor device manufacturing. In this example, the reflectivity of the front surface of the wafer is $R_{fv}$=0.3, and the reflectivity of the back surface of the wafer is $R_{bv}$=0.6, and it is assumed that the reflectivities of these two surfaces do not change with temperature and that there are no absorbing films present at the surfaces. The optical properties are calculated as functions of temperature, for a wavelength of 2.3 μm. In this example, the calculation is performed for radiation incident on the wafer at normal incidence or emitted from the wafer at normal incidence. The quantities calculated were the reflectance of the front of the wafer, $R^*_{WF}$, and the back of the wafer, $R^*_{WB}$, the transmittance of the wafer, $S^*$, and the emittance of the front of the wafer, $\epsilon_{WF}$, and of the back of the wafer, $\epsilon_{WB}$. These quantities were obtained from the combination of equations 6, 7, 9, 12 and 14 above. All these quantities are functions of wavelength and temperature, and in this example, the temperature dependence arises because the internal transmittance is a function of temperature. The temperature dependence of internal transmittance arises because of the temperature dependence of the absorption coefficient, $\alpha(\lambda,T)$. For the calculations shown here $\alpha(\lambda,T)$ for the wavelength of 2.3 μm was obtained from the model given by Vandenabeele and Maex in J. Appl. Phys. 72, 5867 (1992). In general, the model used to deduce $\alpha(\lambda,T)$ can be any theoretical or empirical model for the wavelength and temperature dependence of the absorption coefficient of the material of interest. For example, for lightly doped silicon, the model for optical absorption described by Rogne et al. in Appl. Phys. Lett. 69, 2190 (1996) provides a way to calculate $\alpha(\lambda,T)$ for wavelengths between ~1 and ~9 μm, for temperatures between room temperature and ~800° C. Timans provides data and models for optical absorption and refractive indices of both lightly and heavily doped silicon in the chapter "The Thermal Radiative Properties of Semiconductors" in the book "Advances in Rapid Thermal and Integrated Processing", edited by F. Roozeboom (Kluwer Academic Publishers, Dordrecht, Netherlands, 1995) p. 35. Such models can provide estimates for a wide range of wavelengths, from the visible region where $\lambda$~0.5 μm through to the far infrared, where $\lambda$~30 μm. The models described can also take account of the substrate doping conditions, such as the doping concentration, or other information about the concentrations of electrons and holes in the substrate. Other suitable models have been described in the literature, including models such as the Drude model for free-carrier absorption, which can be used to estimate the effect of electron and hole concentrations on infra-red absorption.

The other information that is needed for the predictions of optical and thermal properties is the thickness of the wafer. Depending on the accuracy needed in the prediction, the thickness can either be estimated as an appropriate thickness for the wafer size being processed, it can be provided as an input parameter by the user, or it can be measured either manually or automatically within the tool.

In the example shown, $\alpha(\lambda,T)$ at 2.3 μm is very low at low temperatures, for example it is estimated to be <$10^{-6}$ cm$^{-1}$ at room temperature. Under this condition, a≅1. In contrast, at high temperature, $\alpha(\lambda,T)$ is large, for example it is ~100 cm$^{-1}$ at 730° C. In that case, a≅0.00054. As the temperature rises further the internal transmittance tends towards zero, and the wafer becomes opaque. The figure shows how the internal transmittance remains ~1, and the substrate is effectively transparent, for temperatures below ~250° C., but as the temperature rises the internal transmittance decreases, until at temperatures >750° C., the wafer is effectively opaque. In the interval between 250 and 750° C., the wafer can be said to be semi-transparent.

At low temperatures, where the wafer is transparent, the transmittance $S^*$=0.34, but this falls towards zero as the temperature rises, becoming <$10^{-4}$ for temperatures >750° C. At low temperature, the reflectance for light incident on the front surface equals the reflectance for light incident on the back surface, as expected from equation 15 above. In the example, at room temperature $R^*_{WF}$=$R^*_{WB}$=0.66. However, as the temperature rises, both $R^*_{WF}$ and $R^*_{WB}$ decrease and they cease to be equal. The decrease occurs because the increasing absorption within the substrate reduces the contribution of light reflected at the second surface (opposite the surface that is illuminated) to the reflectance. When the substrate becomes effectively opaque, then the reflectances equal the corresponding reflectivities of the illuminated surfaces, so that $R^*_{WF}$=$R_{fv}$=0.3 and $R^*_{WB}$=$R_{bv}$=0.6. The emittances of the slab as observed from the two opposite sides are both zero at low temperature, when the wafer is transparent. This is consistent with the fundamental principle that objects that cannot absorb radiation also cannot emit radiation. As the temperature rises and the wafer becomes semitransparent, the emittances also increase, until at the point where the wafer is effectively opaque, they equal the corresponding emissivities of the surfaces, so that $\epsilon_{WF}$=1−$R_{fv}$=0.7 and $\epsilon_{WB}$=1−$R_{bv}$=0.4.

This example shows how the present disclosure can provide estimates of emittances, or the equivalent absorptances, at elevated temperatures. In principle, these quantities can be deduced during heating, for example by making real-time measurements of $R^*_{WF}$ and $S^*$ within the process chamber and then calculating $\epsilon_{WF}$ from equation 8. However, in some circumstances it can be difficult to perform an accurate measurement within the chamber. In contrast, the method of this disclosure allows a determination of any of the properties of the wafer in a convenient location outside the process chamber. This can then be combined with knowledge of the trend of $\alpha(\lambda,T)$ with temperature, and knowledge of the thickness of the wafer to make a prediction of the emittance or absorptance of the wafer during processing. In this example, a measurement of $R_{bv}$ at room temperature can be enough to ensure the determination of an appropriate value for $\epsilon_{WB}$ when the wafer is at T>750° C., inside the process chamber. The information on emittance can be used to correct the readings of a pyrometer in order to determine the temperature of the wafer. The modeling approach can also be used to predict the temperature dependence of the spectral absorptances of the wafer as functions of temperature. This information can be provided to a control algorithm in order to improve the control of the heating process, for example by providing improved estimates of the power coupling between the wafer and a lamp heating energy source, or by providing an improved estimate of the radiated energy heat loss from the wafer.

Figure 21:
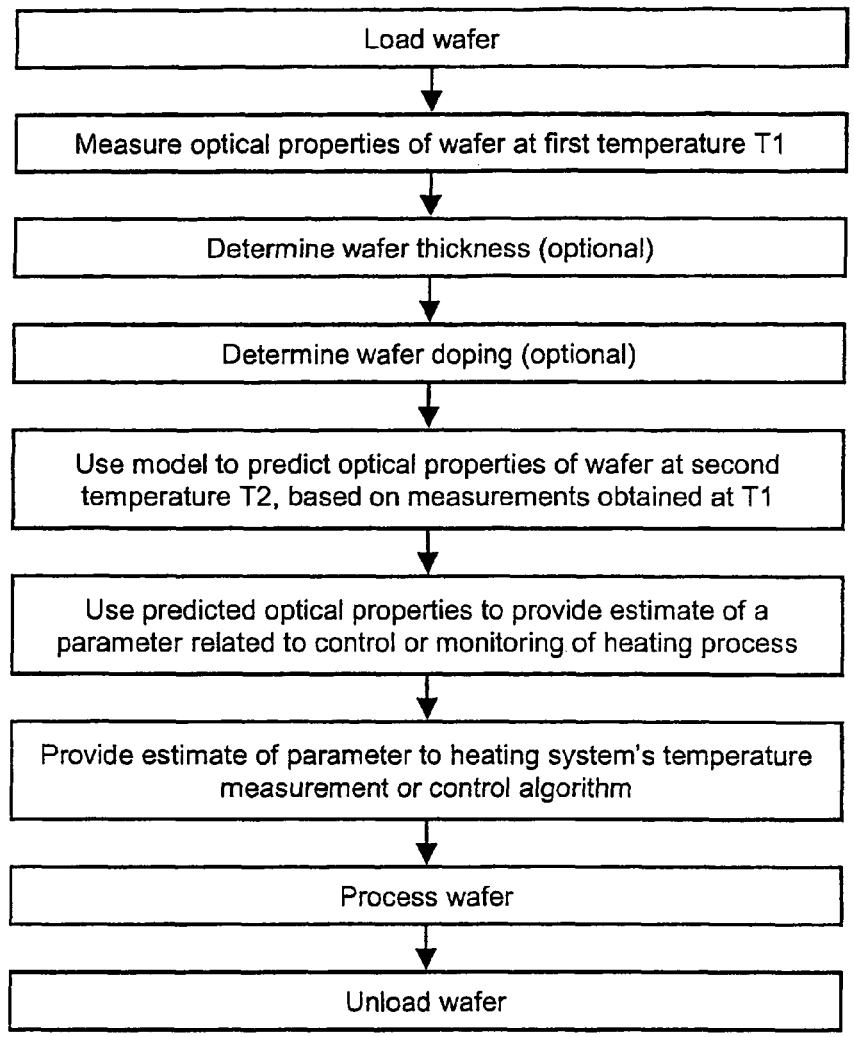

The flow chart in FIG. 21 shows one embodiment of how to perform the method of this disclosure. The first step is to load the wafer to a position where an optical measurement can be performed. In the next step the optical properties are measured with the wafer at an initial temperature, T1. The initial temperature may be near room temperature. The optical properties can be any of those mentioned in this disclosure. They can be measured using an approach that involves illuminating either surface of the wafer. The next step, which is optional, involves determining the wafer's thickness. This determination can be through a measurement or by collecting the information from an external input of that data. Various means of wafer thickness measurement could be used here, such as an optical, electrical or mechanical measurement. Usually it is best to perform the thickness measurement with a probe that does not touch the wafer surface, in order to prevent surface damage or contamination, especially on the surface of the wafer where the electronic devices are to be fabricated. For example, the thickness of the wafer can be measured by using an infrared interferometer. The thickness can also be measured by using optical probes to make accurate simultaneous measurements of the front and back surface positions and then determining the distance between them. In this case the wafer need not be transparent at the optical wavelengths employed by the probes. The optical probes can be based on methods of optical interferometry or they could be based on methods of laser triangulation. The wafer thickness can also be measured by electrical capacitance displacement probes. It can also be measured by using air gauges that determine dimensions by sensing the impact of the location of surfaces on gas flow behavior. It can also be determined by weighing the wafer, and using estimates of the wafer's area and its density to deduce the thickness. In some cases, if the coatings on the wafer surfaces have a substantial thickness themselves, it may be necessary to take their thickness into account when determining the thickness of the substrate itself. This could be done by subtracting the thickness of the coatings from a measurement of the thickness of the wafer that includes such coatings.

The next step, which is also optional, involves determining the wafer's doping. This determination can also be through a measurement or by collecting the information from an external input of that data. If the doping needs to be determined, typically this may require optical or electrical measurement. As was pointed out above, the methods described in this measurement may be used to help determine the nature of the substrate doping. The information on doping can include the type of the doping, e.g. whether the wafer substrate is n-type or p-type material. It can also include the resistivity of the substrate. It can also include the species used to dope the substrate and the concentration of the dopant in the substrate. It can also include the concentration of electrons or holes in the substrate. Other methods of determining doping can include direct electrical measurements using contact or non-contact probes. Non-contact probes would generally be preferred, in order to prevent surface damage or contamination. Non-contact probing methods can include sensing of eddy currents induced in the substrate by an oscillating electric or magnetic field applied to the wafer.

Other information can also be provided concerning the nature and properties of the wafer. For example, information provided can include the nature of the substrate of the wafer, such as whether the wafer is silicon, gallium arsenide, germanium etc. It can also include information about the nature of films on the wafer, such as the thicknesses, materials and properties of thin films present on either surface of the wafer. It can also include information about the nature of patterns present on the wafer surfaces. Other properties that can be provided can also include the thermal properties, such as the thermal conductivity, thermal diffusivity or specific heat capacity. Measurements of thickness and doping are described as being optional because for some simple predictions of optical properties, it is not necessary to know these quantities with a high degree of accuracy. However, a measurement of wafer thickness can also be useful for various purposes of improved process control. For example, the thermal mass of the wafer depends on its thickness. As a result, the heating or cooling rate of the wafer is affected by the wafer's thickness. A determination of wafer thickness can help to improve the control of heating or cooling of the wafer. For example, the information about the wafer's thickness can be provided to a control algorithm that is used to set the heating power. This may also be helpful for controlling the process if the heating is open-loop i.e. without feedback control from a temperature sensor monitoring the wafer's temperature. The information can be used irrespective of the type of heating being employed, and can be employed when the wafer is heated by electromagnetic radiation, or by thermal conduction or by gas convection. For example it can be used to improve control in a system where the wafer is heated by a hot-plate or susceptor. By knowing the wafer thickness accurately it is easier to predict the evolution of wafer temperature after it is loaded onto a hot-plate. In this case, the improvements in control can be attained even without any measurements of optical properties of the wafer. Such improvements may be useful especially in cases where the wafer is predominantly heated by thermal conduction. In that situation optical properties have less influence on heat transfer to and from the wafer, but the thermal mass of the wafer still has a strong effect on the heating cycle.

The next step is to use a model to predict the optical properties at least at one second temperature of interest, T2. In practice this can involve predicting the optical properties over a range of temperatures, i.e. establishing the temperature dependence of the optical properties. The optical properties can again be any of those discussed in this disclosure, such as the emittance, absorptance, reflectance, transmittance or any of the surface reflectivities or emissivities etc. These properties can be predicted at any wavelength or temperature of interest.

The model used can be based on the equations given in this disclosure, or another set of equations or an algorithm that allows the prediction of the optical properties. The input to the model includes at least one of the initial measurements performed at the first temperature, T1. It may also optionally include information on the wafer thickness and on the doping of the wafer. In the case where the information on the doping of the wafer is available, this can be used to predict how the optical absorption coefficient and/or the refractive index in the substrate varies with wavelength and/or temperature.

The next step involves using the information about the optical properties to estimate a parameter that is related to control of the heating process. Examples of parameters include the emittance of the wafer at a wavelength that is used by a pyrometer for sensing wafer temperature. In this case an improved estimate of the emittance can provide a more accurate temperature reading. The pyrometer may in general determine the wafer temperature based on a sensed value of the intensity of thermal radiation emitted by the wafer. The wafer emittance or reflectance may be supplied to an algorithm that calculates the wafer temperature based on this sensed value of the intensity of radiation emitted by the substrate. Many schemes for pyrometry have been described in the prior art. Approaches such as enhancing the emittance of the wafer by forming a reflective cavity confronting at least part of the wafer surface have been shown to help reduce the effects of emittance changes on temperatures determined by pyrometers. However, improved accuracy is possible if an initial estimate of the emittance is available. Other approaches for reducing the effect of emittance variation include methods where in situ optical measurements are used to measure the emittance of the wafer during processing. One such approach is the ripple pyrometer approach. In such methods, an initial estimate of the emittance can be used to improve the accuracy of the measurements. One important aspect here concerns the effect of stray light on the accuracy of measurements. Such light can be reflected from the wafer and then be detected by the pyrometer, introducing error in the temperature measurement. By having accurate estimates of the wafer reflectance, the amount of reflected stray light can be estimated more accurately and hence its effect can be taken into account in determining the wafer temperature. Furthermore, in cases where the wafer is semi-transparent, it is usually necessary to know both the transmittance and the reflectance of the wafer in order to determine the emittance of the wafer, for example from equations 8 or 13. The method of the current invention can also be used to determine transmittance and emittance as needed. The measurement of transmittance can also help to obtain estimates of the amount of stray radiation transmitted by the substrate, which can be taken into account when interpreting the sensed radiation in order to determine the temperature of the wafer.

In some cases, measurements of transmittance and/or reflectance can also be used to determine the wafer temperature. For example, if we know the temperature dependence of either of these quantities at a given wavelength then we can use an in situ measurement of either of them to determine the wafer temperature. The advantage of this approach is that it is no longer necessary to measure the radiation emitted by the wafer. Such an approach can also be made insensitive to stray light problems. It can also be applied at relatively low temperatures, where pyrometry can be very difficult because of the low intensity of thermally emitted radiation. The temperature dependence of reflectance or transmittance can be estimated using the methods described in this invention, even in cases where there is not a prior knowledge of the coating that may be present on either surface of the wafer. For example, the reflectivities of the front and back surface of the wafer can be obtained as described. The temperature dependence of the absorption coefficient of silicon can be obtained from a model as described earlier, and this can be combined with the measured reflectivities to provide estimates of the temperature dependence of the transmittance or reflectance as needed. Hence in this example, the parameter that is modeled is the temperature dependence of the transmittance or the reflectance.

The parameter may also be one that is used in a control algorithm that determines a setting for a characteristic of the heating system. That characteristic influences the energy delivered to the wafer or the energy that is lost from the wafer, and hence affects the temperature, the heating rate or the cooling rate of the wafer. These quantities may be affected across the whole of the wafer or they may be affected in a particular region of the wafer. In the latter case, the wafer temperature uniformity can be affected by alteration of the system characteristic. The characteristic of the system may be a process variable, such as the power or energy delivered by a heating lamp or energy beam, the temperature and position of a heat radiating element, the current or voltage applied to an electrical conductor, the magnitude of RF or microwave power, or the magnitude of a gas flow. Other examples of process variables include the composition of gases in the chamber and their pressure, direction of flow etc. The characteristic can also be a physical characteristic of the heating system, such as the position of a reflector, the reflectance of a reflector, the location and size of a heating beam of energy, the wavelength, angle of incidence or state of polarization of an beam of electromagnetic energy, the location of a heat source relative to the wafer position, the magnitude of the gap between a wafer and a hot-plate or between the wafer and a heat-sink etc.

The parameter supplied to the control algorithm can be any factor that influences the thermal response of the wafer. The control algorithm can be a model-based controller. For example the algorithm can predict desirable settings for process or system variables in order to keep the wafer temperature on a given heating cycle, and/or to maintain a desired degree of temperature uniformity within the wafer. The predictions can be based on a model of heat transfer phenomena occurring during the processing. Clearly, by providing better information about wafer properties to the model, it is possible to improve the fidelity of the model to reality and hence to obtain better estimates of the process or system variables. The control algorithm may operate in an open-loop mode, where the settings are predicted on the basis of the model. It may also operate in a closed-loop mode, where the algorithm is provided with feedback about the wafer condition from at least on sensor. In the latter case, the control algorithm may also use a model of the heat transfer phenomena to improve the selection of control settings. Indeed the algorithm can include a part that predicts approximate values for the control settings based on predictions from the model, and a second part that corrects those settings to take account of the information from the sensor.

As mentioned earlier, the parameter supplied to the controller can be a physical characteristic, such as the wafer thickness. In case where the wafers are heated by optical or thermal radiation or where the wafer loses heat by radiation, the optical properties of the wafer may also affect the thermal response. Hence the parameter may be an emittance, an absorptance, a reflectance or a transmittance. In general it can relate to any property that describes how a wafer emits, absorbs, reflects, transmits or scatters electromagnetic radiation. Earlier, the use of the methods of this disclosure were discussed to identify whether a wafer is heavily doped or lightly doped. Such information can be provided to the control algorithm, or can even be used to select an appropriate control algorithm that takes into account how heavily doped material is expected to couple to an energy source. A selection of a control algorithm can affect the heating recipe structure if desired. Likewise, if it is determined that the wafer has a metal coating on a surface, the control algorithm can take this factor into account. The algorithm can determine how energy is applied to the wafer, including what intensity to apply to which location on the wafer and for what duration. It can also determine whether to operate in an open-loop mode of heating or in a closed-loop mode of heating, where feedback from at least one sensor of wafer condition is used to control the process. In some cases, there may be a transition between closed-loop and open-loop modes of operation that is determined by a criterion selected on the basis of the premeasurements of wafer properties. For example, it may be determined that if the wafer is predicted to be sufficiently opaque at a given temperature then the readings from a temperature sensor are valid when the sensor reports that the wafer is at a temperature above a given temperature. In this case, the controller can select a closed-loop control approach once this given temperature is reached during the initial heat up step.

The next step is processing of the wafer. The parameter is used by the control or measurement algorithm to provide more accurate or repeatable or uniform treatment, or to provide a faster or more efficient way of processing. Typical processes can include thermal annealing, crystallization, alloying, sintering, oxidation, nitridation, film deposition, etching, and promotion of reactions between materials deposited on a wafer, or between materials on a wafer and a process gas.

The final step involves unloading the wafer.

Figure 22:
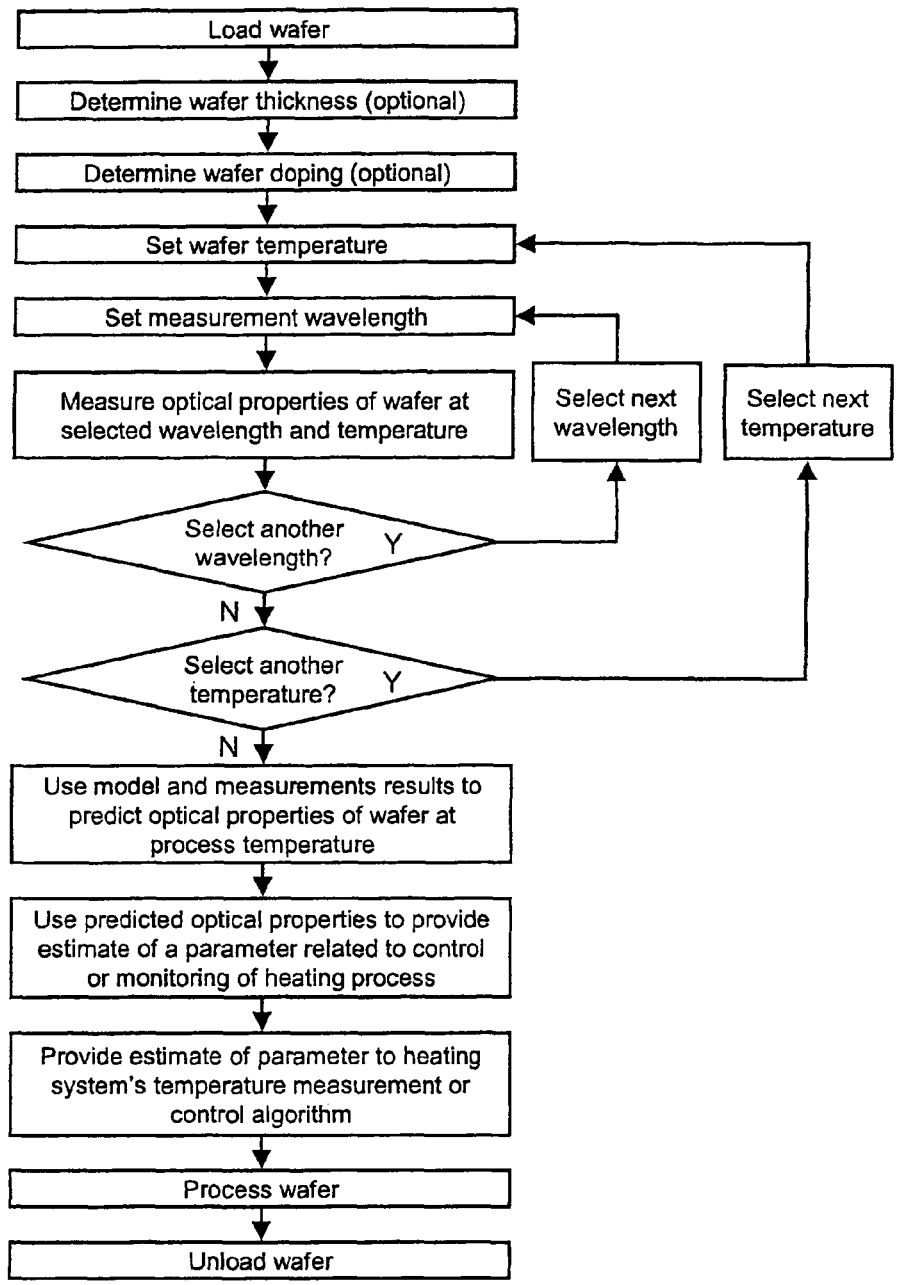

FIG. 22 shows another flow diagram for the present disclosure. In this case the diagram explicitly includes the possibility of measuring the optical properties at multiple wavelengths and multiple wafer temperatures. The information from such a set of measurements can be used in the prediction of optical properties of the wafer at a processing temperature.

FIG. 23 shows another flow diagram explicitly showing a step where an optical property of the wafer is determined using an approach where a particular component from the reflected or transmitted rays is selected for the measurement. This might be a group of rays such as the ray called R1 in FIG. 19, where the light has only been reflected from the first surface of the wafer. In that case the optical property that is determined could be the reflectivity of the front surface (WF), $R_{tv}$.

Figure 24:
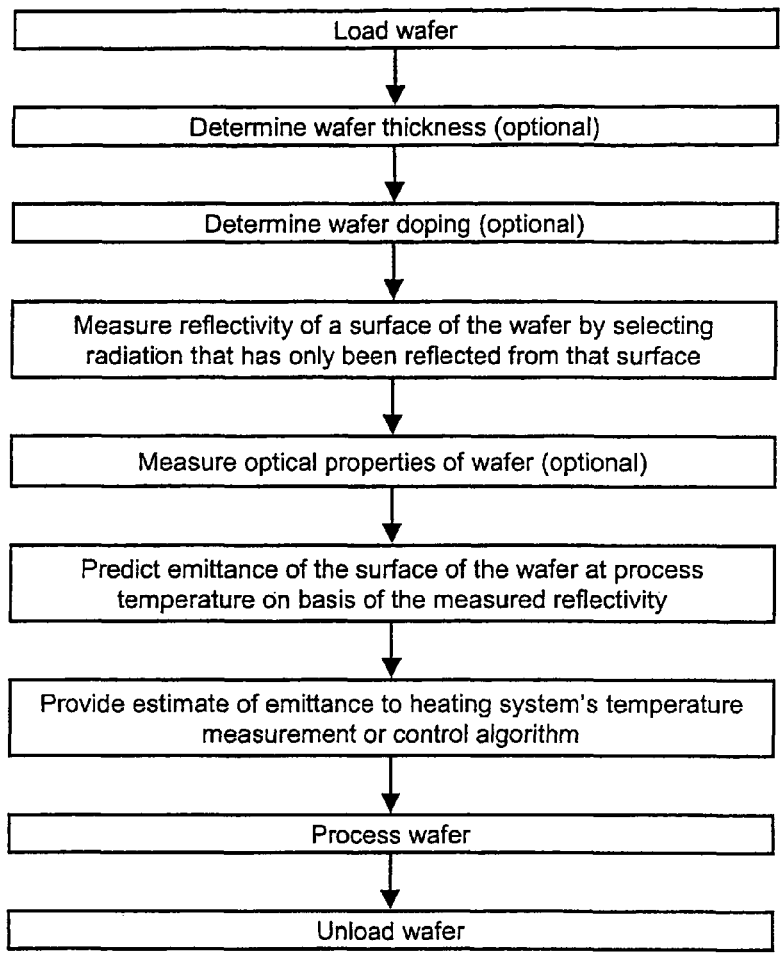

FIG. 24 shows an example, where the approach of measuring the reflectivity of a surface is used to predict an emittance at the processing temperature. The emittance value can be predicted with a very simple model, such as $\epsilon_{WF}=1-R_{tv}$. The emittance can be used to correct readings from a pyrometer. It can also be used to estimate power coupling to a heating energy source. It can also be used to estimate heat loss from the wafer surface. The determination of reflectivity and emittance can be made at a single wavelength, or it can be made over a range of wavelengths.

Figure 25:
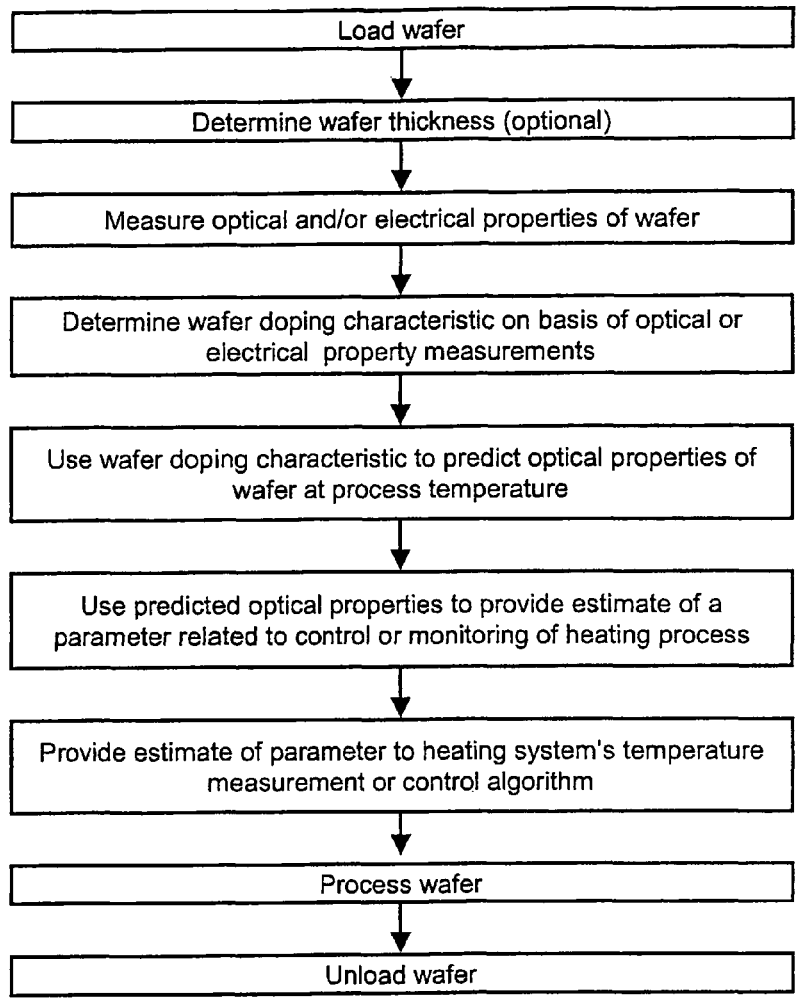

FIG. 25 shows another flow diagram illustrating an example where the pre-measurements are used to determine a doping characteristic of a wafer. The doping characteristic is then taken into account when making a prediction of an optical property at the process temperature. This optical property is then used to determine a parameter that is used for monitoring or controlling the process. The parameter can be a threshold temperature criterion for determining whether the temperature reading from a pyrometer is valid. It can also be a wafer emittance or absorptance. The parameter can also be a flag that tells the control system what kind of temperature measurement or control algorithm to use. It can also be used to determine what kind of temperature sensor to use. For example, if the wafer is determined to be heavily-doped (e.g. with a resistivity <0.1 Ωcm), then the system can chose to measure the wafer temperature with a pyrometer, for temperatures in a given range. On the other hand if the wafer is determined to be lightly doped (e.g. with a resistivity >0.1 Ωcm) the temperature can be measured by a sensor based on the transmission of infra-red light through the substrate. The determination of a doping characteristic can also be used to improve the accuracy of temperature measurement. For example, if an infra-red transmission measurement is used to determine wafer temperature, then knowledge about the doping characteristic of the wafer can be used to correct for the influence of wafer doping on infra-red transmission, and a more accurate estimate of the wafer temperature can be obtained.

Figure 26:
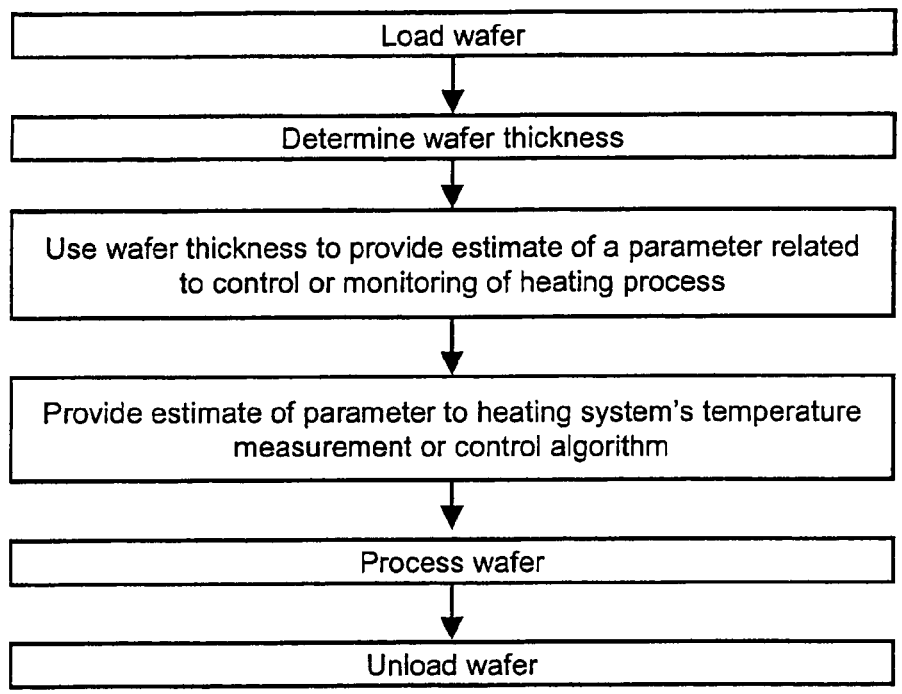

FIG. 26 shows another flow diagram, illustrating an example where information about wafer thickness is used to provide a parameter that is provided to the measurement or control system. The parameter can be the thickness itself. For example, a model-based controller may use the thickness information to predict the heating or cooling rate of the wafer. It may also use the thickness information to predict the time taken by the wafer to reach a given temperature. This approach can be used to improve the repeatability of heating processes. The wafer thickness can be provided as an input to the processing system or it can be measured by hardware in the processing system. The thickness information might also be used to predict optical properties of the wafer.

Any of the flow-diagram approaches or methods described in this disclosure can be combined as necessary.

These and other modifications and variations to the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention.

What is claimed:

1. A method for determining at least one optical characteristic of a substrate comprising:
    emitting light onto a first surface of a substrate, the substrate including the first surface and a second and opposite surface separated from the first surface by a thickness;
    directing the light through an optical pathway that includes at least one optical device separate from the substrate that separates the light reflected from the first surface from light reflected from the second surface; wherein the optical device comprises a focusing device having a focal length sufficient to at least partially separate the path of the light reflected from the second surface from the path of the light reflected from the first surface;
    detecting the amount of light reflected from the first surface; and
    based on the amount of detected light reflected from the first surface, determining at least one optical characteristic of the substrate, the characteristic comprising a reflectivity, an emissivity, absorptivity, or a transmissivity of the first surface, or a reflectance, an emittance, an absorptance, or a transmittance of the substrate, or mixtures of any of the above.

2. A method as defined in claim 1, wherein the at least one optical characteristic of the substrate is determined in a thermal processing chamber that heats the substrate.

3. A method as defined in claim 1, wherein the substrate comprises a semiconductor wafer and wherein at least one system component of a semiconductor wafer processing system is controlled based upon the at least one optical characteristic.

4. The method as defined in claim 1, wherein the method comprises directing the light through an optical pathway that separates the light reflected from the first surface from the light specularly reflected from the second surface.

5. A method as defined in claim 1, wherein the optical characteristic of the substrate is determined at a specific light wavelength range.

6. A method as defined in claim 5, wherein the specific light wavelength range comprises a wavelength at which a radiation sensing device operates that is used to measure a temperature of the substrate.

7. A method as defined in claim 5, wherein the light wavelength range substantially overlaps with a wavelength range of electromagnetic radiation that is used to heat the substrate.

8. A method as defined in claim 1, wherein after the at least one optical characteristic of the substrate is determined, the substrate is placed in a thermal processing chamber and heated, and wherein at least one system component is controlled during the heating process based on the at least one optical characteristic.

9. A method as defined in claim 8, wherein the system component comprises a temperature measurement system that includes a radiation measuring device that senses the amount of radiation being emitted by the substrate during heating for determining a temperature of the substrate, the amount of detected light from the first surface being used to determine an emittance value for the substrate for use in determining the temperature of the substrate in conjunction with the amount of radiation being sensed by the radiation measuring device.

10. A method as defined in claim 8, wherein the system component comprises a heating system including a power controller for a heating device that is used to heat the substrate, the amount of detected light from the first surface being used to adjust the power controller and thereby selectively increasing or decreasing the amount of energy being used to heat the substrate.

11. A method as defined in claim 8, further comprising the step of:
  detecting the amount of light reflected from the second surface of the substrate; and
  wherein the system component comprises a temperature measurement system that includes a radiation measuring device that senses the amount of radiation being emitted by the substrate during heating for determining a temperature of the substrate, the amount of detected light from the first surface and the amount of detected light from the second surface being used to determine emittance, transmittance, reflectance, or combinations thereof for the substrate for use in determining the temperature of the substrate in conjunction with the amount of radiation being sensed by the radiation measuring device.

12. A method as defined in claim 1, wherein the optical pathway includes at least two optical devices.

13. A method as defined in claim 12, wherein the at least two optical devices comprises a first lens and a second lens.

14. A method as defined in claim 12, wherein the at least two optical devices comprise lenses, mirrors, or mixtures thereof.

15. A method for determining at least one optical characteristic of a substrate comprising:
  emitting light onto a first surface of a substrate, the substrate including the first surface and a second and opposite surface separated from the first surface by a thickness;
  directing the light through an optical pathway that includes at least one optical device separate from the substrate that separates light reflected from the first surface from light reflected from the second surface;
  detecting the amount of light reflected from the first surface; and
  based on the amount of detected light reflected from the first surface, determining at least one optical characteristic of the substrate, the characteristic comprising a reflectivity, an emissivity, absorptivity, or a transmissivity of the first surface, or a reflectance, an emittance, an absorptance, or a transmittance of the substrate, or mixtures of any of the above;
  wherein the optical pathway includes a first optical device and a second optical device which direct the light onto a particular location of the first surface of the substrate, the light reflecting off the first surface then once again passing through the second optical device; after passing through the second optical device, the light is reflected off a third optical device and contacts a fourth optical device so as to be focused onto a light detector.

16. A method as defined in claim 15, wherein the first, second, third, and fourth optical devices comprise lenses, mirrors, or mixtures thereof.

17. The method as defined in claim 15, wherein the at least two optical devices comprise lenses, mirrors, or mixtures thereof.

18. A method for determining at least one optical characteristic of a substrate comprising:
  emitting light onto a first surface of a substrate, the substrate including the first surface and a second and opposite surface separated from the first surface by a thickness;
  directing the light through an optical pathway that includes at least one optical device separate from the substrate that separates light reflected from the first surface from light reflected from the second surface;
  detecting the amount of light reflected from the first surface; and
  based on the amount of detected light reflected from the first surface, determining at least one optical characteristic of the substrate, the characteristic comprising a reflectivity, an emissivity, absorptivity, or a transmissivity of the first surface, or a reflectance, an emittance, an absorptance, or a transmittance of the substrate, or mixtures of any of the above;
  wherein at least one optical device comprises at least two optical devices, the at least two optical devices comprising a first lens and a second lens; wherein the light reflected from the first surface is separated from the light reflected from the second surface by at least in part adjusting a focal length of the first lens and a focal length of the second lens.

19. A method for determining at least one optical characteristic of a substrate comprising:
  emitting light onto a first surface of a substrate, the substrate including the first surface and a second and opposite surface separated from the first surface by a thickness;
  directing the light through an optical pathway that includes at least one optical device separate from the substrate that separates the light reflected from the first surface from light reflected from the second surface;
  detecting the amount of light reflected from the first surface; and
  based on the amount of detected light reflected from the first surface, determining at least one optical characteristic of the substrate, the characteristic comprising a reflectivity, an emissivity, absorptivity, or a transmissivity of the first surface, or a reflectance, an emittance, an absorptance, or a transmittance of the substrate, or mixtures of any of the above;
  wherein the light reflected from the first surface is separated from the light reflected from the second surface at least in part by using one blocking device.

* * * * *